US009458182B2

(12) United States Patent
Langer et al.

(10) Patent No.: US 9,458,182 B2
(45) Date of Patent: Oct. 4, 2016

(54) SILYL- AND HETEROATOM-SUBSTITUTED COMPOUNDS SELECTED FROM CARBAZOLES, DIBENZOFURANS, DIBENZOTHIOPHENES AND DIBENZOPHOSPHOLES, AND USE THEREOF IN ORGANIC ELECTRONICS

(75) Inventors: Nicolle Langer, Heppenheim (DE); Christian Schildknecht, Mannheim (DE); Soichi Watanabe, Mannheim (DE); Evelyn Fuchs, Mannheim (DE); Gerhard Wagenblast, Wachenheim (DE); Christian Lennartz, Schifferstadt (DE); Oliver Molt, Hirschberg (DE); Korinna Dormann, Bad Duerkheim (DE); Chuanjie Loh, Singapore (SG); Arvid Hunze, Erlangen (DE); Ralf Krause, Erlangen (DE); Guenter Schmid, Hemhofen (DE); Karsten Heuser, Erlangen (DE); Volker van Elsbergen, Aachen (DE); Herbert Friedrich Boerner, Aachen (DE); Stefan Kirsch, Munich (DE)

(73) Assignees: BASF SE, Ludwigshafen (DE); OLEDWORKS GmbH, Aachen (DE); OSRAM OPTO SEMICONDUCTORS GmbH, Regensburg (DE)

( * ) Notice: Subject to any disclaimer, the term of this patent is extended or adjusted under 35 U.S.C. 154(b) by 975 days.

(21) Appl. No.: 13/143,651

(22) PCT Filed: Dec. 14, 2009

(86) PCT No.: PCT/EP2009/067120
§ 371 (c)(1),
(2), (4) Date: Sep. 28, 2011

(87) PCT Pub. No.: WO2010/079051
PCT Pub. Date: Jul. 15, 2010

(65) Prior Publication Data
US 2012/0012821 A1 Jan. 19, 2012

(30) Foreign Application Priority Data

Jan. 7, 2009 (EP) .................................... 09150176
Jan. 7, 2009 (EP) .................................... 09150181

(51) Int. Cl.
H01L 51/54 (2006.01)
C08G 77/60 (2006.01)
C07D 407/10 (2006.01)
C07F 7/18 (2006.01)
C07F 7/10 (2006.01)
(Continued)

(52) U.S. Cl.
CPC .......... *C07F 7/0814* (2013.01); *C07F 7/0854* (2013.01); *C07F 9/5728* (2013.01); *C07F 9/65517* (2013.01); *C07F 9/65683* (2013.01); *C07F 9/655354* (2013.01); *C09K 11/06* (2013.01); *H01L 51/0072* (2013.01); *H01L 51/0073* (2013.01); *H01L 51/0074* (2013.01); *H01L 51/0094* (2013.01); *H01L 51/5016* (2013.01); *H01L 51/5096* (2013.01)

(58) Field of Classification Search
CPC .......... H01L 51/0072; H01L 51/0094; H01L 51/0065; H01L 51/0067; H01L 51/0068; H01L 51/0073; H01L 51/0074; H01L 51/0085; H01L 51/5016; H01L 51/5096; H01L 51/50; C07F 7/0814; C07F 7/0854; C07F 9/5728; C07F 9/65517; C07F 9/655354; C07F 9/65683; C09K 11/06; C09K 2211/1007; C09K 2211/1011; C09K 2211/1014; C09K 2211/1029; C09K 2211/1044; C09K 2211/1059; C09K 2211/1088; C09K 2211/1092; C09K 11/00; H05B 33/14
See application file for complete search history.

(56) References Cited

U.S. PATENT DOCUMENTS 8,241,764 B2 * 8/2012 Schildknecht et al. ....... 428/690
8,373,159 B2 * 2/2013 Langer et al. .................. 257/40
(Continued)

FOREIGN PATENT DOCUMENTS

EP   1 921 082       5/2008
JP   05-323634    * 12/1993
(Continued)

OTHER PUBLICATIONS

Machine translation for WO 2009/003919 A1 (publication date Jan. 8, 2009).*
(Continued)

*Primary Examiner* — Dawn Garrett
(74) *Attorney, Agent, or Firm* — Oblon, McClelland, Maier & Neustadt, L.L.P.

(57) ABSTRACT

The present invention relates to silyl- and heteroatom-substituted compounds selected from carbazoles, dibenzofurans, dibenzothiophenes and disilylbenzophospholes of the formula (I) or (I*), to the use of the compounds of the formula (I) or (I*) in organic electronics applications, preferably in organic light-emitting diodes, to an organic light-emitting diode comprising at least one compound of the formula (I) or (I*), to a light-emitting layer comprising at least one compound of the formula (I) or (I*), to a blocking layer for holes/excitons comprising at least one compound of the formula (I) or (I*), and to an apparatus selected from the group consisting of stationary visual display units, mobile visual display units, illumination units, keyboards, items of clothing, furniture and wallpaper, comprising at least one inventive organic light-emitting diode.

48 Claims, No Drawings

(51) Int. Cl.
*C07F 7/08* (2006.01)
*C09K 11/06* (2006.01)
*C07F 9/572* (2006.01)
*C07F 9/655* (2006.01)
*C07F 9/6553* (2006.01)
*C07F 9/6568* (2006.01)
*H01L 51/00* (2006.01)
*H01L 51/50* (2006.01)

(56) References Cited

U.S. PATENT DOCUMENTS

| | | | |
|---|---|---|---|
| 8,697,255 B2 * | 4/2014 | Langer et al. | 428/690 |
| 2004/0124766 A1 * | 7/2004 | Nakagawa et al. | 313/504 |
| 2007/0063190 A1 * | 3/2007 | Kobayashi et al. | 257/40 |
| 2007/0224446 A1 | 9/2007 | Nakano et al. | |
| 2007/0262704 A1 | 11/2007 | Tsai et al. | |
| 2008/0171227 A1 | 7/2008 | Kwak et al. | |
| 2008/0213623 A1 * | 9/2008 | Dotz et al. | 428/691 |
| 2010/0219403 A1 | 9/2010 | Langer et al. | |
| 2011/0031477 A1 | 2/2011 | Langer et al. | |

FOREIGN PATENT DOCUMENTS

| | | |
|---|---|---|
| JP | 2006 321750 | 11/2006 |
| WO | 2005 113704 | 12/2005 |
| WO | WO 2009/003919 A1 * | 1/2009 |

OTHER PUBLICATIONS

Baldo, M.A., et al., "Very high-efficiency green organic light-emitting devices based on electrophosphorescence," Applied Physics Letters, vol. 75, No. 1, pp. 4-6, (Jul. 5, 1999).

International Search Report issued Feb. 18, 2010 in PCT/EP09/067120 filed Dec. 14, 2009.

U.S. Appl. No. 13/516,117, filed Aug. 27, 2012, Molt, et al.

* cited by examiner

SILYL- AND HETEROATOM-SUBSTITUTED COMPOUNDS SELECTED FROM CARBAZOLES, DIBENZOFURANS, DIBENZOTHIOPHENES AND DIBENZOPHOSPHOLES, AND USE THEREOF IN ORGANIC ELECTRONICS

The present invention relates to silyl- and heteroatom-substituted compounds selected from carbazoles, dibenzofurans, dibenzothiophenes and disilylbenzophospholes of the formula (I) or (I*), to the use of the compounds of the formula (I) or (I*) in organic electronics applications, preferably in organic light-emitting diodes, to an organic light-emitting diode comprising at least one compound of the formula (I) or (I*), to a light-emitting layer comprising at least one compound of the formula (I) or (I*), to a blocking layer for holes/excitons comprising at least one compound of the formula (I) or (I*), and to an apparatus selected from the group consisting of stationary visual display units, mobile visual display units, illumination units, keyboards, items of clothing, furniture and wallpaper, comprising at least one inventive organic light-emitting diode.

Organic electronics is a subfield of electronics and uses electronic circuits which comprise polymers or smaller organic compounds. Fields of use of organic electronics are the use of polymers or smaller organic compounds in organic light-emitting diodes (OLEDs), use in organic solar cells (organic photovoltaics) and in switching elements such as organic transistors, for example organic FETs and organic TFTs.

The use of suitable novel organic materials thus allows various new types of components based on organic electronics to be provided, such as displays, sensors, transistors, data stores or photovoltaic cells. This makes possible the development of new applications which are thin, light, flexible and producible at low cost.

A preferred field of use according to the present application is the use of relatively small organic compounds in organic light-emitting diodes.

Organic light-emitting diodes (OLEDs) exploit the property of materials of emitting light when they are excited by electrical current. OLEDs are of particular interest as an alternative to cathode ray tubes and liquid-crystal displays for producing flat visual display units. Owing to the very compact design and the intrinsically low power consumption, the devices comprising OLEDs are suitable especially for mobile applications, for example for applications in cellphones, laptops, etc., and for illumination.

The basic principles of the way in which OLEDs work and suitable structures (layers) of OLEDs are specified, for example, in WO 2005/113704 and the literature cited therein. The light-emitting materials (emitters) used may, as well as fluorescent materials (fluorescence emitters), be phosphorescent materials (phosphorescence emitters). The phosphorescence emitters are typically organometallic complexes which, in contrast to the fluorescence emitters which exhibit singlet emission, exhibit triplet emission (M. A. Baldow et al., Appl. Phys. Lett. 1999, 75, 4 to 6). For quantum-mechanical reasons, when the phosphorescence emitters are used, up to four times the quantum efficiency, energy efficiency and power efficiency is possible.

Of particular interest are organic light-emitting diodes with long operative lifetime, good efficiency, high stability to thermal stress and a low use and operating voltage.

In order to implement the aforementioned properties in practice, it is not only necessary to provide suitable emitter materials, but the other components of the OLED (complementary materials) must also be balanced to one another in suitable device compositions. Such device compositions may, for example, comprise specific matrix materials in which the actual light emitter is present in distributed form. In addition, the compositions may comprise blocker materials, it being possible for hole blockers, exciton blockers and/or electron blockers to be present in the device compositions. Additionally or alternatively, the device compositions may further comprise hole injection materials and/or electron injection materials and/or charge transport materials such as hole conductor materials and/or electron conductor materials. The selection of the aforementioned materials which are used in combination with the actual light emitter has a significant influence on parameters including the efficiency and the lifetime, and the use and operating voltages, of the OLEDs.

The prior art proposes numerous different materials for use in the different layers of OLEDs.

US 2008/0171227 A1 relates to a silanylamine-based compound of the formula (I) and to an OLED comprising the silanylamine-based compound.

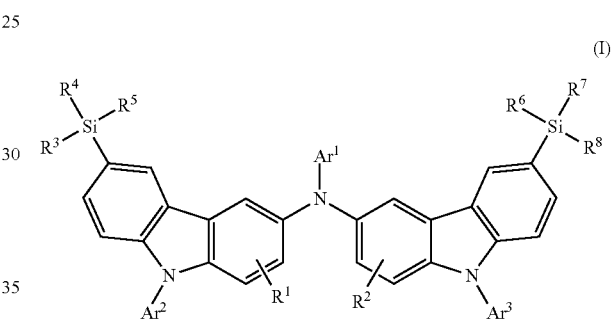

(I)

The silanylamine-based compound which has two silane groups and two or more carbazole groups has electrical stability, good charge transport capacities and a high glass transition temperature, and can be used as a hole injection material, hole transport material and/or emitting material.

EP 1 921 082 A1 relates to a silanylamine-based compound of the formula (I) and to organic light-emitting diodes which comprise a silanylamine-based compound of the formula (I).

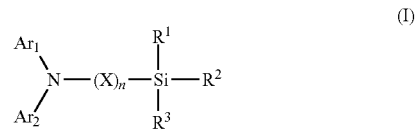

(I)

The silanylamine-based compound of the formula (I) can be used as a hole injection layer, hole transport layer or as a sole layer which has both hole injection properties and hole transport properties. In addition, the silanylamine-based compound of the formula (I) can be used in an emitting layer which may additionally comprise phosphorescent or fluorescent material.

JP 2006-321750 A relates to aromatic compounds, for example dibenzofuran derivatives, dibenzothiophene derivatives or carbazole derivatives of the formula (1-1)

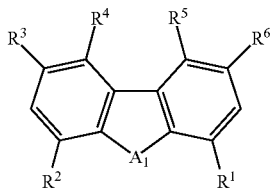

(1-1)

The compounds of the formula (1-1) can, according to JP 2006-321750 A, be used as intermediates for medicaments, charge transport material or luminescent material. US 2007/0224446 A1 relates to compounds which are suitable for use in organic light-emitting diodes, said compounds having the general formula (I).

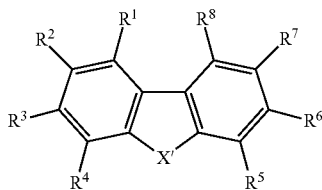

(I)

The $R^1$ to $R^8$ radicals in formula (I) may be groups including arylsilyl groups having 8 to 40 carbon atoms. According to the examples in US 2007/0224446 A1, a compound of the formula (I) is used as a matrix material in a light-emitting layer.

It is thus evident from the prior art that carbazole, dibenzofuran and dibenzothiophene derivatives are known, and are used especially as a hole injection material, hole transport material and if appropriate as a matrix material in a light-emitting layer.

It is an object of the present invention, with respect to the aforementioned prior art, to provide further materials suitable for use in OLEDs and further applications in organic electronics. More particularly, it should be possible to provide hole/exciton blocker materials and matrix materials for use in OLEDs. The materials should be suitable especially for OLEDs which comprise at least one phosphorescence emitter, especially at least one green emitter or at least one blue emitter. Furthermore, the materials should be suitable for providing OLEDs which ensure good efficiencies, good operative lifetimes and a high stability to thermal stress, and a low use and operating voltage of the OLEDs.

This object is achieved by the provision of compounds of the formula (I) or (I*)

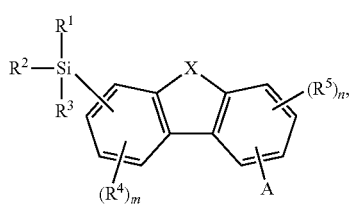

(I)

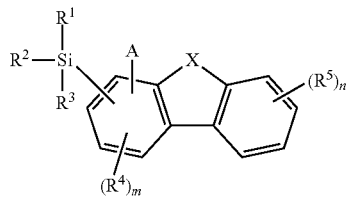

(I*)

in which
X is NR, S, O or PR;
R is aryl, heteroaryl, alkyl, cycloalkyl or heterocycloalkyl;
A is $-NR^6R^7$, $-P(O)R^8R^9$, $-PR^{10}R^{11}$, $-S(O)_2R^{12}$, $-S(O)R^{13}$, $-SR^{14}$ or $-OR^{15}$;
$R^1$, $R^2$, $R^3$ are each independently aryl, heteroaryl, alkyl, cycloalkyl, heterocycloalkyl, a crosslinkable or polymerizable group attached via a spacer, where at least one of the $R^1$, $R^2$, $R^3$ radicals comprises at least two carbon atoms, or $OR^{22}$,
$R^4$, $R^5$ are each independently alkyl, cycloalkyl, heterocycloalkyl, aryl, heteroaryl, a crosslinkable or polymerizable group attached via a spacer, an A group or a group with donor or acceptor action;
n, m are each independently 0, 1, 2, 3;
$R^6$, $R^7$ together with the nitrogen atom form a cyclic radical which has 3 to 10 ring atoms, which may be unsubstituted or substituted by one or more substituents selected from alkyl, cycloalkyl, heterocycloalkyl, aryl, heteroaryl and a group with donor or acceptor action, and/or may be fused to one or more further cyclic radicals having 3 to 10 ring atoms, where the fused radicals may be unsubstituted or substituted by one or more substituents selected from alkyl, cycloalkyl, heterocycloalkyl, aryl, heteroaryl, a crosslinkable or polymerizable group attached via a spacer, and a group with donor or acceptor action;
$R^{22}$ is independently $SiR^{23}R^{24}R^{25}$, aryl, heteroaryl, alkyl, cycloalkyl or heterocycloalkyl, a crosslinkable or polymerizable group attached via a spacer, optionally substituted by an $OR^{28}$ group,
$R^{28}$ is independently $SiR^{23}R^{24}R^{25}$, heteroaryl, alkyl, cycloalkyl or heterocycloalkyl, a crosslinkable or polymerizable group attached via a spacer,
$R^8$, $R^9$, $R^{10}$, $R^{11}$, $R^{12}$, $R^{13}$, $R^{14}$, $R^{15}$, $R^{23}$, $R^{24}$, $R^{25}$ are each independently aryl, heteroaryl, alkyl, cycloalkyl or heterocycloalkyl, a crosslinkable or polymerizable group attached via a spacer,
or
two units of the general formula (I) and/or (I*) are bridged to one another via a linear or branched, saturated or unsaturated bridge optionally interrupted by at least one heteroatom or via O, where this bridge in the general formula (I) and/or (I*) is in each case attached to the silicon atoms instead of $R^2$.

The object of the invention is also achieved by compounds of the formula (I)

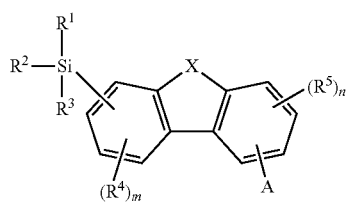

(I)

in which

X is NR, S, O or PR;

R is aryl, heteroaryl, alkyl, cycloalkyl or heterocycloalkyl;

A is —$NR^6R^7$, —$P(O)R^8R^9$, —$S(O)_2R^{12}$, —$S(O)R^{13}$, —$SR^{14}$ or —$OR^{15}$;

$R^1$, $R^2$, $R^3$ are each independently aryl, heteroaryl, alkyl, cycloalkyl or heterocycloalkyl, where at least one of the $R^1$, $R^2$ and $R^3$ radicals is aryl or heteroaryl;

$R^4$, $R^5$ are each independently alkyl, cycloalkyl, heterocycloalkyl, aryl, heteroaryl, an A group or a group with donor or acceptor action;

n, m are each independently 0, 1, 2, 3;

$R^6$, $R^7$ together with the nitrogen atom form a cyclic radical which has 3 to 10 ring atoms and may be unsubstituted or substituted by one or more substituents selected from alkyl, cycloalkyl, heterocycloalkyl, aryl, heteroaryl and a group with donor or acceptor action, and/or may be fused to one or more further cyclic radicals having 3 to 10 ring atoms, where the fused radicals may be unsubstituted or substituted by one or more substituents selected from alkyl, cycloalkyl, heterocycloalkyl, aryl, heteroaryl and a group with donor or acceptor action;

$R^8$, $R^9$, $R^{10}$, $R^{11}$, $R^{12}$, $R^{13}$, $R^{14}$ and $R^{15}$ are each independently aryl, heteroaryl, alkyl, cycloalkyl or heterocycloalkyl.

It has been found that the specific silyl- and heteroatom-substituted compounds of the formula (I) or (I*) are particularly suitable for use in applications in which charge carrier conductivity is required, especially for use in organic electronics applications, for example selected from switching elements such as organic transistors, e.g. organic FETs and organic TFTs, organic solar cells and organic light-emitting diodes (OLEDs), the compounds of the formula (I) or (I*) being particularly suitable in OLEDs for use as matrix material in a light-emitting layer and/or as hole and/or exciton blocker material and/or as electron and/or exciton blocker material, especially in combination with a phosphorescence emitter. In the case of use of the inventive compounds of the formula (I) or (I*) in OLEDs, OLEDs which have good efficiencies and a long lifetime and which can be operated especially at a low use and operating voltage are obtained. The inventive compounds of the formula (I) or (I*) are suitable especially for use as matrix and/or hole/exciton blocker materials for blue and green emitters, for example light blue or deep blue emitters, these being especially phosphorescence emitters. Furthermore, the compounds of the formula (I) or (I*) can be used as conductor/complementary materials in organic electronics applications selected from switching elements and organic solar cells.

In the context of the present application, the terms aryl radical or group, heteroaryl radical or group, alkyl radical or group, cycloalkyl radical or group, heterocycloalkyl radical or group, alkenyl radical or group, alkynyl radical or group, aralkyl radical or group, and groups with donor and/or acceptor action are each defined as follows:

An aryl radical (or group) is understood to mean a radical which has a base skeleton of from 6 to 30 carbon atoms, preferably from 6 to 18 carbon atoms, and which is formed from an aromatic ring or a plurality of fused aromatic rings. Suitable base skeletons are, for example, phenyl, naphthyl, anthracenyl or phenanthrenyl, indenyl or fluorenyl. This base skeleton may be unsubstituted (i.e. all carbon atoms which are substitutable bear hydrogen atoms) or be substituted at one, more than one or all substitutable positions of the base skeleton.

Suitable substituents are, for example, deuterium, alkoxy radicals, aryloxy radicals, alkylamino groups, arylamino groups, carbazolyl groups, silyl groups, $SiR^{16}R^{17}R^{18}$, suitable silyl groups $SiR^{16}R^{17}R^{18}$ being specified below, alkyl radicals, preferably alkyl radicals having from 1 to 8 carbon atoms, more preferably methyl, ethyl or i-propyl, aryl radicals, preferably $C_6$-aryl radicals, which may in turn be substituted or unsubstituted, heteroaryl radicals, preferably heteroaryl radicals which comprise at least one nitrogen atom, more preferably pyridyl radicals and carbazolyl radicals, alkenyl radicals, preferably alkenyl radicals which bear one double bond, more preferably alkenyl radicals with one double bond and from 1 to 8 carbon atoms, alkynyl radicals, preferably alkynyl radicals with one triple bond, more preferably alkynyl radicals with one triple bond and from 1 to 8 carbon atoms, or groups with donor or acceptor action or crosslinkable or polymerizable groups attached via a spacer. Suitable groups with donor or acceptor action are specified below. Most preferably, the substituted aryl radicals bear substituents selected from the group consisting of methyl, ethyl, isopropyl, alkoxy, heteroaryl, halogen, pseudohalogen and amino, preferably arylamino. The aryl radical or the aryl group is preferably a $C_6$-$C_{18}$-aryl radical, more preferably a $C_6$-aryl radical, which is optionally substituted by at least one or more than one of the aforementioned substituents. More preferably, the $C_6$-$C_{18}$-aryl radical, preferably $C_6$-aryl radical, has none, one, two, three or four, most preferably none, one or two, of the aforementioned substituents.

A heteroaryl radical or a heteroaryl group is understood to mean radicals which differ from the aforementioned aryl radicals in that, in the base skeleton of the aryl radicals, at least one carbon atom is replaced by a heteroatom, and in that the base skeleton of the heteroaryl radicals has preferably from 5 to 18 ring atoms. Preferred heteroatoms are N, O and S. Particularly preferred suitable heteroaryl radicals are nitrogen-containing heteroaryl radicals. Most preferably, one or two carbon atoms of the base skeleton are replaced by heteroatoms, preferably nitrogen. Especially preferably, the base skeleton is selected from systems such as pyridine, pyrimidine and five-membered heteroaromatics such as pyrrole, furan, pyrazole, imidazole, thiophene, oxazole, thiazole, triazole. In addition, the heteroaryl radicals may be fused ring systems, for example benzofuryl, benzothienyl, benzopyrrolyl, dibenzofuryl, dibenzothienyl, phenanthrolinyl, carbazolyl radicals, azacarbazolyl radicals or diazacarbazoyl radicals. The base skeleton may be substituted at one, more than one or all substitutable positions of the base skeleton. Suitable substituents are the same as have already been specified for the aryl groups.

An alkyl radical or an alkyl group is understood to mean a radical having from 1 to 20 carbon atoms, preferably from 1 to 10 carbon atoms, more preferably from 1 to 8 and most preferably from 1 to 4 carbon atoms. This alkyl radical may be branched or unbranched and may optionally be interrupted by one or more heteroatoms, preferably Si, N, O or S, more preferably N, O or S. In addition, this alkyl radical may be substituted by one or more of the substituents specified for the aryl groups. In addition, the alkyl radicals present in accordance with the invention may have at least one halogen atom, for example F, Cl, Br or I, especially F. In a further embodiment, the alkyl radicals present in accordance with the invention may be fully fluorinated. It is likewise possible that the alkyl radical bears one or more (hetero)aryl groups. In the context of the present application, for example, benzyl radicals are thus substituted alkyl radicals. All of the above-listed (hetero)aryl groups are suitable. The alkyl radicals are more preferably selected from the group consisting of methyl, ethyl, isopropyl, n-propyl, n-butyl, isobutyl and tert-butyl; very particular preference is given to methyl and ethyl.

A cycloalkyl radical or a cycloalkyl group is understood to mean a radical having from 3 to 20 carbon atoms, preferably from 3 to 10 carbon atoms, more preferably from 3 to 8 carbon atoms. This base skeleton may be unsubstituted (i.e. all carbon atoms which are substitutable bear hydrogen atoms) or may be substituted at one, more than one or all substitutable positions of the base skeleton. Suitable substituents are the groups already specified above for the aryl radicals. It is likewise possible that the cycloalkyl radical bears one or more (hetero)aryl groups. Examples of suitable cycloalkyl radicals are cyclopropyl, cyclopentyl and cyclohexyl.

A heterocycloalkyl radical or a heterocycloalkyl group is understood to mean radicals which differ from the aforementioned cycloalkyl radicals in that, in the base skeleton of the cycloalkyl radicals, at least one carbon atom is replaced by a heteroatom. Preferred heteroatoms are N, O and S. Most preferably, one or two carbon atoms of the base skeleton of the cycloalkyl radicals are replaced by heteroatoms. Examples of suitable heterocycloalkyl radicals are radicals derived from pyrrolidine, piperidine, piperazine, tetrahydrofuran, dioxane.

An alkenyl radical or an alkenyl group is understood to mean a radical which corresponds to the aforementioned alkyl radicals having at least two carbon atoms, with the difference that at least one C—C single bond of the alkyl radical is replaced by a C—C double bond. The alkynyl radical preferably has one or two double bonds.

An alkynyl radical or an alkynyl group is understood to mean a radical which corresponds to the aforementioned alkyl radicals having at least two carbon atoms, with the difference that at least one C—C single bond of the alkyl radical is replaced by a C—C triple bond. The alkenyl radical preferably has one or two triple bonds.

An $SiR^{16}R^{17}R^{18}$ group is understood to mean a silyl radical in which
$R^{16}$, $R^{17}$ and $R^{18}$ are each independently alkyl, cycloalkyl, heterocycloalkyl, aryl, heteroaryl or $OR^{22}$.

An $SiR^{23}R^{24}R^{25}$ group is understood to mean a silyl radical in which
$R^{23}$, $R^{24}$ and $R^{25}$ are each independently alkyl, cycloalkyl, heterocycloalkyl, aryl, heteroaryl or $OR^{22}$.

In the context of the present application, a group or a substituent with donor or acceptor action is understood to mean the following groups:

Groups with donor action are understood to mean groups which have a +I and/or +M effect, and groups with acceptor action to mean groups which have a −I and/or −M effect. Preferred suitable groups are selected from $C_1$-$C_{20}$-alkoxy, $C_6$-$C_{30}$-aryloxy, $C_1$-$C_{20}$-alkylthio, $C_6$-$C_{30}$-arylthio, $SiR^{19}R^{20}R^{21}$, $OR^{22}$, halogen radicals, halogenated $C_1$-$C_{20}$-alkyl radicals, carbonyl (—CO($R^{19}$)), carbonylthio (—C=O (S$R^{19}$)), carbonyloxy (—C=O(O$R^{19}$)), oxycarbonyl (—OC=O($R^{19}$)), thiocarbonyl (—SC=O($R^{19}$)), amino (—N$R^{19}R^{20}$), pseudohalogen radicals, amido (—C=O (N$R^{19}$)), —N$R^{19}$C=O($R^{21}$), phosphonate (—P(O) (O$R^{19}$)$_2$, phosphate (—OP(O) (O$R^{19}$)$_2$), phosphine (—P$R^{19}R^{20}$), phosphine oxide (—P(O)$R^{19}$$_2$), sulfate (—OS(O)$_2$O$R^{19}$), sulfoxide (—S(O)$R^{19}$), sulfonate (—S(O)$_2$O$R^{19}$), sulfonyl (—S(O)$_2R^{19}$, sulfonamide (—S(O)$_2$N$R^{19}R^{20}$), NO$_2$, boronic esters (—OB(O$R^{19}$)$_2$), imino (—C=, N$R^{19}R^{20}$)), borane radicals, stannane radicals, hydrazine radicals, hydrazone radicals, oxime radicals, nitroso groups, diazo groups, vinyl groups, sulfoximines, alanes, germanes, boroximes and borazines.

The $R^{19}$, $R^{20}$ and $R^{21}$ radicals mentioned in the aforementioned groups with donor or acceptor action are each independently:

Substituted or unsubstituted $C_1$-$C_{20}$-alkyl or substituted or unsubstituted $C_6$-$C_{30}$-aryl or $OR^{22}$, suitable and preferred alkyl and aryl radicals having been specified above. The $R^{19}$, $R^{20}$ and $R^{21}$ radicals are more preferably each $C_1$-$C_6$-alkyl, e.g. methyl, ethyl or i-propyl, or phenyl. In a preferred embodiment—in the case of $SiR^{19}R^{20}R^{21}$—$R^{19}$, $R^{20}$ and $R^{21}$ are preferably each independently substituted or unsubstituted $C_1$-$C_{20}$-alkyl or substituted or unsubstituted aryl, preferably phenyl.

Preferred substituents with donor or acceptor action are selected from the group consisting of:

$C_1$- to $C_{20}$-alkoxy, preferably $C_1$-$C_6$-alkoxy, more preferably ethoxy or methoxy; $C_6$-$C_{30}$-aryloxy, preferably $C_6$-$C_{10}$-aryloxy, more preferably phenyloxy; $SiR^{19}R^{20}R^{21}$ where $R^{19}$, $R^{20}$ and $R^{21}$ are preferably each independently substituted or unsubstituted alkyl or substituted or unsubstituted aryl, preferably phenyl; more preferably, at least one of the $R^{19}$, $R^{20}$ and $R^{21}$ radicals is substituted or unsubstituted phenyl, suitable substituents having been specified above; halogen radicals, preferably F, Cl, more preferably F, halogenated $C_1$-$C_{20}$-alkyl radicals, preferably halogenated $C_1$-$C_6$-alkyl radicals, most preferably fluorinated $C_1$-$C_6$-alkyl radicals, e.g. $CF_3$, $CH_2F$, $CHF_2$ or $C_2F_5$; amino, preferably dimethylamino, diethylamino or diarylamino, more preferably diarylamino; pseudohalogen radicals, preferably CN, —C(O)O$C_1$-$C_4$-alkyl, preferably —C(O)OMe, P(O)$R_2$, preferably P(O)Ph$_2$.

Very particularly preferred substituents with donor or acceptor action are selected from the group consisting of methoxy, phenyloxy, halogenated $C_1$-$C_4$-alkyl, preferably $CF_3$, $CH_2F$, $CHF_2$, $C_2F_5$, halogen, preferably F, CN, $SiR^{19}R^{20}R^{21}$, suitable $R^{19}$, $R^{20}$ and $R^{21}$ radicals already having been specified, diarylamino (N$R^{19}R^{20}$, where $R^{19}$, $R^{20}$ are each $C_6$-$C_{30}$-aryl), —C(O)O$C_1$-$C_4$-alkyl, preferably —C(O)OMe, P(O)Ph$_2$.

Halogen groups are preferably understood to mean F, Cl and Br, more preferably F and Cl, most preferably F.

Pseudohalogen groups are preferably CN, SCN and OCN, more preferably CN.

The aforementioned groups with donor or acceptor action do not rule out that further radicals and substituents which are specified in the present application but are not included in the above list of groups with donor or acceptor action have donor or acceptor action.

The aryl radicals or groups, heteroaryl radicals or groups, alkyl radicals or groups, cycloalkyl radicals or groups, heterocycloalkyl radicals or groups, alkenyl radicals or groups and groups with donor and/or acceptor action may—as mentioned above—be substituted or unsubstituted. In the context of the present application, an unsubstituted group is understood to mean a group in which the substitutable atoms of the group bear hydrogen atoms. In the context of the present application, a substituted group is understood to mean a group in which one or more substitutable atom(s) bear(s) a substituent instead of a hydrogen atom at least at one position. Suitable substituents are the substituents already mentioned above with regard to the aryl radicals or groups.

When radicals with the same numbering occur more than once in the compounds of the present application, these radicals may each independently have the definitions specified.

The X radical in the compounds of the formula (I) or (I*) is NR, S, O or PR, preferably NR, S or O, more preferably O or S, most preferably O.

The R radical is aryl, heteroaryl, alkyl, cycloalkyl or heterocycloalkyl, preferably aryl, heteroaryl or alkyl, more preferably aryl, where the aforementioned radicals may be unsubstituted or substituted. Suitable substituents have been specified above. R is more preferably phenyl which may be substituted by the aforementioned substituents or unsubstituted. R is most preferably unsubstituted phenyl.

The A group in the compounds of the formula (I) or (I*) is —NR$^6$R$^7$, —P(O)R$^8$R$^9$, —PR$^{10}$R$^{11}$, —S(O)$_2$R$^{12}$, —S(O)R$^{13}$, —SR$^{14}$ order —OR$^{15}$; preferably NR$^6$R$^7$, —P(O)R$^8$R$^9$ or —OR$^{15}$, more preferably —NR$^6$R$^7$.

The R$^6$ to R$^{15}$ radicals are each defined as follows:

R$^6$, R$^7$ together with the nitrogen atom form a cyclic radical which has 3 to 10 ring atoms and may be unsubstituted or substituted by one or more substituents selected from the group of alkyl, cycloalkyl, heterocycloalkyl, aryl, heteroaryl and a group with donor or acceptor action, and/or may be fused to one or more further cyclic radicals having 3 to 10 ring atoms, where the fused radicals may be unsubstituted or substituted by one or more substituents selected from alkyl, cycloalkyl, heterocycloalkyl, aryl, heteroaryl, a crosslinkable or polymerizable group attached via a spacer, and a group with donor or acceptor action;

R$^8$, R$^9$, R$^{10}$, R$^{11}$, R$^{12}$, R$^{13}$, R$^{14}$, R$^{15}$, R$^{23}$, R$^{24}$, R$^{25}$ are each independently aryl, heteroaryl, alkyl, cycloalkyl or heterocycloalkyl, a crosslinkable or polymerizable group attached via a spacer, preferably aryl or heteroaryl, where the radicals group may be unsubstituted or substituted by one or more of the radicals selected from alkyl, cycloalkyl, heterocycloalkyl, aryl, heteroaryl and a group with donor or acceptor action, more preferably unsubstituted or substituted phenyl, suitable substituents having been specified above, for example tolyl or a group of the formula

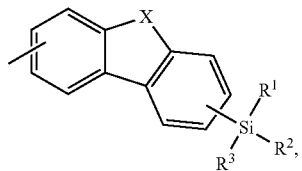

in which the X group and the R$^1$, R$^2$ and R$^3$ radicals are each independently as defined for the compounds of the formula (I) or (I*).

R$^8$, R$^9$, R$^{10}$, R$^{11}$, R$^{12}$, R$^{13}$, R$^{14}$ and R$^{15}$ are most preferably each independently phenyl, tolyl or a group of the formula

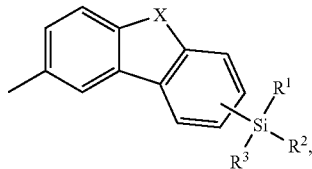

in which X is NPh, S or O.

Examples of —NR$^6$R$^7$ groups suitable with preference are selected from the group consisting of pyrrolyl, 2,5-dihydro-1-pyrrolyl, pyrrolidinyl, indolyl, indolinyl, isoindolinyl, carbazolyl, azacarbazolyl, diazacarbazolyl, imidazolyl, imidazolinyl, benzimidazolyl, pyrazolyl, indazolyl, 1,2,3-triazolyl, benzotriazolyl, 1,2,4-triazolyl, tetrazolyl, 1,3-oxazolyl, 1,3-thiazolyl, piperidyl, morpholinyl, 9,10-dihydroacridinyl and 1,4-oxazinyl, where the aforementioned groups may be unsubstituted or substituted by one or more substituents selected from alkyl, cycloalkyl, heterocycloalkyl, aryl, heteroaryl and a group with donor or acceptor action, the —NR$^6$R$^7$ group preferably being selected from carbazolyl, pyrrolyl, indolyl, imidazolyl, benzimidazolyl, azacarbazolyl and diazacarbazolyl, where the aforementioned groups may be unsubstituted or substituted by one or more substituents selected from alkyl, cycloalkyl, heterocycloalkyl, aryl, heteroaryl and a group with donor or acceptor action, the —NR$^6$R$^7$ group more preferably being carbazolyl which may be unsubstituted or substituted by one or more substituents selected from alkyl, cycloalkyl, heterocycloalkyl, aryl, heteroaryl and a group with donor or acceptor action.

Particularly preferred —NR$^6$R$^7$ groups are:

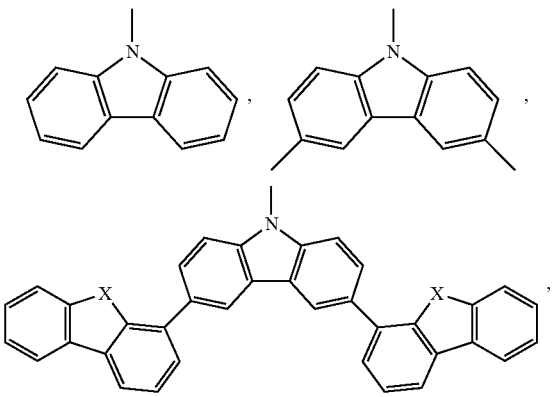

in which X is NPh, S or O,

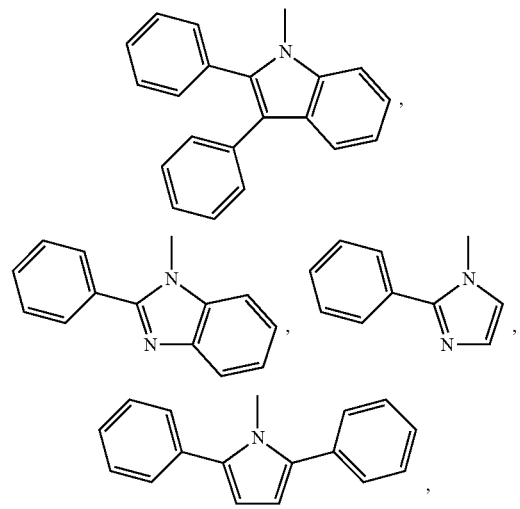

-continued
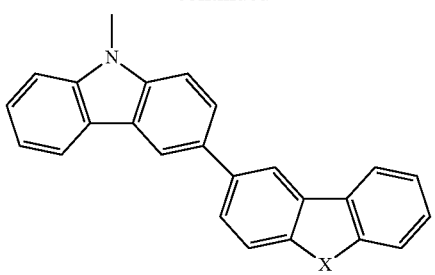
in which X is NPh, S or O,
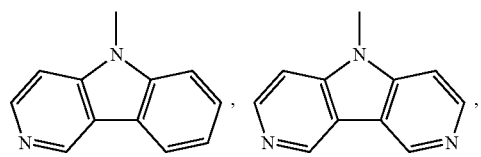
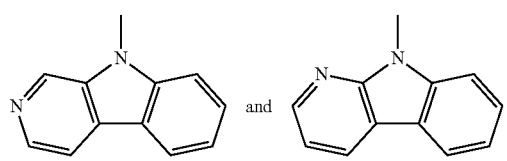
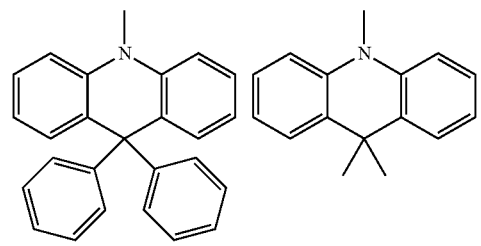
Particularly preferred —P(O)R⁸R⁹ groups are:
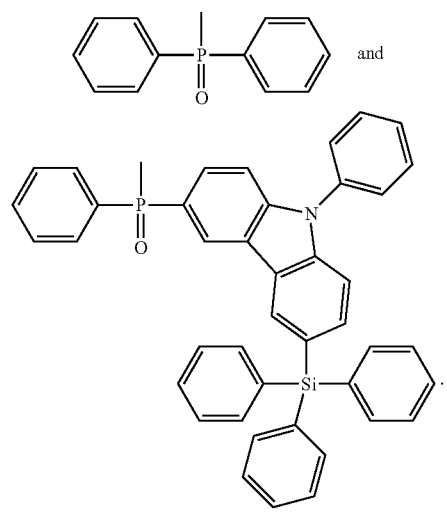
A particularly preferred PR¹⁰R¹¹ group is:
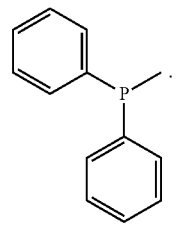
Particularly preferred —S(O)₂R¹² and —S(O)R¹³ groups are:
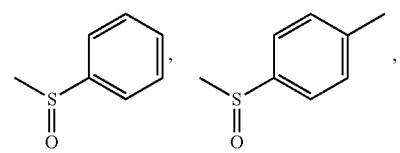
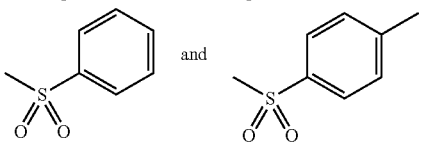
Particularly preferred —SR¹⁴ and —OR¹⁵ groups are:
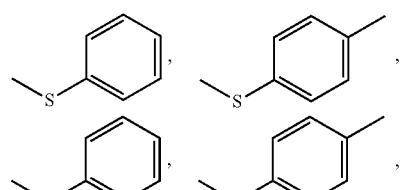
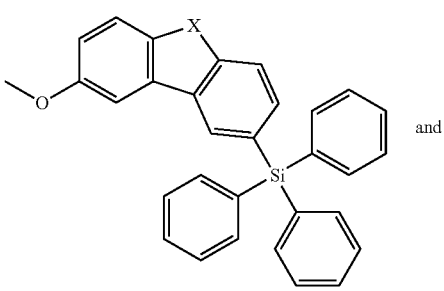
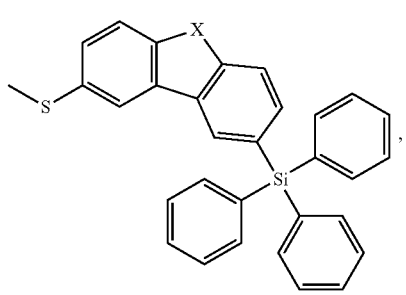
in which X in each case is NPh, S or O.

$R^4$, $R^5$ in the compounds of the formula (I) or (I*) are each independently alkyl, cycloalkyl, heterocycloalkyl, aryl, heteroaryl, a further A group, a crosslinkable or polymerizable group attached via a spacer or a group with donor or acceptor action; preferably each independently alkyl, aryl, heteroaryl or a group with donor or acceptor action. For example, $R^4$ or $R^5$ may each independently be:

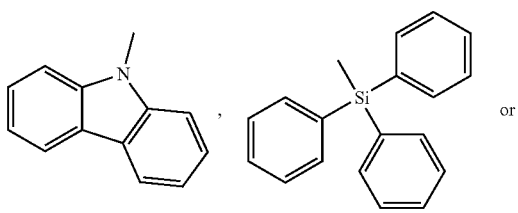

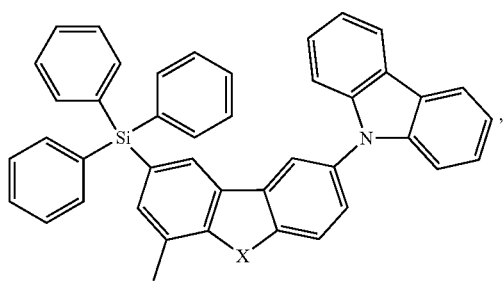

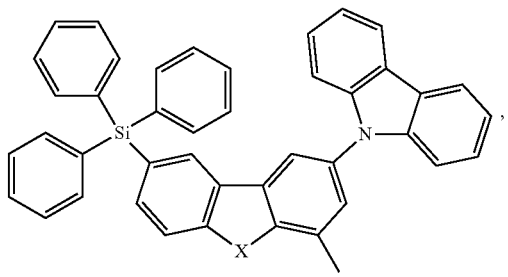

in which X is NPh, S or O.

In the compounds of the formula (I) or (I*), n $R^4$ groups and/or m $R^5$ groups may be present, where n and m are:
n, m are each independently 0, 1, 2 or 3; preferably each independently 0, 1 or 2. Most preferably, at least n or m is 0.

$R^{22}$ in the compounds of the general formula (I) or (I*) is generally independently $SiR^{23}R^{24}R^{25}$, aryl, heteroaryl, alkyl, cycloalkyl or heterocycloalkyl, a crosslinkable or polymerizable group attached via a spacer, optionally substituted by an $OR^{28}$ group, preferably aryl, alkyl, optionally substituted by an $OR^{28}$ group, more preferably aryl, alkyl.

$R^{28}$ in compounds of the general formula (I) or (I*) is generally independently $SiR^{23}R^{24}R^{25}$, independently aryl, alkyl, cycloalkyl or heterocycloalkyl, a crosslinkable of polymerizable group attached via a spacer.

The optionally present $OR^{28}$ substituent may be present in the radicals mentioned generally at all positions which appear suitable to the person skilled in the art.

In a further preferred embodiment of the present invention, two units of the general formula (I) and/or (I*) are bridged to one another via a linear or branched, saturated or unsaturated bridge interrupted by at least one heteroatom or via O, where this bridge in the general formula (I) and/or (I*) is in each case bonded to the silicon atoms instead of $R^2$.

The bridge is preferably selected from the group consisting of —$CH_2$—, —$C_2H_4$—, —$C_4H_8$—, —$C_6H_{12}$—, —$C_8H_{16}$—, —$C_9H_{18}$—, —$CH(C_8H_{17})CH_2$—, —$C_2H_4$(CF_2)_8C_2H_4$—, —C≡C—, -1,4-(CH_2)_2$-phenyl-$(CH_2)_2$—, 1,3-$(CH_2)_2$-phenyl-$(CH_2)_2$—, -1,4-phenyl-, -1,3-phenyl-, —O—, —O—Si(CH_3)_2$—O—, —O—Si(CH_3)_2$—O—Si(CH_3)_2$—O—, —O—

In a preferred embodiment of the present application, the compounds of the general formula (I) or (I*) have the general formula (Ia), (Ib) or (Ic):

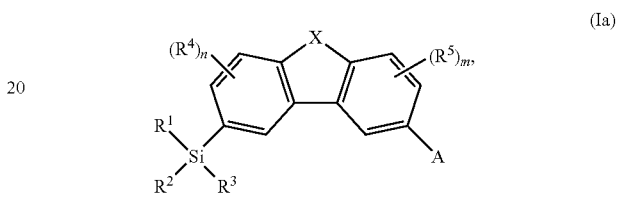
(Ia)

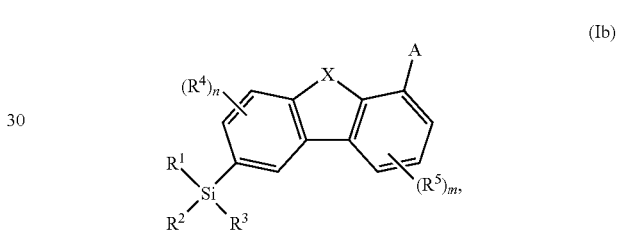
(Ib)

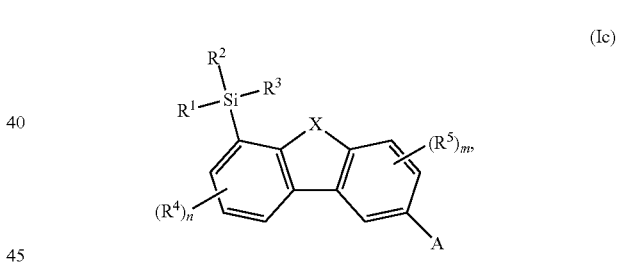
(Ic)

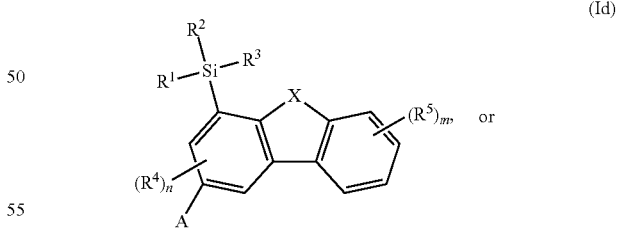
(Id)
or

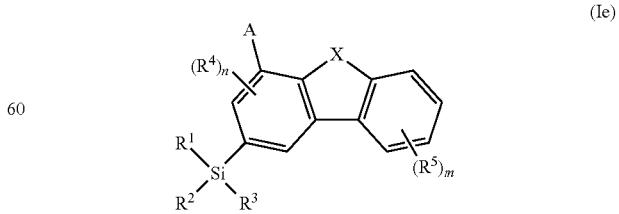
(Ie)

in which the A, X, $R^1$, $R^2$, $R^3$, $R^4$ and $R^5$ radicals are each as defined above.

In a further preferred embodiment of the present invention, $R^1$ and/or $R^2$ and/or $R^3$ are aromatic units of the general formula (Ii) and/or (Ii*)
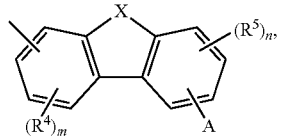
(Ii)
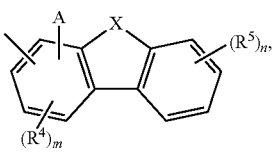
(Ii*)
where $R^4$, $R^5$, A and X are each as defined above.
Suitable compounds of the formula (I) or (I*) are, for example:
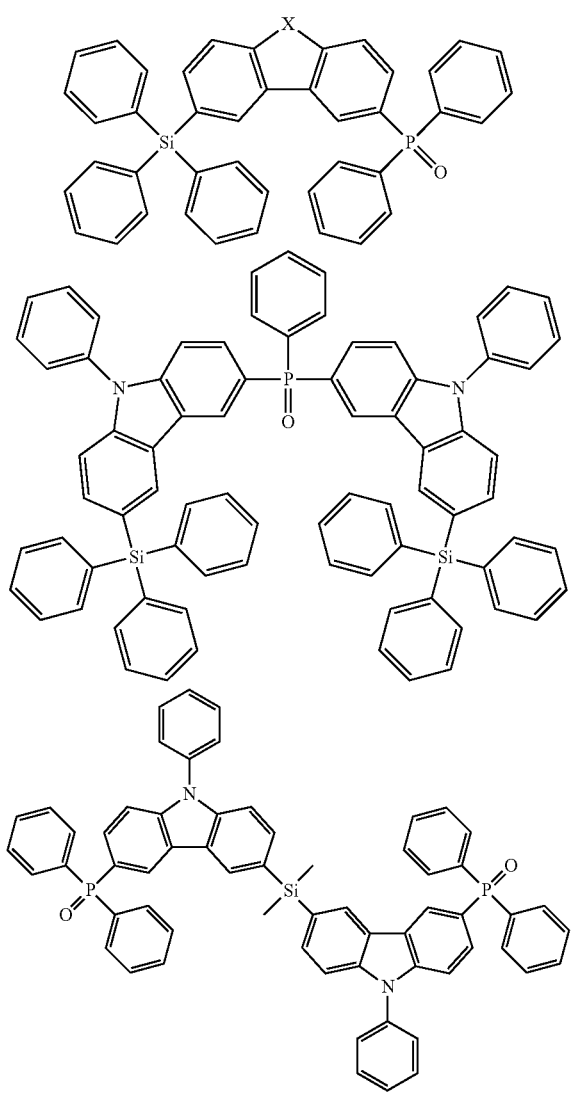
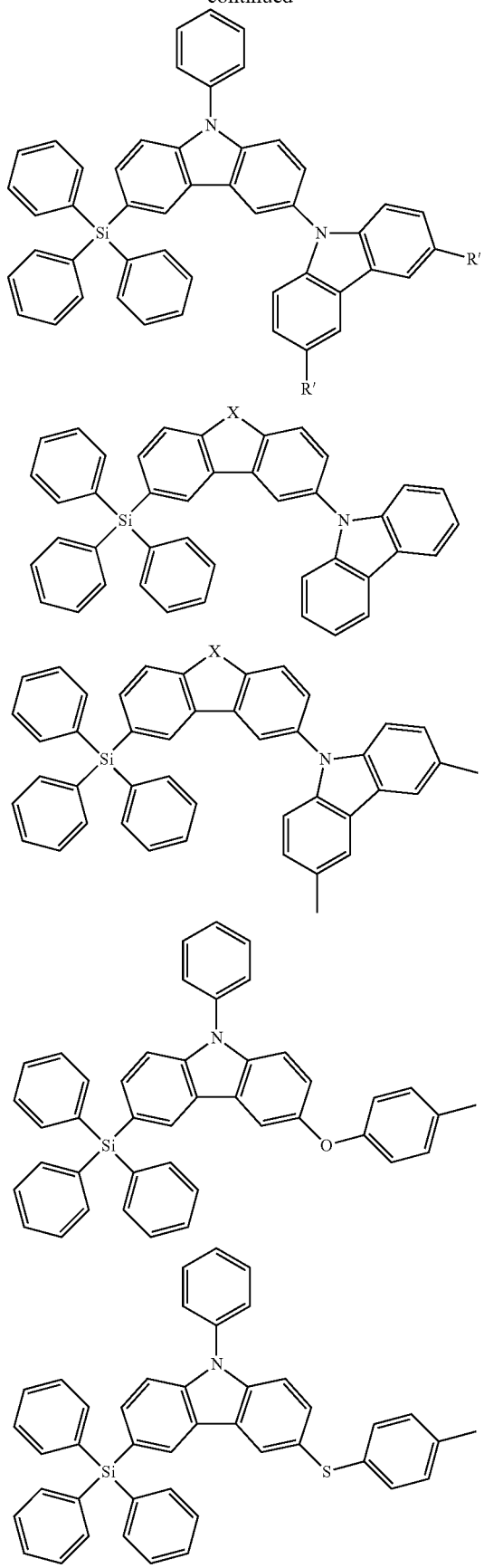

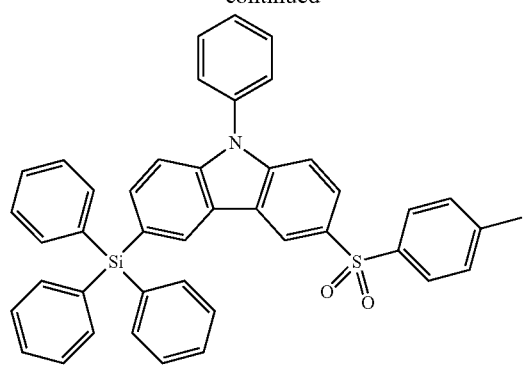
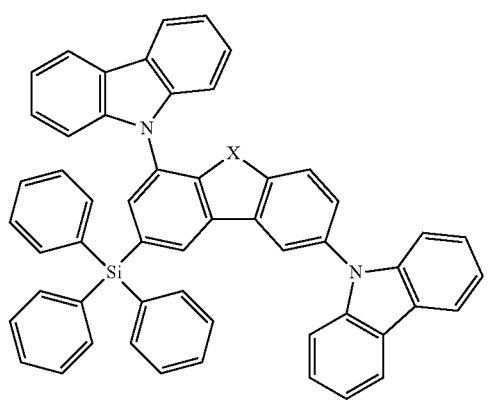
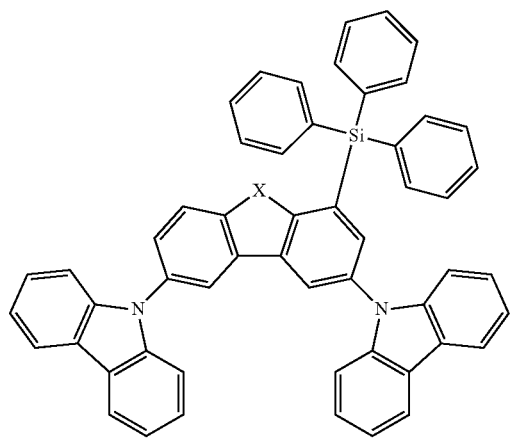
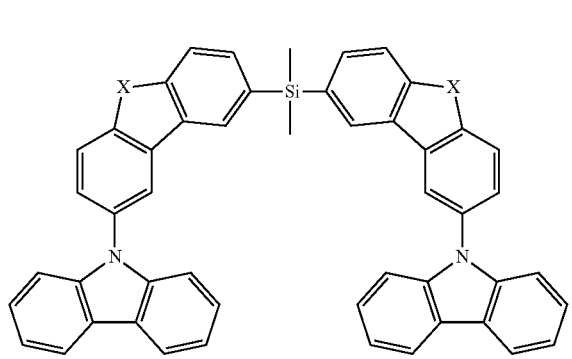
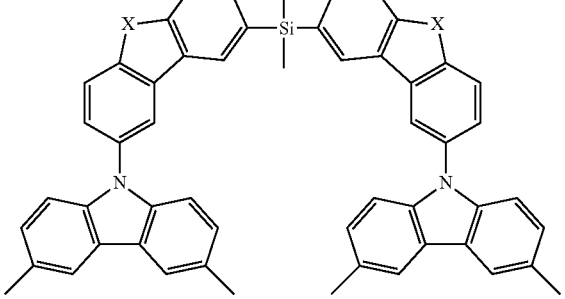
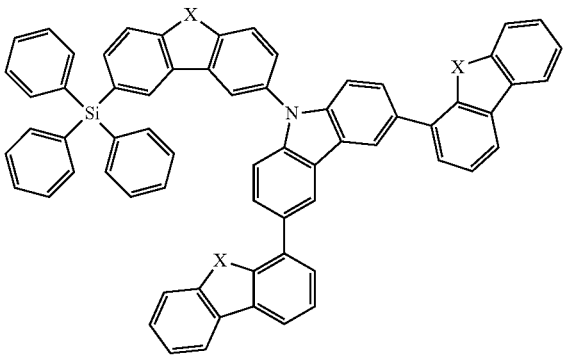

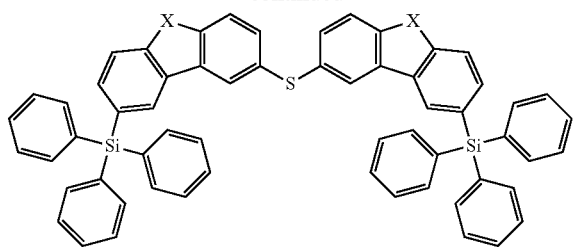
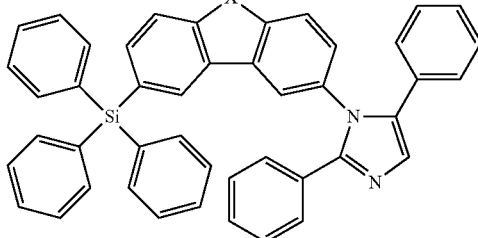
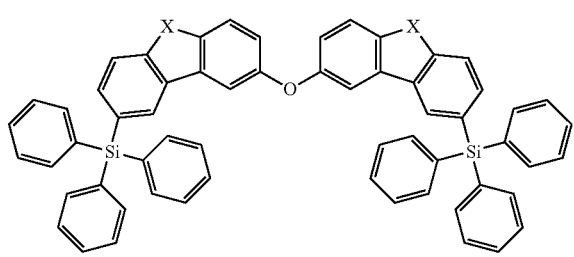
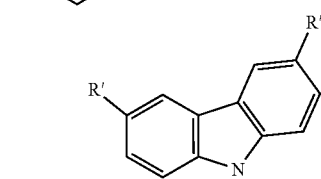
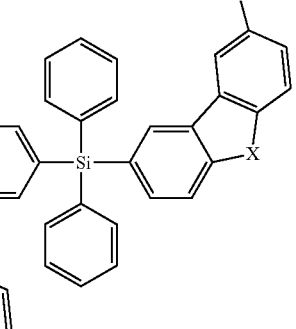
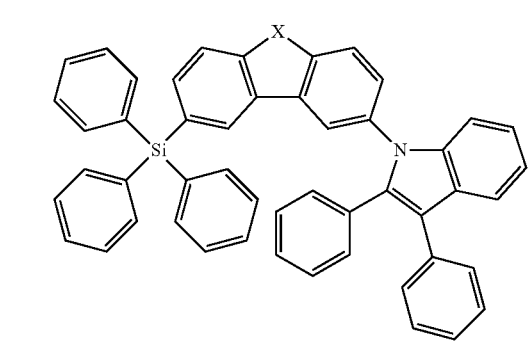
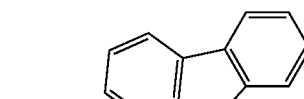
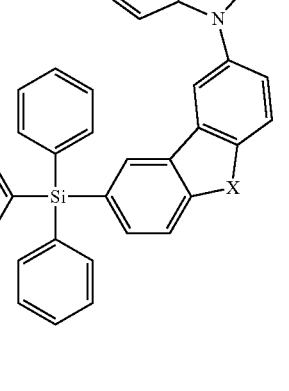
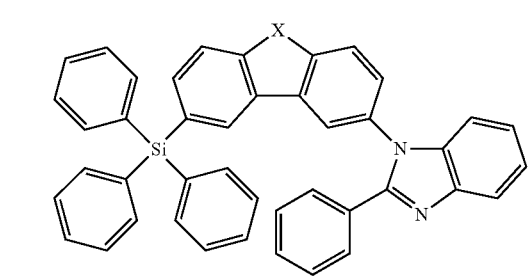
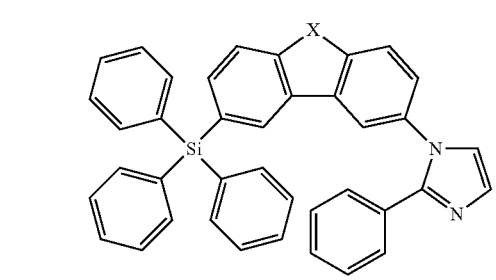
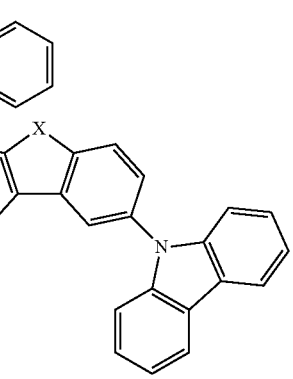

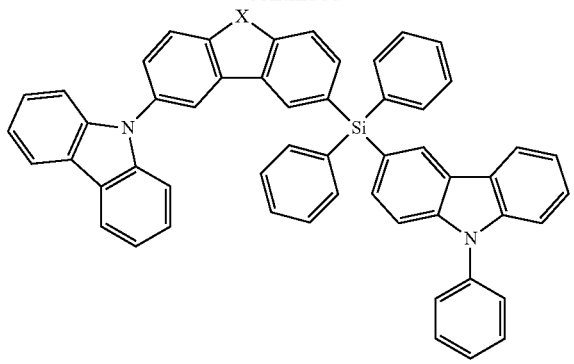
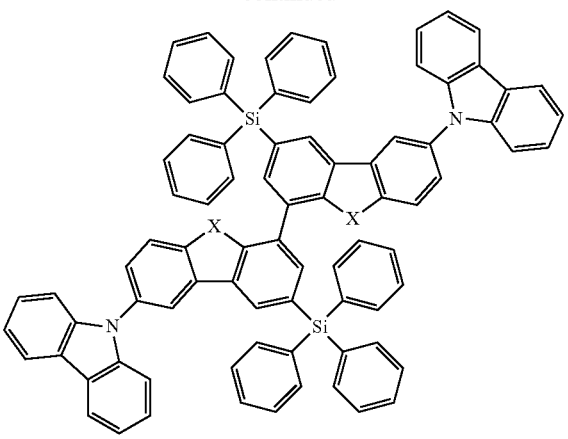
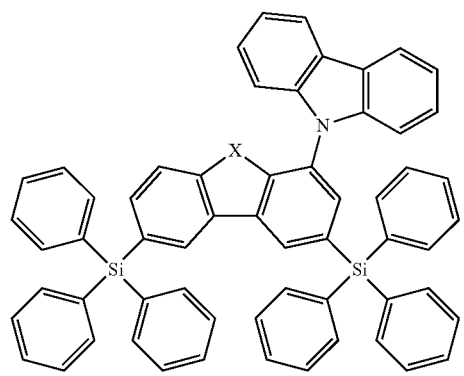
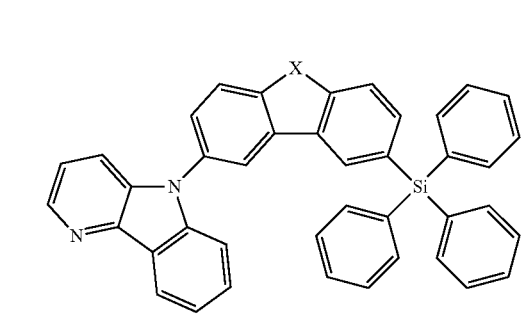
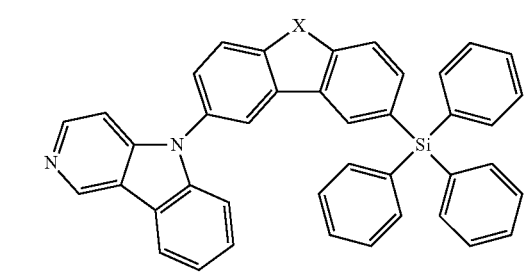
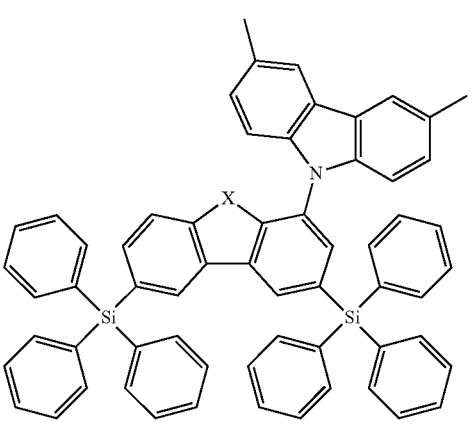
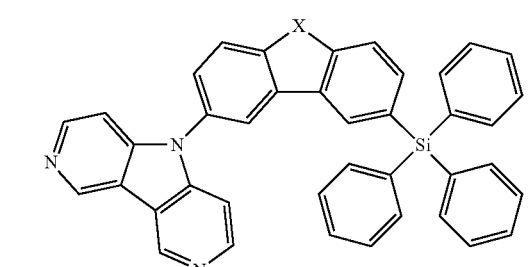
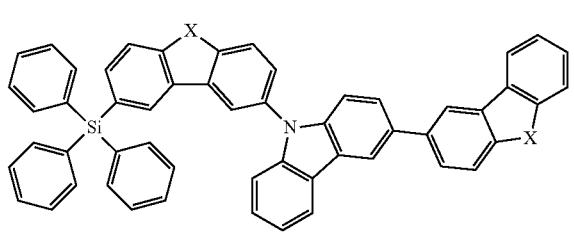
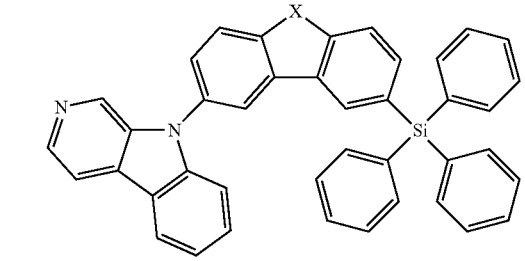

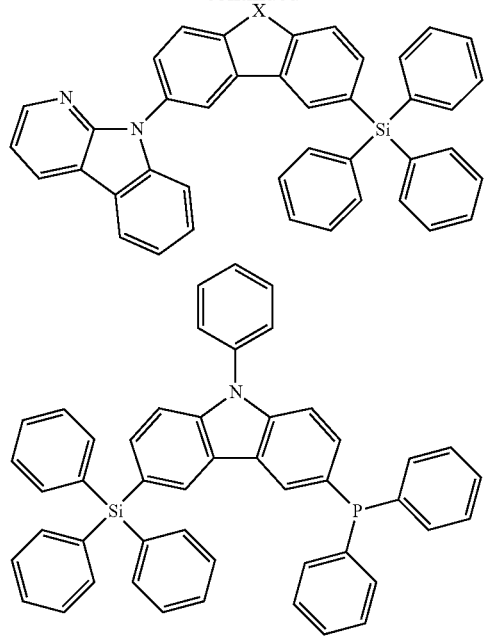
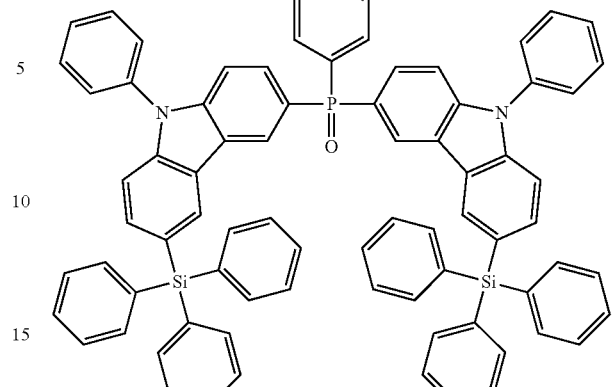
in which:
X is S or O, and
R' is H or CH$_3$.
Further particularly suitable compounds of the general formula (I) or (I*) are:
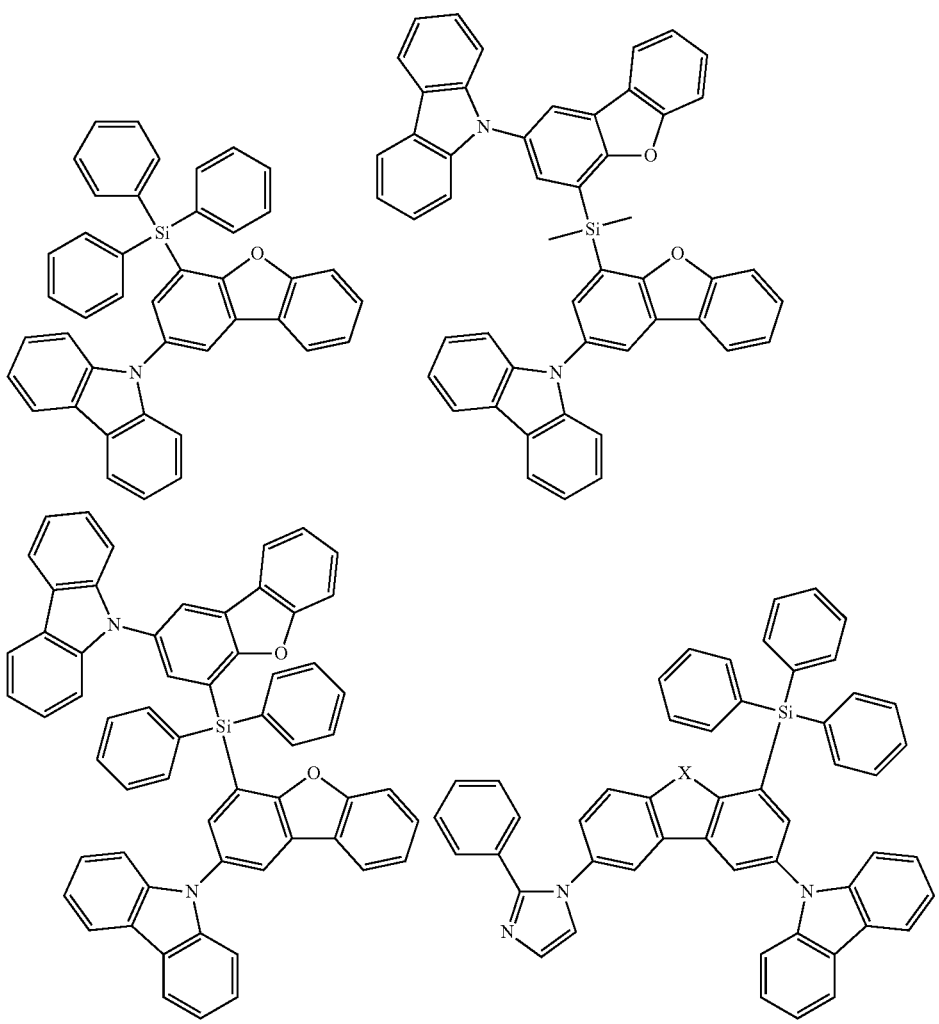

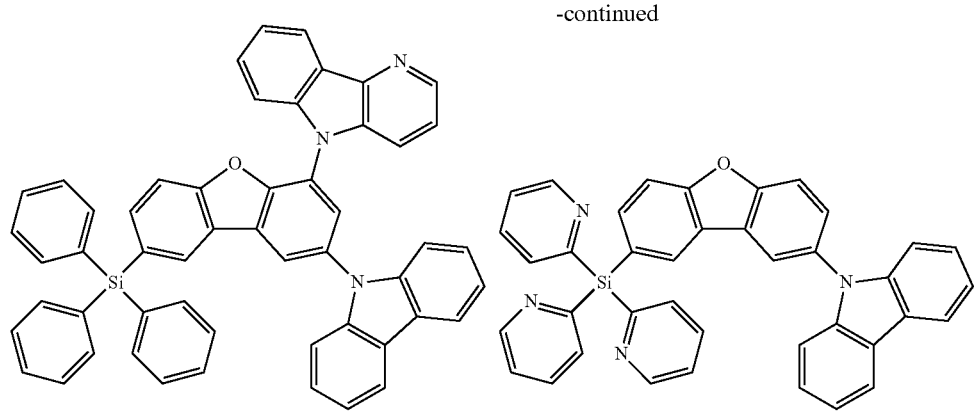
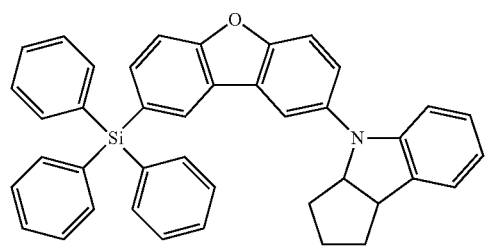
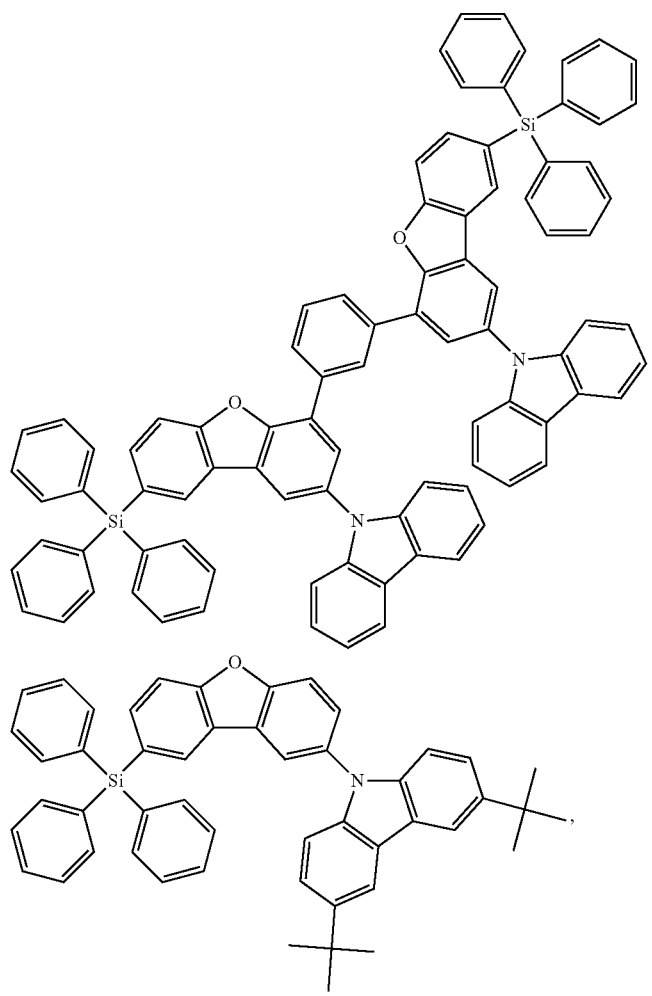

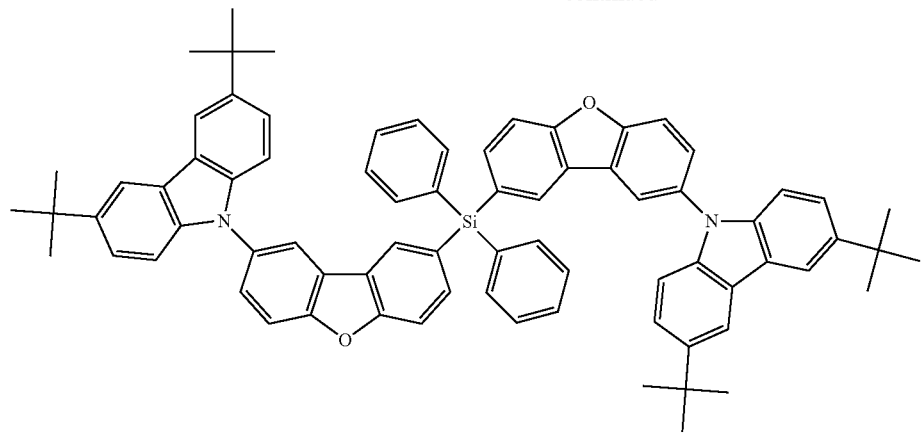
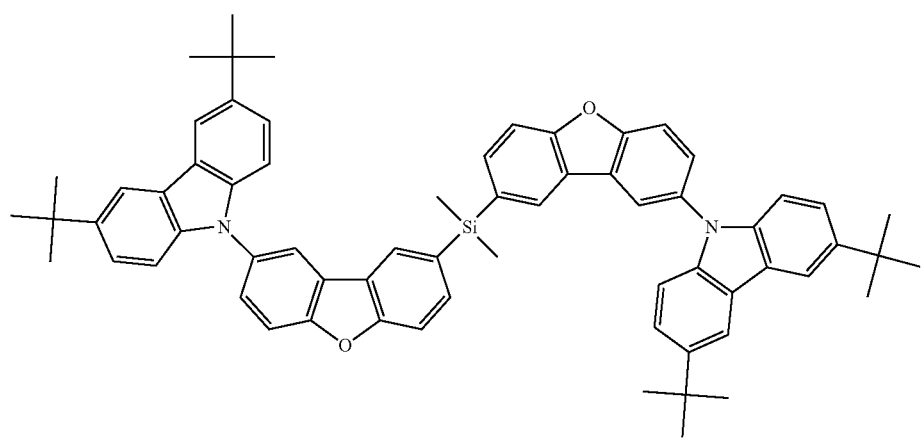
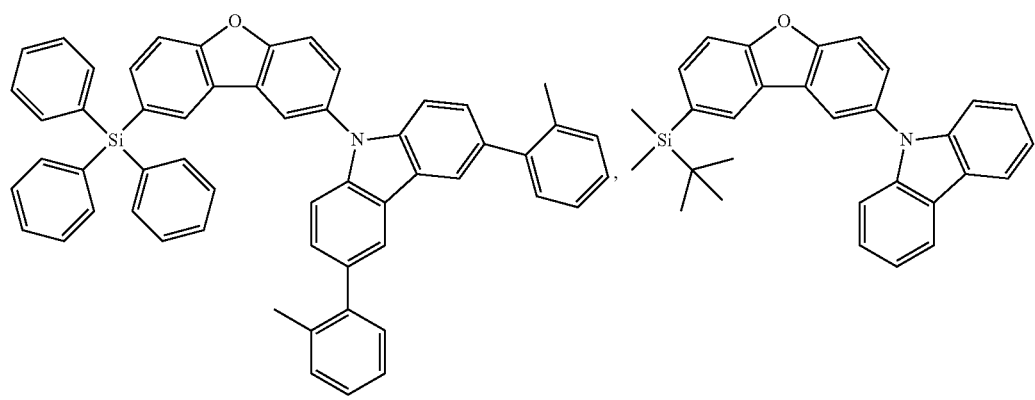
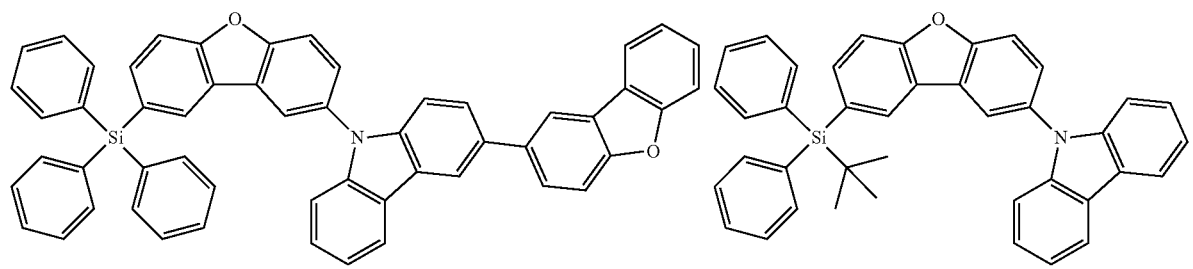

-continued
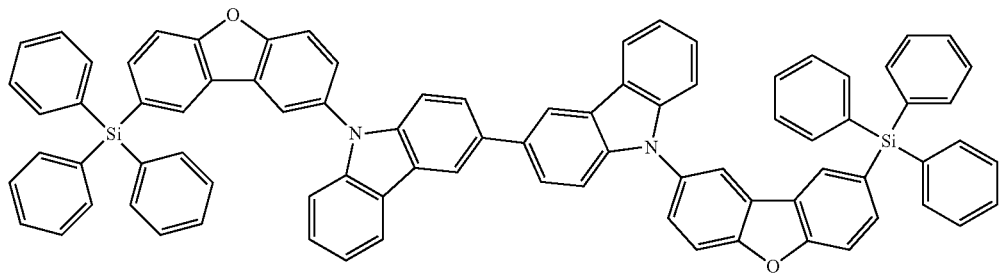
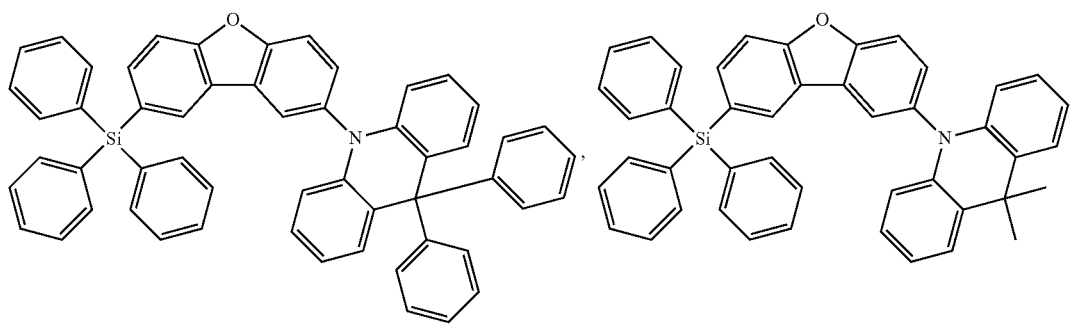
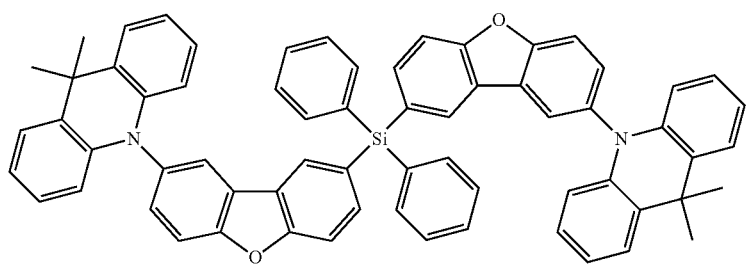
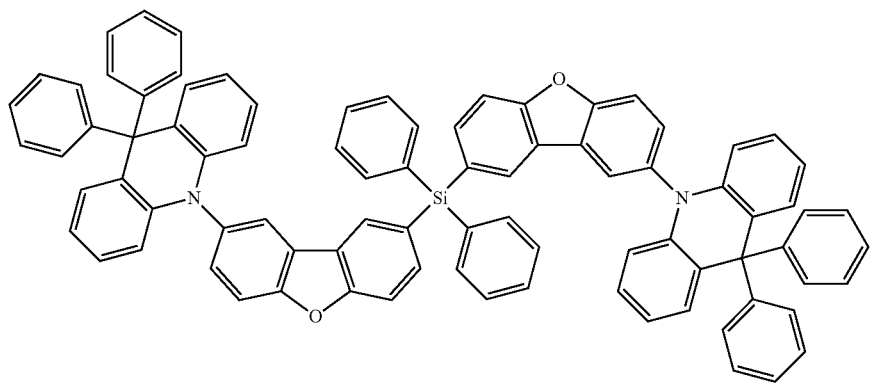
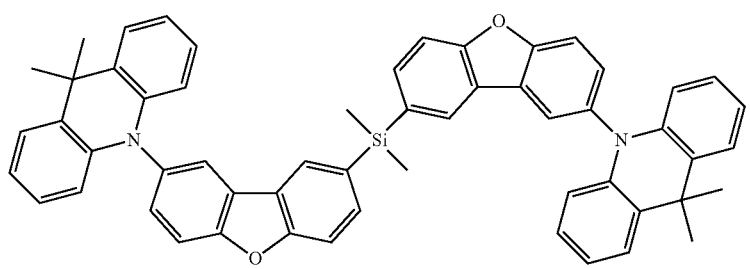

-continued
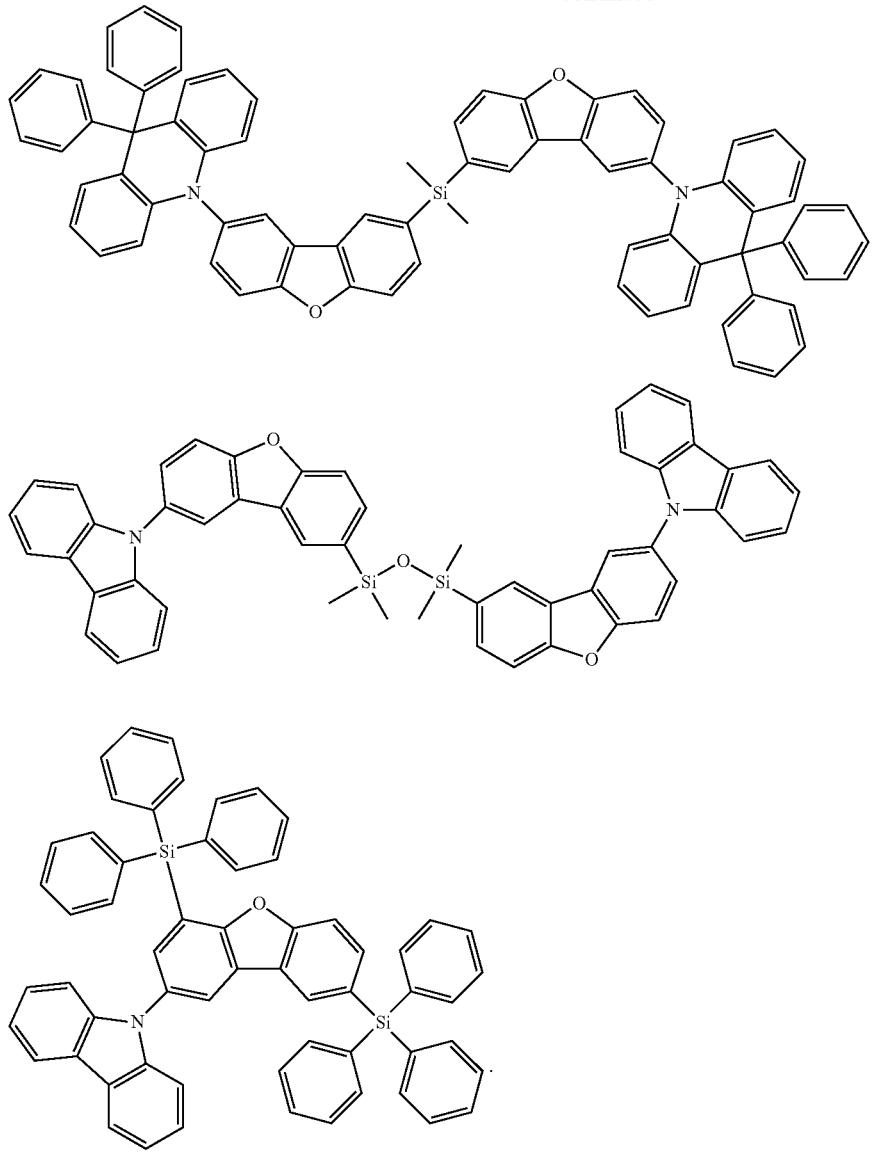
Further inventive compounds of the general formula (I) or (I*) correspond to the following formula (X):
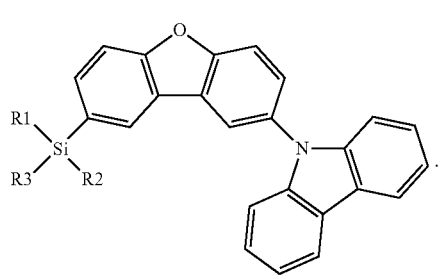
(X)
In the general formula (X), $R^1$, $R^2$, $R^3$ are each defined as follows:

| No | R1 | R2 | R3 |
| --- | --- | --- | --- |
| 35 | Methyl | Methyl | Ethyl |
| 36 | Methyl | Methyl | i-Propyl |
| 37 | Methyl | Methyl | n-Propyl |
| 38 | Methyl | Methyl | n-Butyl |
| 39 | Methyl | Methyl | i-Butyl |
| 40 | Methyl | Methyl | t-Butyl |
| 41 | Methyl | Methyl | n-Pentyl |
| 42 | Methyl | Methyl | n-Hexyl |
| 43 | Methyl | Methyl | —CH$_2$CH$_2$C(CH$_3$)$_3$ |
| 44 | Methyl | Methyl | n-C$_8$H$_{17}$ |
| 45 | Methyl | Methyl | i-C$_8$H$_{17}$ |
| 46 | Methyl | Methyl | n-C$_{10}$H$_{21}$ |
| 47 | Methyl | Methyl | n-C$_{12}$H$_{25}$ |
| 48 | Methyl | Methyl | n-C$_{18}$H$_{37}$ |
| 49 | Methyl | Methyl | n-C$_{30}$H$_{61}$ |
| 50 | Methyl | Methyl | Cyclohexyl |
| 51 | Methyl | Methyl | C(CH$_3$)$_2$Ph |
| 52 | Methyl | Methyl | —C(CH$_3$)$_2$CH(CH$_3$)$_2$ |
| 53 | Methyl | Methyl | —CCH$_2$CH(CH$_3$)(C$_2$H$_5$) |
| 54 | Methyl | Methyl | —CH$_2$CH(C$_{10}$H$_{21}$)$_2$ |
| 55 | Methyl | Methyl | —CH$_2$CH(C$_{12}$H$_{25}$)$_2$ |
| 56 | Methyl | Methyl | —CH$_2$CH$_2$(C$_3$F$_6$)CF$_3$ |
| 57 | Methyl | Methyl | —CH$_2$CH$_2$(C$_7$F$_{14}$)CF$_3$ |
| 58 | Methyl | Methyl | —CH$_2$CH$_2$(C$_5$F$_{10}$)CF$_3$ |
| 59 | Methyl | Methyl | —CH$_2$CH$_2$CF$_3$ |
| 60 | Methyl | Methyl | Phenyl |
| 61 | Methyl | Methyl | 2-Biphenyl |
| 62 | Methyl | Methyl | p-Tolyl |
| 63 | Methyl | Methyl | C$_6$F$_5$ |
| 64 | Methyl | Methyl | 3,5-(CF$_3$)$_2$Phenyl |
| 65 | Methyl | Methyl | —CH$_2$C(CH$_3$)$_2$Phenyl |
| 66 | Methyl | Methyl | 9-Fluorenyl |
| 67 | Methyl | Methyl | 3,6-Di(tert-butyl)-9-Fluorenyl |
| 15 | Methyl | Methyl | R5 |
| 68 | Methyl | Methyl | —OMe |
| 69 | Methyl | Methyl | —OEt |
| 70 | Methyl | Methyl | 2,4,6-t-Butylphenoxy |
| 71 | Methyl | Methyl | —O-tBu (tert-Butoxy) |
| 72 | Methyl | Methyl | —OSiEt$_3$ |
| 73 | Methyl | Ethyl | Ethyl |
| 74 | Methyl | Ethyl | Phenyl |
| 75 | Methyl | Ethyl | R5 |
| 76 | Methyl | n-Propyl | n-Propyl |
| 77 | Methyl | n-Propyl | Phenyl |
| 78 | Methyl | n-Propyl | R5 |
| 79 | Methyl | i-Propyl | i-Propyl |
| 80 | Methyl | i-Propyl | Phenyl |
| 81 | Methyl | i-Propyl | R5 |
| 82 | Methyl | n-Butyl | n-Butyl |
| 83 | Methyl | n-Butyl | Phenyl |
| 84 | Methyl | n-Butyl | R5 |
| 85 | Methyl | i-Butyl | i-Butyl |
| 86 | Methyl | i-Butyl | Phenyl |
| 87 | Methyl | i-Butyl | R5 |
| 88 | Methyl | t-Butyl | t-Butyl |
| 89 | Methyl | t-Butyl | Phenyl |
| 90 | Methyl | t-Butyl | R5 |
| 91 | Methyl | n-Pentyl | n-Pentyl |
| 92 | Methyl | n-Pentyl | n-Hexyl |
| 93 | Methyl | n-Pentyl | Phenyl |
| 94 | Methyl | n-Pentyl | R5 |
| 95 | Methyl | n-Hexyl | Hexyl |
| 96 | Methyl | n-Hexyl | Phenyl |
| 97 | Methyl | n-Hexyl | R5 |
| 98 | Methyl | n-Heptyl | R5 |
| 99 | Methyl | n-Octyl | R5 |
| 100 | Methyl | n-Decyl | R5 |
| 101 | Methyl | n-C$_{12}$H$_{25}$ | R5 |
| 102 | Methyl | n-C$_{18}$H$_{37}$ | R5 |
| 103 | Methyl | n-C$_{22}$H$_{45}$ | R5 |
| 104 | Methyl | n-C$_{30}$H$_{61}$ | R5 |
| 105 | Methyl | Cyclopentyl | Cyclopentyl |
| 106 | Methyl | Cyclopentyl | Phenyl |
| 107 | Methyl | Cyclopentyl | R5 |
| 108 | Methyl | Cyclohexyl | Cyclohexyl |
| 109 | Methyl | Cyclohexyl | Phenyl |
| 110 | Methyl | Cyclohexyl | R5 |
| 111 | Methyl | —CF$_2$CHF$_2$ | R5 |
| 112 | Methyl | —CH$_2$CH$_2$CF$_3$ | R5 |

-continued

| No | R1 | R2 | R3 |
|---|---|---|---|
| 113 | Methyl | —CH$_2$CH$_2$(CF$_2$)$_3$CF$_3$ | R5 |
| 114 | Methyl | —CH$_2$CH$_2$(CF$_2$)$_5$CF$_3$ | R5 |
| 115 | Methyl | —CH$_2$CH$_2$(CF$_2$)$_7$CF$_3$ | R5 |
| 116 | Methyl | Phenyl | Phenyl |
| 117 | Methyl | Phenyl | p-Tolyl |
| 118 | Methyl | Phenyl | Mesityl |
| 119 | Methyl | Phenyl | R5 |
| 120 | Methyl | p-Tolyl | p-Tolyl |
| 121 | Methyl | p-Tolyl | R5 |
| 122 | Methyl | Mesityl | Mesityl |
| 123 | Methyl | Mesityl | R5 |
| 124 | Methyl | R5 | R5 |
| 125 | Methyl | Methoxy | Methoxy |
| 126 | Methyl | Ethoxy | Ethoxy |
| 127 | Methyl | —OSiEt$_3$ | —OSiEt$_3$ |
| 128 | Methyl | —O—SiMe$_2$—CH$_2$CH$_2$(CF$_2$)$_4$CF$_3$ | —O—SiMe$_2$—CH$_2$CH$_2$(CF$_2$)$_4$CF$_3$ |
| 129 | Ethyl | Ethyl | Ethyl |
| 130 | Ethyl | Ethyl | n-Propyl |
| 131 | Ethyl | Ethyl | i-Propyl |
| 132 | Ethyl | Ethyl | n-Butyl |
| 133 | Ethyl | Ethyl | i-Butyl |
| 134 | Ethyl | Ethyl | t-Butyl |
| 135 | Ethyl | Ethyl | Phenyl |
| 136 | Ethyl | Ethyl | R5 |
| 137 | Ethyl | Phenyl | Phenyl |
| 138 | Ethyl | Phenyl | R5 |
| 139 | Ethyl | R5 | R5 |
| 140 | Ethyl | Ethoxy | Ethoxy |
| 141 | n-Propyl | n-Propyl | n-Propyl |
| 142 | n-Propyl | n-Propyl | Phenyl |
| 143 | n-Propyl | n-Propyl | R5 |
| 144 | n-Propyl | Phenyl | Phenyl |
| 145 | n-Propyl | Phenyl | R5 |
| 146 | n-Propyl | R5 | R5 |
| 147 | i-Propyl | i-Propyl | i-Propyl |
| 148 | i-Propyl | i-Propyl | Phenyl |
| 149 | i-Propyl | i-Propyl | R5 |
| 150 | i-Propyl | i-Propyl | 2-Biphenyl |
| 151 | i-Propyl | i-Propyl | Ethoxy |
| 152 | i-Propyl | Phenyl | Phenyl |
| 153 | i-Propyl | Phenyl | R5 |
| 154 | i-Propyl | R5 | R5 |
| 155 | n-Butyl | n-Butyl | n-Butyl |
| 156 | n-Butyl | n-Butyl | Phenyl |
| 157 | n-Butyl | n-Butyl | R5 |
| 158 | n-Butyl | n-Hexyl | R5 |
| 159 | n-Butyl | Phenyl | Phenyl |
| 160 | n-Butyl | Phenyl | R5 |
| 161 | n-Butyl | R5 | R5 |
| 162 | sec-Butyl | sec-Butyl | sec-Butyl |
| 163 | sec-Butyl | sec-Butyl | Phenyl |
| 164 | sec-Butyl | sec-Butyl | R5 |
| 165 | sec-Butyl | Phenyl | Phenyl |
| 166 | sec-Butyl | Phenyl | R5 |
| 167 | sec-Butyl | R5 | R5 |
| 168 | i-Butyl | i-Butyl | i-Butyl |
| 169 | i-Butyl | i-Butyl | n-C$_8$H$_{17}$ |
| 170 | i-Butyl | i-Butyl | n-C$_{18}$H$_{37}$ |
| 171 | i-Butyl | i-Butyl | Phenyl |
| 172 | i-Butyl | i-Butyl | R5 |
| 173 | i-Butyl | Phenyl | Phenyl |
| 174 | i-Butyl | Phenyl | R5 |
| 175 | i-Butyl | R5 | R5 |
| 176 | t-Butyl | t-Butyl | t-Butyl |
| 177 | t-Butyl | t-Butyl | n-C$_8$H$_{17}$ |
| 178 | t-Butyl | t-Butyl | Phenyl |
| 179 | t-Butyl | t-Butyl | R5 |
| 180 | t-Butyl | Phenyl | Phenyl |
| 181 | t-Butyl | Phenyl | R5 |
| 182 | t-Butyl | R5 | R5 |
| 183 | n-Pentyl | n-Pentyl | n-Pentyl |
| 184 | n-Pentyl | n-Pentyl | Phenyl |
| 185 | n-Pentyl | n-Pentyl | R5 |
| 186 | n-Pentyl | Phenyl | Phenyl |

-continued

| No | R1 | R2 | R3 |
|---|---|---|---|
| 187 | n-Pentyl | Phenyl | R5 |
| 188 | n-Pentyl | R5 | R5 |
| 189 | Cyclopentyl | Cyclopentyl | Cyclopentyl |
| 190 | Cyclopentyl | Cyclopentyl | Phenyl |
| 191 | Cyclopentyl | Cyclopentyl | R5 |
| 192 | Cyclopentyl | Phenyl | Phenyl |
| 193 | Cyclopentyl | Phenyl | R5 |
| 194 | Cyclopentyl | R5 | R5 |
| 195 | n-Hexyl | n-Hexyl | n-Hexyl |
| 196 | n-Hexyl | n-Hexyl | Phenyl |
| 197 | n-Hexyl | n-Hexyl | R5 |
| 198 | n-Hexyl | Phenyl | Phenyl |
| 199 | n-Hexyl | Phenyl | R5 |
| 200 | n-Hexyl | R5 | R5 |
| 201 | —$CH_2CH_2C(CH_3)_3$ | —$CH_2CH_2C(CH_3)_3$ | —$CH_2CH_2C(CH_3)_3$ |
| 202 | —$CH_2CH_2C(CH_3)_3$ | —$CH_2CH_2C(CH_3)_3$ | R5 |
| 203 | —$CH_2CH_2C(CH_3)_3$ | R5 | R5 |
| 204 | t-Hexyl | t-Hexyl | t-Hexyl |
| 205 | t-Hexyl | t-Hexyl | R5 |
| 206 | t-Hexyl | R5 | R5 |
| 207 | n-Heptyl | n-Heptyl | n-Heptyl |
| 208 | n-Heptyl | n-Heptyl | R5 |
| 209 | n-Heptyl | R5 | R5 |
| 210 | n-Octyl | n-Octyl | n-Octyl |
| 211 | n-Octyl | n-Octyl | R5 |
| 212 | n-Octyl | R5 | R5 |
| 213 | i-Octyl | i-Octyl | i-Octyl |
| 214 | i-Octyl | i-Octyl | R5 |
| 215 | i-Octyl | R5 | R5 |
| 216 | n-Nonyl | n-Nonyl | n-Nonyl |
| 217 | n-Nonyl | n-Nonyl | R5 |
| 218 | n-Nonyl | R5 | R5 |
| 219 | Cyclohexyl | Cyclohexyl | Cyclohexyl |
| 220 | Cyclohexyl | Cyclohexyl | R5 |
| 221 | Cyclohexyl | R5 | R5 |
| 222 | Cyclooctyl | Cyclooctyl | Cyclooctyl |
| 223 | Cyclooctyl | Cyclooctyl | R5 |
| 224 | Cyclooctyl | R5 | R5 |
| 225 | n-$C_{10}H_{21}$ | n-$C_{10}H_{21}$ | n-$C_{10}H_{21}$ |
| 226 | n-$C_{10}H_{21}$ | n-$C_{10}H_{21}$ | R5 |
| 227 | n-$C_{10}H_{21}$ | R5 | R5 |
| 228 | n-$C_{11}H_{23}$ | n-$C_{11}H_{23}$ | n-$C_{11}H_{23}$ |
| 229 | n-$C_{11}H_{23}$ | n-$C_{11}H_{23}$ | R5 |
| 230 | n-$C_{11}H_{23}$ | R5 | R5 |
| 231 | n-$C_{12}H_{25}$ | n-$C_{12}H_{25}$ | n-$C_{12}H_{25}$ |
| 232 | n-$C_{12}H_{25}$ | n-$C_{12}H_{25}$ | R5 |
| 233 | n-$C_{12}H_{25}$ | R5 | R5 |
| 234 | n-$C_{14}H_{29}$ | n-$C_{14}H_{29}$ | n-$C_{14}H_{29}$ |
| 235 | n-$C_{14}H_{29}$ | n-$C_{14}H_{29}$ | R5 |
| 236 | n-$C_{14}H_{29}$ | R5 | R5 |
| 237 | n-$C_{16}H_{33}$ | n-$C_{16}H_{33}$ | n-$C_{16}H_{33}$ |
| 238 | n-$C_{16}H_{33}$ | n-$C_{16}H_{33}$ | R5 |
| 239 | n-$C_{16}H_{33}$ | R5 | R5 |
| 240 | n-$C_{18}H_{37}$ | n-$C_{18}H_{37}$ | R5 |
| 241 | n-$C_{18}H_{37}$ | R5 | R5 |
| 242 | n-$C_{18}H_{37}$ | OEt | OEt |
| 243 | n-$C_{18}H_{37}$ | R5 | OMe |
| 244 | n-$C_{20}H_{41}$ | n-$C_{20}H_{41}$ | n-$C_{20}H_{41}$ |
| 245 | n-$C_{20}H_{41}$ | n-$C_{20}H_{41}$ | R5 |
| 246 | n-$C_{20}H_{41}$ | R5 | R5 |
| 247 | n-$C_{22}H_{45}$ | n-$C_{22}H_{45}$ | n-$C_{22}H_{45}$ |
| 248 | n-$C_{22}H_{45}$ | n-$C_{22}H_{45}$ | R5 |
| 249 | n-$C_{22}H_{45}$ | R5 | R5 |
| 250 | n-$C_{26}H_{53}$ | n-$C_{26}H_{53}$ | n-$C_{26}H_{53}$ |
| 251 | n-$C_{26}H_{53}$ | n-$C_{26}H_{53}$ | R5 |
| 252 | n-$C_{26}H_{53}$ | R5 | R5 |
| 253 | n-$C_{30}H_{61}$ | n-$C_{30}H_{61}$ | n-$C_{30}H_{61}$ |
| 254 | n-$C_{30}H_{61}$ | n-$C_{30}H_{61}$ | R5 |
| 255 | n-$C_{30}H_{61}$ | R5 | R5 |
| 256 | —$CH_2$-Cyclohexyl | —$CH_2$-Cyclohexyl | R5 |
| 257 | —$CH_2CH_2CF_3$ | —$CH_2CH_2CF_3$ | —$CH_2CH_2CF_3$ |

-continued

| No | R1 | R2 | R3 |
|---|---|---|---|
| 258 | —CH₂CH₂CF₃ | —CH₂CH₂CF₃ | R5 |
| 259 | —CH₂CH₂CF₃ | R5 | R5 |
| 260 | —CH₂CH₂(CF₂)₃CF₃ | —CH₂CH₂(CF₂)₃CF₃ | —CH₂CH₂(CF₂)₃CF₃ |
| 261 | —CH₂CH₂(CF₂)₃CF₃ | —CH₂CH₂(CF₂)₃CF₃ | R5 |
| 262 | —CH₂CH₂(CF₂)₃CF₃ | R5 | R5 |
| 263 | —CH₂CH₂(CF₂)₅CF₃ | —CH₂CH₂(CF₂)₅CF₃ | —CH₂CH₂(CF₂)₅CF₃ |
| 264 | —CH₂CH₂(CF₂)₅CF₃ | —CH₂CH₂(CF₂)₅CF₃ | R5 |
| 265 | —CH₂CH₂(CF₂)₅CF₃ | R5 | R5 |
| 266 | —CH₂CH₂(CF₂)₇CF₃ | —CH₂CH₂(CF₂)₇CF₃ | —CH₂CH₂(CF₂)₇CF₃ |
| 267 | —CH₂CH₂(CF₂)₇CF₃ | —CH₂CH₂(CF₂)₇CF₃ | R5 |
| 268 | —CH₂CH₂(CF₂)₇CF₃ | R5 | R5 |
| 269 | —CH₂CH₂(CF₂)₉CF₃ | —CH₂CH₂(CF₂)₉CF₃ | —CH₂CH₂(CF₂)₉CF₃ |
| 270 | —CH₂CH₂(CF₂)₉CF₃ | —CH₂CH₂(CF₂)₉CF₃ | R5 |
| 271 | —CH₂CH₂(CF₂)₉CF₃ | R5 | R5 |
| 272 | —CH₂CH₂(CF₂)₁₁CF₃ | —CH₂CH₂(CF₂)₁₁CF₃ | —CH₂CH₂(CF₂)₁₁CF₃ |
| 273 | —CH₂CH₂(CF₂)₁₁CF₃ | —CH₂CH₂(CF₂)₁₁CF₃ | R5 |
| 274 | —CH₂CH₂(CF₂)₁₁CF₃ | R5 | R5 |
| 275 | —CF₂CHF₂ | —CF₂CHF₂ | —CF₂CHF₂ |
| 276 | —CF₂CHF₂ | —CF₂CHF₂ | R5 |
| 277 | —CF₂CHF₂ | R5 | R5 |
| 278 | —(CF₂)₃CHF₂ | —(CF₂)₃CHF₂ | —(CF₂)₃CHF₂ |
| 279 | —(CF₂)₃CHF₂ | —(CF₂)₃CHF₂ | R5 |
| 280 | —(CF₂)₃CHF₂ | R5 | R5 |
| 14 | Phenyl | Phenyl | Phenyl |
| 281 | Phenyl | Phenyl | p-Tolyl |
| 282 | Phenyl | Phenyl | m-Tolyl |
| 283 | Phenyl | Phenyl | o-Tolyl |
| 284 | Phenyl | Phenyl | 2-Xylyl |
| 285 | Phenyl | Phenyl | 5-Xylyl |
| 286 | Phenyl | Phenyl | Mesityl |
| 287 | Phenyl | Phenyl | 9-Fluorenyl |
| 18 | Phenyl | Phenyl | R5 |
| 288 | Phenyl | Phenyl | —O-tBu (tert-Butoxy) |
| 289 | Phenyl | p-Tolyl | p-Tolyl |
| 290 | Phenyl | m-Tolyl | m-Tolyl |
| 291 | Phenyl | o-Tolyl | o-Tolyl |
| 292 | Phenyl | 2-Xylyl | 2-Xylyl |
| 293 | Phenyl | 5-Xylyl | 5-Xylyl |
| 294 | Phenyl | Mesityl | Mesityl |
| 295 | Phenyl | R5 | R5 |
| 296 | Phenyl | Ethoxy | Ethoxy |
| 297 | p-Tolyl | p-Tolyl | p-Tolyl |
| 298 | p-Tolyl | p-Tolyl | R5 |
| 299 | p-Tolyl | R5 | R5 |
| 300 | m-Tolyl | m-Tolyl | m-Tolyl |
| 301 | m-Tolyl | m-Tolyl | R5 |
| 302 | o-Tolyl | o-Tolyl | o-Tolyl |
| 303 | o-Tolyl | o-Tolyl | R5 |
| 304 | 2-Xylyl | 2-Xylyl | 2-Xylyl |
| 305 | 2-Xylyl | 2-Xylyl | R5 |
| 306 | 5-Xylyl | 5-Xylyl | 5-Xylyl |
| 307 | 5-Xylyl | 5-Xylyl | R5 |
| 308 | Mesityl | Mesityl | Mesityl |
| 309 | Mesityl | Mesityl | R5 |
| 310 | C₆F₅ | C₆F₅ | C₆F₅ |
| 311 | C₆F₅ | C₆F₅ | R5 |
| 312 | C₆F₅ | R5 | R5 |
| 313 | R5 | R5 | R5 |
| 314 | R5 | Ethoxy | Ethoxy |
| 315 | R5 | n-Butoxy | n-Butoxy |
| 316 | R5 | R5 | Methoxy |
| 317 | R5 | R5 | Ethoxy |
| 318 | R5 | R5 | OSiMe₃ |
| 319 | R5 | R5 | —(CH₂)₁₁—(CH₂)₂OCH₃ |
| 320 | Methoxy | Methoxy | Methoxy |
| 321 | Ethoxy | Ethoxy | Ethoxy |
| 322 | i-Propoxy | i-Propoxy | i-Propoxy |
| 323 | t-Butoxy | t-Butoxy | t-Butoxy |
| 324 | OSiMe₃ | OSiMe₃ | OSiMe₃ |
| 325 |  | Cyclobutyl | Methyl |
| 326 |  | Cyclobutyl | R5 |
| 327 |  | Cyclobutyl | p-Methoxyphenyl |
| 328 |  | Cyclopentyl | Methyl |

-continued

| No | R1 | R2 | R3 |
|---|---|---|---|
| 329 |  | Cyclopentyl | R5 |
| 330 |  | Cyclohexyl | Methyl |
| 331 |  | Cyclohexyl | R5 |

In this table:

R5 = 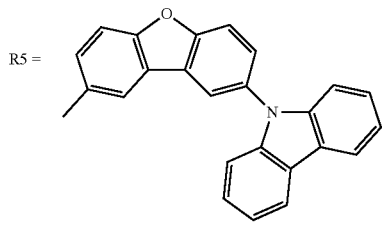 [SMILES: Cc1ccc2oc3ccc(-n4c5ccccc5c5ccccc54)cc3c2c1]

Particularly preferred inventive compounds in which two units of the general formula (I) and/or (I*) are bridged to one another via a linear or branched, saturated or unsaturated bridge optionally interrupted by at least one heteroatom or via O, where this bridge in the general formula (I) and/or (I*) is in each case attached to the silicon atoms instead of $R^2$, correspond to the general formula (XI)

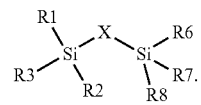 (XI)

In formula (XI), X, $R^1$, $R^2$, $R^3$, $R^5$, $R^6$, $R^7$ and $R^8$ are each defined as follows:

| No. | R1 | R2 | R3 | R6 | R7 | R8 | X |
|---|---|---|---|---|---|---|---|
| 332 | Methyl | R5 | R5 | Methyl | R5 | R5 | —CH$_2$— |
| 333 | Methyl | Methyl | R5 | Methyl | Methyl | R5 | —CH$_2$— |
| 334 | R5 | R5 | R5 | R5 | R5 | R5 | —CH$_2$— |
| 335 | Methyl | R5 | R5 | Methyl | R5 | R5 | —C$_2$H$_4$— |
| 336 | Methyl | Methyl | R5 | Methyl | Methyl | R5 | —C$_2$H$_4$— |
| 337 | R5 | R5 | R5 | R5 | R5 | R5 | —C$_2$H$_4$— |
| 338 | Methyl | R5 | R5 | Methyl | R5 | R5 | —C$_3$H$_6$— |
| 339 | Methyl | Methyl | R5 | Methyl | Methyl | R5 | —C$_3$H$_6$— |
| 340 | R5 | R5 | R5 | R5 | R5 | R5 | —C$_3$H$_6$— |
| 341 | Methyl | R5 | R5 | Methyl | R5 | R5 | —C$_4$H$_8$— |
| 342 | Methyl | Methyl | R5 | Methyl | Methyl | R5 | —C$_4$H$_8$— |
| 343 | R5 | R5 | R5 | R5 | R5 | R5 | —C$_4$H$_8$— |
| 344 | Methyl | R5 | R5 | Methyl | R5 | R5 | —C$_6$H$_{12}$— |
| 345 | Methyl | Methyl | R5 | Methyl | Methyl | R5 | —C$_6$H$_{12}$— |
| 346 | R5 | R5 | R5 | R5 | R5 | R5 | —C$_6$H$_{12}$— |
| 347 | Methyl | R5 | R5 | Methyl | R5 | R5 | —C$_8$H$_{16}$— |
| 348 | Methyl | Methyl | R5 | Methyl | Methyl | R5 | —C$_8$H$_{16}$— |
| 349 | R5 | R5 | R5 | R5 | R5 | R5 | —C$_8$H$_{16}$— |
| 350 | Methyl | R5 | R5 | Methyl | R5 | R5 | —C$_9$H$_{18}$— |
| 351 | Methyl | Methyl | R5 | Methyl | Methyl | R5 | —C$_9$H$_{18}$— |
| 352 | R5 | R5 | R5 | R5 | R5 | R5 | —C$_9$H$_{18}$— |
| 353 | R5 | R5 | R5 | R5 | R5 | R5 | —CH(C$_8$H$_{17}$)CH$_2$— |
| 354 | Methyl | R5 | R5 | Methyl | R5 | R5 | —C$_2$H$_4$(CF$_2$)$_8$C$_2$H$_4$— |
| 355 | Methyl | Methyl | R5 | Methyl | Methyl | R5 | —C$_2$H$_4$(CF$_2$)$_8$C$_2$H$_4$— |
| 356 | R5 | R5 | R5 | R5 | R5 | R5 | —C$_2$H$_4$(CF$_2$)$_8$C$_2$H$_4$— |
| 357 | Methyl | R5 | R5 | Methyl | R5 | R5 | —C≡C— |
| 358 | Methyl | Methyl | R5 | Methyl | Methyl | R5 | —C≡C— |
| 359 | R5 | R5 | R5 | R5 | R5 | R5 | —C≡C— |
| 360 | Methyl | R5 | R5 | Methyl | R5 | R5 | -1,4-(CH$_2$)$_2$-Phenyl-(CH$_2$)$_2$— |
| 361 | Methyl | Methyl | R5 | Methyl | Methyl | R5 | -1,4-(CH$_2$)$_2$-Phenyl-(CH$_2$)$_2$— |
| 362 | R5 | R5 | R5 | R5 | R5 | R5 | -1,4-(CH$_2$)$_2$-Phenyl-(CH$_2$)$_2$— |
| 363 | Methyl | R5 | R5 | Methyl | R5 | R5 | -1,3-(CH$_2$)$_2$-Phenyl-(CH$_2$)$_2$— |
| 364 | Methyl | Methyl | R5 | Methyl | Methyl | R5 | -1,3-(CH$_2$)$_2$-Phenyl-(CH$_2$)$_2$— |
| 365 | R5 | R5 | R5 | R5 | R5 | R5 | -1,3-(CH$_2$)$_2$-Phenyl-(CH$_2$)$_2$— |
| 366 | Methyl | R5 | R5 | Methyl | R5 | R5 | -1,4-(CH$_2$)$_3$-Phenyl-(CH$_2$)$_3$— |
| 367 | Methyl | Methyl | R5 | Methyl | Methyl | R5 | -1,4-(CH$_2$)$_3$-Phenyl-(CH$_2$)$_3$— |
| 368 | R5 | R5 | R5 | R5 | R5 | R5 | -1,4-(CH$_2$)$_3$-Phenyl-(CH$_2$)$_3$— |
| 369 | Methyl | R5 | R5 | Methyl | R5 | R5 | -1,3-(CH$_2$)$_3$-Phenyl-(CH$_2$)$_3$— |
| 370 | Methyl | Methyl | R5 | Methyl | Methyl | R5 | -1,3-(CH$_2$)$_3$-Phenyl-(CH$_2$)$_3$— |
| 371 | R5 | R5 | R5 | R5 | R5 | R5 | -1,3-(CH$_2$)$_3$-Phenyl-(CH$_2$)$_3$— |
| 372 | Methyl | R5 | R5 | Methyl | R5 | R5 | -1,4-Phenyl- |
| 373 | Methyl | Methyl | R5 | Methyl | Methyl | R5 | -1,4-Phenyl- |
| 374 | R5 | R5 | R5 | R5 | R5 | R5 | -1,4-Phenyl- |
| 375 | Methyl | R5 | R5 | Methyl | R5 | R5 | -1,3-Phenyl- |

-continued

| No. | R1 | R2 | R3 | R6 | R7 | R8 | X |
|---|---|---|---|---|---|---|---|
| 376 | Methyl | Methyl | R5 | Methyl | Methyl | R5 | -1,3-Phenyl- |
| 377 | R5 | R5 | R5 | R5 | R5 | R5 | -1,3-Phenyl- |
| 28 | Methyl | Methyl | R5 | Methyl | Methyl | R5 | —O— |
| 378 | Methyl | R5 | R5 | Methyl | R5 | R5 | —O— |
| 379 | Methyl | Methyl | R5 | Methyl | Methyl | R5 | —O—Si(CH$_3$)$_2$—O— |
| 380 | Methyl | Methyl | R5 | Methyl | Methyl | R5 | —O—Si(CH$_3$)(Ph)—O— |
| 381 | Methyl | Methyl | R5 | Methyl | Methyl | R5 | —O—Si(CH$_3$)$_2$—O—Si(CH$_3$)$_2$—O— |
| 382 | Methyl | Methyl | R5 | Methyl | Methyl | R5 | —O—Si(CH$_3$)$_2$—O—Si(CH$_3$)$_2$—O—Si(CH$_3$)$_2$—O— |
| 383 | Methyl | —OSiMe$_3$ | R5 | Methyl | —OSiMe$_3$ | R5 | —O— |
| 384 | Methyl | Phenyl | R5 | Methyl | Phenyl | R5 | —O— |
| 385 | i-Propyl | i-Propyl | R5 | i-Propyl | i-Propyl | R5 | —O— |
| 386 | Cyclopentyl | Cyclopentyl | R5 | Cyclopentyl | Cyclopentyl | R5 | —O— |
| 387 | Phenyl | Phenyl | R5 | Phenyl | Phenyl | R5 | —O— |
| 388 | Phenyl | R5 | R5 | Phenyl | R5 | R5 | —O— |
| 389 | R5 | R5 | R5 | R5 | R5 | R5 | —O— |

In this table:

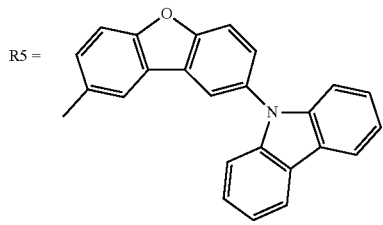 [SMILES: Cc1ccc2oc3ccc(-n4c5ccccc5c5ccccc54)cc3c2c1]

R5 =

Further examples: R are independently Me, phenyl or R5, where at least one R is R5:

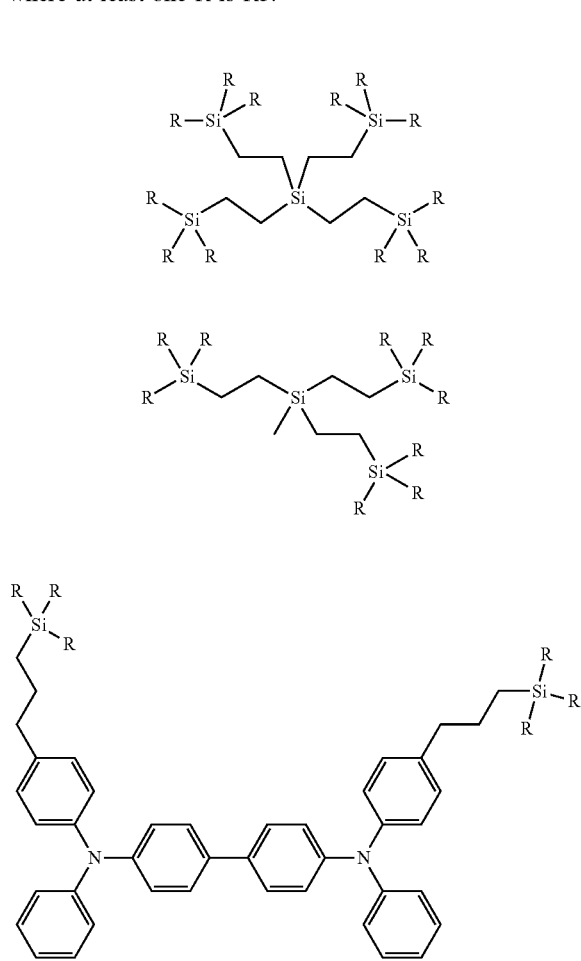

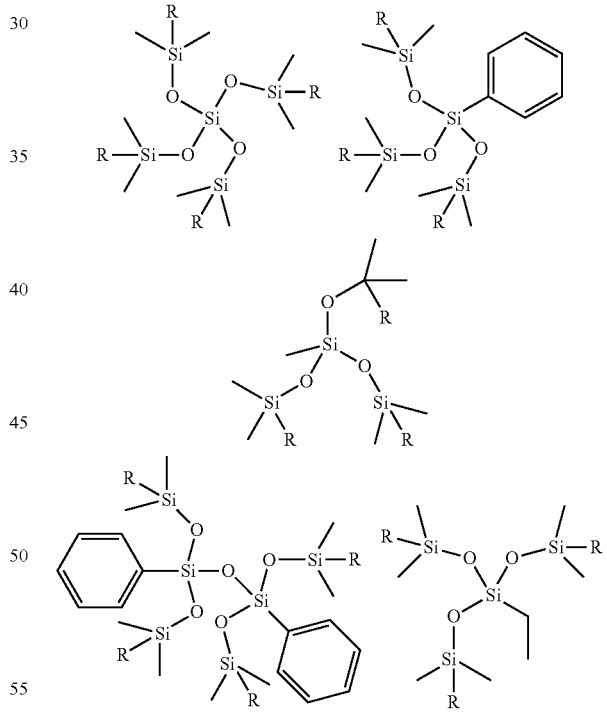

According to the invention, in the compounds of the general formula (I) or (I*), $R^1$, $R^2$, $R^3$, $R^4$, $R^5$, $R^6$, $R^7$, $R^8$, $R^9$, $R^{10}$, $R^{11}$, $R^{12}$, $R^{13}$, $R^{14}$, $R^{15}$, $R^{23}$, $R^{24}$ and $R^{25}$ are each independently a crosslinkable or polymerizable group attached via a spacer or comprise such groups as substituents.

In a preferred embodiment of the present invention, $R^1$, $R^2$, $R^3$, $R^4$ and $R^5$ are each independently a polymerizable or crosslinkable group attached via a spacer, more preferably selected from the group of functional groups which are polymerizable or crosslinkable by polycondensation or polyaddition.

More particularly, the present invention relates to inventive compounds where at least one of the $R^1$, $R^2$, $R^3$, $R^4$, $R^5$, $R^8$, $R^9$, $R^{10}$, $R^{11}$, $R^{12}$, $R^{13}$, $R^{14}$, $R^{15}$, $R^{22}$, $R^{23}$, $R^{24}$ or $R^{25}$ or $R^{28}$ radicals is independently a polymerizable or crosslinkable group attached via a spacer, selected from the group of functional groups which are polymerizable or crosslinkable, free-radically, cationically or by polyaddition or by coupling reactions.

More particularly, the present invention relates to inventive compounds wherein at least one of the radicals selected from the group of $R^1$, $R^2$ and $R^3$ is independently a polymerizable or crosslinkable group attached via a spacer.

According to the invention, a crosslinkable or polymerizable group attached via a spacer is generally a group of the formula -(Sp)$_{x1}$-[PG']$_x$,
where
Sp is a bridging unit,
PG' is a crosslinkable or polymerizable group,
x1 is 0 or 1, and
x is an integer from 1 to 4.

Sp is, for example, selected from the group consisting of —Ar—, —ArY—, —YAr—, —YAr(CR$^{26}$R$^{27}$)$_n$—, —(CR$^{26}$R$^{27}$)$_n$—, —(YCR$^{26}$R$^{27}$)—, or —(CR$^{26}$R$^{27}$Y)$_n$—,
where
Y is NR$^5$, O, S, C=O, C(=O)O, where R$^5$ is H; C$_6$-C$_{18}$-aryl optionally substituted by at least one C$_1$-C$_{18}$-alkyl or C$_1$-C$_{18}$-alkoxy, C$_1$-C$_{18}$-alkyl optionally interrupted by —O—;
R$^{26}$ and R$^{27}$ are each independently hydrogen, fluorine or C$_1$-C$_{20}$-alkyl,
n is an integer from 1 to 20,
Ar is alkyl, cycloalkyl, aryl or heteroaryl, which may optionally be substituted.

The crosslinkable or polymerizable PG' group is preferably a group selected from —C(R$^{44}$)=CH$_2$, —NHC(O)—C(R$^{45}$)=CH$_2$, —OCH$_2$CH$_2$OC(O)—C(R$^{45}$)=CH$_2$, —OC(O)—C(R$^{45}$)=CH$_2$, —C(O)—C(R$^{46}$)=CH$_2$, —C≡C—, —N≡C, —O—CH(CH$_2$CH$_2$CH=CH$_2$)$_2$; C$_5$-C$_8$-cycloalkenyl, bicycloalkenyl, optionally substituted or unsubstituted and having 5 to 30 carbon atoms,

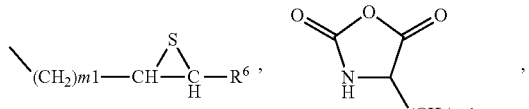

(1,2-epoxy ether),

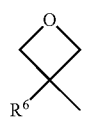

(oxetanyl),

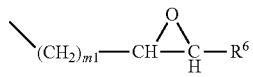

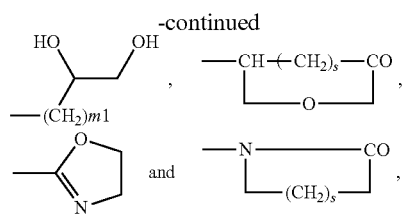

where
s is an integer from 1 to 6, m1 is an integer from 1 to 6, and
R$^6$ is hydrogen or C$_1$-C$_{20}$-alkyl.
R$^{44}$ is hydrogen, C$_1$-C$_4$-alkyl or halogen,
R$^{45}$ is hydrogen, C$_1$-C$_4$-alkyl or halogen, and
R$^{46}$ is hydrogen, C$_1$-C$_4$-alkyl or C$_6$-C$_{12}$-aryl, or
PG' in a further embodiment is a group obtainable from a polymerizable

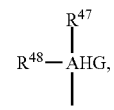

group where AHG is an aromatic or heteroaromatic radical which may optionally be substituted, for example

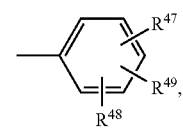

R$^{47}$ and R$^{48}$ are each independently halogen, —C≡CH, boric acid, boric ester, —Mg-Hal, —Zn-Hal, —Sn(R$^{52}$)$_3$, where Hal is halogen, and R$^{52}$ is C$_1$-C$_{18}$-alkyl.
R$^{49}$ is independently hydrogen, C$_1$-C$_{15}$-alkyl, optionally interrupted by —O—, C$_1$-C$_{18}$-perfluoroalkyl, C$_1$-C$_{18}$-alkoxy, optionally interrupted by or C$_7$-C$_{25}$-aralkyl.

When PG' is different from the polymerizable group

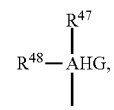

the polymers may, in addition to the repeat units mentioned, comprise one or more repeat units RG$^I$ and/or RG$^{II}$:
RG$^I$: units which improve the hole injection or hole transport properties of the polymer;
RG$^{II}$: units which improve the electron injection or electron transport properties of the polymer.
If PG' is a polymerizable group according to

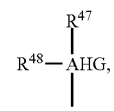

the compounds of the general formula (I) or (I*) can be polymerized as follows.
Polymerization processes which use dihalogen-functionalized substrates can be performed under nickel-mediated coupling conditions, for example according to Colon et al. in J. Pol. Sci., Part A, Polymer Chemistry Edition 28 (1990) 367, and Colon et al. in J. Org. Chem. 51 (1986) 2627. The reaction is generally performed in a polar aprotic solvent, for example dimethylacetamide, with a catalytic amount of a nickel salt, triphenylphosphine and a large excess of zinc dust. One variant of the process is described in loyda et al. in Bull. Chem. Soc. Jpn, 63 (1990) 80, wherein an organosoluble iodide is used as an accelerant. A further nickel coupling reaction is described in Yamamoto, Progress in Polymer Science 17 (1992) 1153, wherein a mixture of a dihaloaromatic compound is treated with an excess of nickel-(1,5-cyclooctadiene) complex in an inert solvent. In all nickel coupling reactions, essentially random polymers are obtained when substance mixtures of two or more aromatic dihalides are used.

Such polymerization reactions can be ended by adding a small amount of water. Alternatively, it is also possible to use a monofunctional aryl halide as the chain-terminating reagent.

Nickel coupling polymerization affords essentially random polymers composed of units of the general formula (I) and/or (I*).

In addition, the compounds of the general formula (I) or (I*) can also be polymerized by the Suzuki coupling known to those skilled in the art. This polymerization reaction is described, for example, in N. Miyaua and A. Suzuki in Chemical Reviews, Vol. 95, pp. 457-2483 (1995). For this purpose, diiodides or dibromides of the compounds of the general formula (I) or (I*) are preferably reacted with appropriate diboric acids or diboric esters. The reaction is preferably performed under Pd catalysis and in the presence of triphenylphosphine at 70° C. to 180° C. in an aromatic hydrocarbon solvent such as toluene. Dimethylformamide or tetrahydrofuran are also suitable. An aqueous base such as sodium carbonate or bicarbonate is used as an HBr scavenger. Corresponding processes are described, for example, in Leadbeater & Marco; Angew. Chem. Int. Ed. Eng. 42 (2003) 1407, T. I. Wallow and B. M. Novak in J. Org. Chem. 59 (1994) 5034-5037; and M. Remmers, M. Schulze, and G. Wegner in Macromol. Rapid Commun. 17 (1996) 239-252.

In a particularly preferred embodiment, $R^1$, $R^2$, $R^3$, $R^4$ and $R^5$, especially $R^1$, $R^2$ and $R^3$, are each independently functional groups which are free-radically crosslinkable or polymerizable, especially groups which comprise C—C double bonds. In a particularly preferred embodiment, corresponding crosslinkable or polymerizable groups or compounds of the general formula (I) or (I*) are selected from the following:

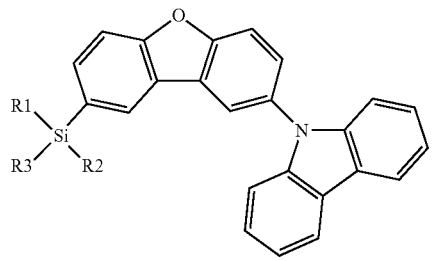

| No | R1 | R2 | R3 |
|---|---|---|---|
| 390 | Methyl | Methyl | —CH=CH$_2$ |
| 391 | Methyl | Methyl | —CH$_2$—CH=CH$_2$ |
| 392 | Methyl | Methyl | —(CH$_2$)$_3$—CH=CH$_2$ |
| 393 | Methyl | Methyl | —(CH$_2$)$_4$—CH=CH$_2$ |
| 394 | Methyl | Methyl | —(CH$_2$)$_5$—CH=CH$_2$ |
| 395 | Methyl | Methyl | —(CH$_2$)$_6$—CH=CH$_2$ |
| 396 | Methyl | Methyl | —(CH$_2$)$_9$—CH=CH$_2$ |
| 397 | Methyl | Methyl | —(CH$_2$)$_2$-cyclohex-3-enyl |
| 398 | Methyl | Methyl | (methacrylate structure) |
| 399 | Methyl | Methyl | —OSiMe$_2$CH=CH$_2$ |
| 400 | Methyl | Methyl | (siloxane-epoxide structure) |
| 401 | Methyl | Phenyl | —CH=CH$_2$ |
| 402 | Methyl | R5 | —CH=CH$_2$ |
| 403 | Methyl | R5 | —CH$_2$—CH=CH$_2$ |
| 404 | Methyl | R5 | —CH=CH—CH$_2$ |
| 405 | Methyl | R5 | —(CH$_2$)$_2$—CH=CH$_2$ |
| 406 | Methyl | R5 | —(CH$_2$)$_2$-cyclohex-3-enyl |

-continued

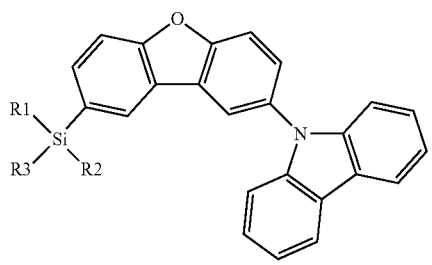

| No | R1 | R2 | R3 |
|---|---|---|---|
| 407 | Methyl | R5 | —H₂C—CH₂—CH₂—O—C(=O)—C(CH₃)=CH₂ |
| 408 | Methyl | R5 | —H₂C—CH₂—CH₂—O—C(=O)—CH=CH₂ |
| 409 | Methyl | —CH=CH₂ | —O—SiMe(R5)—CH=CH₂ |
| 410 | Ethyl | R5 | —CH=CH₂ |
| 411 | n-Hexyl | R5 | —CH₂—CH=CH₂ |
| 412 | n-Octyl | R5 | —CH=CH₂ |
| 413 | Phenyl | Phenyl | —CH=CH₂ |
| 414 | Phenyl | R5 | —CH=CH₂ |
| 415 | Phenyl | R5 | —CH₂—CH=CH₂ |
| 416 | C₆F₅ | R5 | —CH=CH₂ |
| 417 | R5 | —CH=CH₂ | —CH=CH₂ |
| 418 | R5 | —CH₂—CH=CH₂ | —CH₂—CH=CH₂ |
| 419 | R5 | R5 | —CH=CH₂ |
| 420 | R5 | R5 | —CH₂—CH=CH₂ |
| 421 | R5 | R5 | —(CH₂)₄—CH=CH₂ |
| 422 | R5 | R5 | —(CH₂)₆—CH=CH₂ |
| 423 | R5 | R5 | —(CH₂)₉—CH=CH₂ |
| 424 | R5 | R5 | —(CH₂)₂-cyclohex-3-enyl |
| 425 | R5 | R5 | cyclopent-2-enyl |
| 426 | R5 | R5 | cyclohex-3-enyl |
| 427 | R5 | R5 | Z-cyclooct-4-enyl |
| 428 | R5 | R5 | —H₂C—CH₂—CH₂—O—C(=O)—CH=CH₂ |
| 429 | R5 | R5 | —H₂C—CH₂—CH₂—O—C(=O)—C(CH₃)=CH₂ |
| 430 | R5 | R5 | —H₂C-norbornenyl |
| 431 | R5 | R5 | —H₂C—C(=CH₂)—CH₂—Si(R5)(R5)R5 |
| 432 | R5 | R5 | —(CF₂)₈(CH₂)₂—CH=CH₂ |
| 433 | R5 | R5 | —(CH₂)₂(CF₂)₈—CH=CH₂ |

-continued

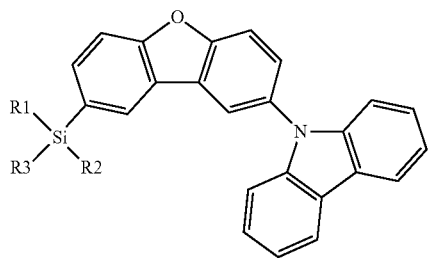

| No | R1 | R2 | R3 |
|---|---|---|---|
| 434 | —CH=CH$_2$ | —CH=CH$_2$ | —CH=CH$_2$ |
| 435 | OMe | R5 | —CH=CH$_2$ |
| 436 | OMe | OMe | —CH$_2$—CH=CH$_2$ |
| 437 |  |  |  |

In this table:

R5 = 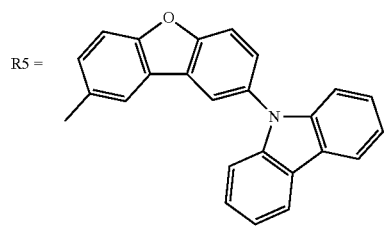 [SMILES: Cc1ccc2oc3ccc(-n4c5ccccc5c5ccccc54)cc3c2c1]

Processes for free-radical crosslinking or polymerization are known per se to those skilled in the art. It is possible in accordance with the invention to use free-radical initiators known to those skilled in the art, for example AIBN, or

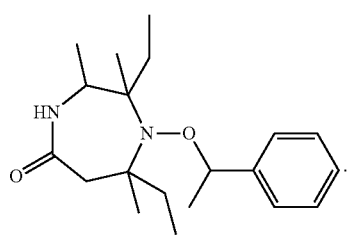 [SMILES: CCC1(C)CC(=O)NC(C)C(C)(CC)N1OC(C)c1ccccc1]

In a preferred embodiment of the present invention, the at least one polymerizable or crosslinkable group is selected from the group consisting of C—C double bond, acrylates, methacrylates, or 1,2-epoxy ether.

When the compounds of the general formula (I) or (I*) comprise —CH=CH$_2$—, acrylates or methacrylates as the crosslinkable or polymerizable group, the polymerization can be performed, for example, photochemically using known photoinitiators, described, for example in "Chemistry & Technology of UV & EB Formulations for Coatings, Inks and Paints, Vol. 3: Photoinitiators for Free Radical and Cationic Polymerization" 1991, p. 1115-325). Known photoinitiators are added to the reaction mixture, for example, in an amount of 0.5 to 5% by weight, based on the total amount of all monomers present.

Further suitable polymerization processes are epoxy polymerization, various metathesis reactions, for example described in Ivin, K. J. and Mol, J. C., Olefin Metathesis and Metathesis Polymerization (Academic Press 1997), for example ring-opening metathesis, ADMET (acyclic diene olefin metathesis), or hydrosilylation.

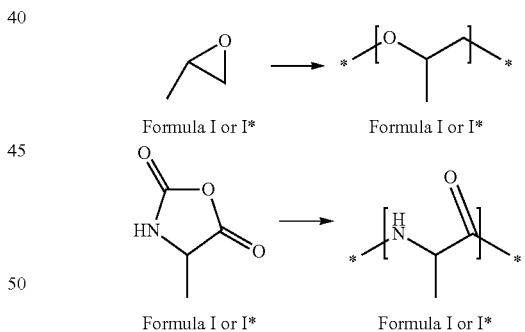

A hydrosilylation can be initiated, for example, by UV radiation, and can be catalyzed by free-radical formers, transition metal complexes or Lewis bases, for example H$_2$PtCl$_6$, RhCl(PPh$_3$)$_3$ or trans-IrCl(CO)(PPh$_3$)$_2$.

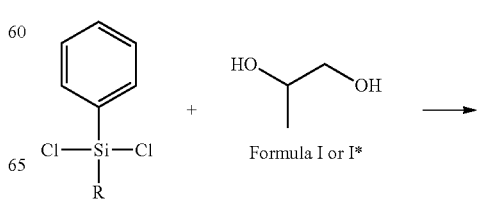

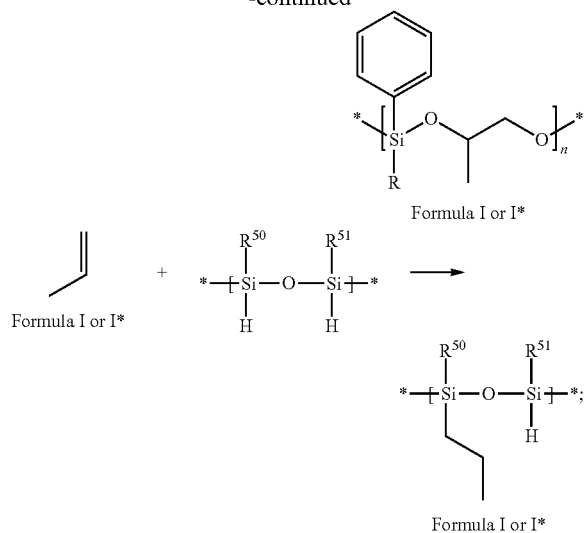

where $R^{50}$ and $R^{51}$ are each independently $C_1$-$C_8$-alkyl, $C_6$-$C_{24}$-aryl or $C_7$-$C_{12}$-aralkyl.

The polymers which are formed from the inventive compounds and are of the general formula (I) or (I*) comprise one or more compounds of the general formula (I) or (I*) in crosslinked or polymerized form. It is likewise possible that, in addition to the compounds of the general formula (I) or (I*), further monomers are also polymerized, such that corresponding copolymers are formed. Corresponding examples are specified in WO 2007/090733.

The further monomers may also hole-conducting units such as $RG^I$ and/or electron-conducting units such as $RG^{II}$ as described in WO 2007/090733.

The present invention also relates to crosslinked or polymeric materials comprising repeat units of the general formulae (I) and (I*) in crosslinked or polymerized form and to the use thereof in electronic components.

Crosslinked or polymeric materials according to the present invention have outstanding solubility in organic solvents, outstanding film-forming properties and relatively high glass transition temperatures. In addition, high charge carrier mobilities, high stabilities of color emission and long operating times of the corresponding components can be observed when crosslinked or polymeric materials according to the present invention are used in organic light-emitting diodes (OLEDs).

The inventive crosslinked or polymerized materials are particularly suitable as coatings or in thin films, since they are thermally and mechanically stable and are relatively defect-free.

Suitable processes for producing these thin films are, for example, vacuum deposition, spin-coating, the casting method, the Langmuir-Blodgett ("LB") method, the inkjet printing method, dip-coating, letterpress printing, screen printing, doctor-blade printing, roller printing, reverse-roller printing, offset lithography printing, flexographic printing, web printing, spray-coating, coating by means of a brush or pad printing and the like. Among the processes mentioned, vacuum deposition, spin-coating, the inkjet printing method and the casting method are preferred, since they can be performed in a particularly simple and inexpensive manner.

The individual component layers, especially the light emission layer, may be formed from a mixture of the inventive compounds and/or materials and optionally further compounds. The nonconjugated polymers of the present invention are particularly useful as host materials for phosphorescent compounds (triplet emitters) in organic light-emitting diodes (OLEDs).

In the case that layers are obtained by the spin-coating method, the casting method or the inkjet printing method, the coating can be obtained using a solution prepared by dissolving the composition in a concentration of 0.0001 to 90% by weight in a suitable organic solvent such as benzene, toluene, xylene, tetrahydrofuran, methyltetrahydrofuran, N,N-dimethylformamide, acetone, acetonitrile, anisole, dichloromethane, dimethyl sulfoxide and mixtures thereof.

The present invention also relates especially to the use of an inventive compound of the general formula (I) or (I*) as units in polymerization and/or crosslinking reactions.

The present invention further relates to a process for preparing a crosslinked or polymerized material comprising at least one inventive compound of the general formula (I) or (I*), comprising the steps of:

(A) preparing a crosslinkable or polymerizable compound of the general formula (I) or (I*), where at least one of $R^1$, $R^2$, $R^3$, $R^4$, $R^5$, $R^8$, $R^9$, $R^{10}$, $R^{11}$, $R^{12}$, $R^{13}$, $R^{14}$, $R^{15}$, $R^{22}$, $R^{23}$, $R^{24}$, $R^{25}$ or $R^{28}$ is a crosslinkable or polymerizable group attached via a spacer, and (B) crosslinking or polymerizing the compound of the general formula (I) or (I*) obtained from step (A).

Step (A) comprises the preparation of the crosslinkable or polymerizable compounds. This is preferably done by the process according to the invention.

The polymerization according to step (B) is likewise performed by the above-described process.

The present invention also relates to a crosslinked or polymerized material which comprises units of the general formula (I) or (I*) which comprise crosslinkable or polymerizable groups in crosslinked or polymerized form. This material is preferably obtained by the polymerization processes mentioned.

According to the invention, the materials may be homopolymers, i.e. exclusively units of the general formula (I) or (I*) are present in crosslinked or polymerized form. Also encompassed by the invention are copolymers, i.e., as well as the units of the general formula (I) or (I*), further monomers are present in crosslinked or polymerized form, for example monomers with hole-conducting and/or electron-conducting properties.

The crosslinked or polymerized material which is obtained by the process according to the invention and comprises units of the general formula (I) or (I*) is particularly suitable for use in organic electronics applications, especially in OLEDs.

The present invention therefore also relates to the use of the crosslinked or polymerized material which comprises units of the general formula (I) or (I*) in organic electronics applications, especially in OLEDs.

In the abovementioned compounds of the formula (I) or (I*), partial structures, for example carbazole, triphenylsilyl and phosphine oxide structures, may be combined in one molecule, which may lead to an improved interaction with the emitter molecule (when the compounds are used as matrix materials) and hence high quantum and power efficiencies. The asymmetry of these compounds also allows the material to be deposited from the gas phase in amorphous form. Amorphous organic materials generally have a better long-term stability than crystalline organic materials. Such a compound of the formula (I) or (I*) may, for example, be the compound (Ia):

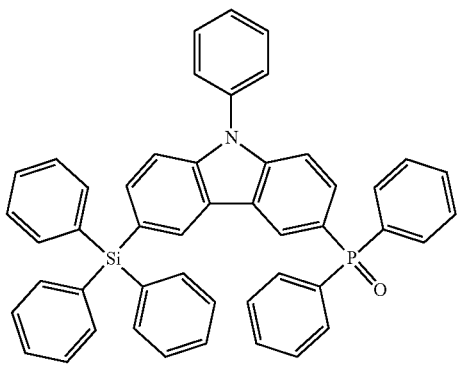

(Ia)

Compared to a reference compound with, for example, one carbazole partial structure and two triphenylsilyl partial structures, the charge carrier mobility, especially the electron mobility, is increased in a compound of the general formula (I) or (I*) with one carbazole unit, one triphenylsilyl unit and one phosphine oxide unit, for example a compound (Ia). This allows, for example, the operating voltage of an OLED to be lowered with equal luminance.

The compounds of the formula (I) or (I*) or a corresponding crosslinked or polymerized material can be used as matrix materials and/or blocker materials and/or electron and/or hole conductors of white light-emitting OLEDs.

Preparation of the Inventive Compounds of the Formula (I) or (I*) and of Those Used in Accordance with the Invention The compounds of the formula (I) or (I*) can in principle be prepared by processes known to those skilled in the art; for example, carbazoles of the formula (I) or (I*) (X=NR) can be prepared thermally or photochemically by oxidative ring closure from diphenylamine (or suitably substituted derivatives thereof) and if appropriate subsequent substitution, for example on the nitrogen. In addition, the carbazoles of the formula (I) or (I*) can be obtained proceeding from the suitably substituted tetrahydrocarbazoles by oxidation. A typical carbazole synthesis is the Borsche-Drechsel cyclization (Borsche, Ann., 359, 49 (1908); Drechsel, J. prakt. Chem., [2], 38, 69, 1888). The aforementioned tetrahydrocarbazoles can be prepared by processes known to those skilled in the art, for example by condensation of optionally suitably substituted phenylhydrazine with optionally suitably substituted cyclohexanone to obtain the corresponding imine. In a subsequent step, an acid-catalyzed rearrangement and ring closure reaction is effected to obtain the corresponding tetrahydrocarbazole. It is likewise possible to perform the preparation of the imine and the rearrangement and ring closure reaction in one step. The imine is—as mentioned above—oxidized to the desired carbazole.

The compounds of the formula (I) or (I*) are preferably prepared proceeding from the corresponding base skeleton of the formula (II):

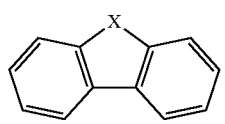

(II)

where X is NR, S, O or PR or NH or PH or PPh. Suitable base skeletons of the formula (II) are either commercially available (especially in the cases when X is S, O, NH or PPh) or by processes known to those skilled in the art (X=PH).

In the case that X is NH or PH, the R radicals can be introduced before or after the introduction of the $R^4$, $R^5$, $SiR^1R^2R^3$ and A radicals, where the $R^4$ and $R^5$ radicals are present in the compounds of the formula (I) or (I*), or precursor compounds suitable for introduction of the $R^4$, $R^5$, $SiR^1R^2R^3$ and A radicals. Three variants are thus possible—in the case that X=NR and PR:

Variant a)
ia) preparing a precursor compound suitable for introduction of the $R^4$, $R^5$, $SiR^1R^2R^3$ and A radicals,
iia) introducing the R radical,
iiia) introducing the $R^4$, $R^5$ radicals, where present, and the $SiR^1R^2R^3$ and A radicals.

Variant b)
Variant b) is preferred especially when R is alkyl or aryl or alkyl-substituted aryl.
ib) introducing the R radical,
iib) preparing a precursor compound suitable for introduction of the $R^4$, $R^5$, $SiR^1R^2R^3$ and A radicals,
iiib) introducing the $R^4$, $R^5$ radicals, where present, and the $SiR^1R^2R^3$ and A radicals.

Variant c)
ic) preparing a precursor compound suitable for introduction of the $R^4$, $R^5$, $SiR^1R^2R^3$ and A radicals,
iic) introducing the $R^4$, $R^5$ radicals, where present, and the $SiR^1R^2R^3$ and A radicals,
iiic) introducing the R radical.

In the case that X in formula (II) is NR, S, O or PR, the step of "introducing the R radical" is dispensed with, and so the process comprises the following steps (variant d):
id) preparing a precursor compound suitable for introduction of the $R^4$, $R^5$, $SiR^1R^2R^3$ and A radicals,
iid) introducing the $R^4$, $R^5$ radicals, where present, and the $SiR^1R^2R^3$ and A radicals.

In a further embodiment, the present invention therefore relates to a process for preparing the inventive compounds of the formula (I) or (I*) and those used in accordance with the invention,
proceeding from a base skeleton of the formula (II):

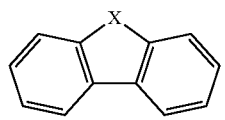

(II)

in which X is NR, S, O or PR or NH or PH or PPh, the R, $R^4$, $R^5$, $SiR^1R^2R^3$ and A radicals, where the $R^4$ and $R^5$ radicals are present in the compounds of the formula (I) or (I*), are introduced by one of the following variants a), b), c) or d), Variant a)
ia) preparing a precursor compound suitable for introduction of the $R^4$, $R^5$, $SiR^1R^2R^3$ and A radicals,
iia) introducing the R radical,
iiia) introducing the $R^4$, $R^5$ radicals, where present, and the $SiR^1R^2R^3$ and A radicals; or Variant b)
ib) introducing the R radical,
iib) preparing a precursor compound suitable for introduction of the $R^4$, $R^5$, $SiR^1R^2R^3$ and A radicals,
iiib) introducing the $R^4$, $R^5$ radicals, where present, and the $SiR^1R^2R^3$ and A radicals; or Variant c)

ic) preparing a precursor compound suitable for introduction of the R⁴, R⁵, SiR¹R²R³ and A radicals, iic) introducing the R⁴, R⁵ radicals, where present, and the SiR¹R²R³ and A radicals, iiic) introducing the R radical; or Variant d)

id) preparing a precursor compound suitable for introduction of the R⁴, R⁵, SiR¹R²R³ and A radicals, iid) introducing the R⁴, R⁵ radicals, where present, and the SiR¹R²R³ and A radicals.

The m, n, R, R⁴, R⁵, SiR¹R²R³ and A radicals and groups specified in the compounds of the formula (I) or (I*) have been defined above.

Step ia), ic) and id)

Suitable precursor compounds for introduction of the R⁴, R⁵, SiR¹R²R³ and A radicals are especially the corresponding halogenated, preferably brominated, compounds of the general formula (III):

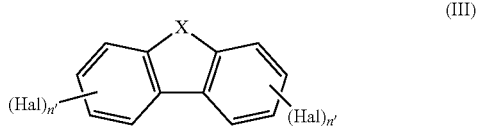

where Hal is halogen, preferably bromine or iodine, more preferably bromine, n' in each case is 0 or 1 (where at least one n' in formula (III) is 1) and X in step ia) and ic) is NH or PH, X in step ib) is NR or PR and X in step id) is NR, S, O or PR.

The halogenation can be performed by methods known to those skilled in the art. Preference is given to brominating or iodinating in the 3 and 6 positions (dibromination) or in the 3 or 6 positions (monobromination) of the base skeleton of the formula (II), 2,8 positions (dibenzofuran and dibenzothiophene) or 3,6 positions (carbazole).

Optionally substituted dibenzofurans, dibenzothiophenes and carbazoles can be dibrominated in the 2,8 positions (dibenzofuran and dibenzothiophene) or 3,6 positions (carbazole) with bromine or NBS in glacial acetic acid or in chloroform. For example, the bromination with Br₂ can be effected in glacial acetic acid or chloroform at low temperatures, e.g. 0° C. Suitable processes are described, for example, in M. Park, J. R. Buck, C. J. Rizzo, Tetrahedron, 1998, 54, 12707-12714 for X=NPh, and in W. Yang et al., J. Mater. Chem. 2003, 13, 1351 for X=S. In addition, 3,6-dibromocarbazole, 3,6-dibromo-9-phenylcarbazole, 2,8-dibromodibenzothiophene, 2,8-dibromodibenzofuran, 2-bromocarbazole, 3-bromodibenzothiophene, 3-bromodibenzofuran, 3-bromocarbazole, 2-bromodibenzothiophene and 2-bromodibenzofuran are commercially available.

Monobromination in the 4 position of dibenzofuran (and analogously for dibenzothiophene) is described, for example, in J. Am. Chem. Soc. 1984, 106, 7150. Dibenzofuran (dibenzothiophene) can be monobrominated in the 3 position by a sequence known to those skilled in the art, comprising a nitration, reduction and subsequent Sandmeyer reaction.

Monobromination in the 2 position of dibenzofuran or dibenzothiophene and monobromination in the 3 position of carbazole are effected analogously to the dibromination, with the exception that only one equivalent of bromine or NBS is added.

Preference is also given to utilizing iodinated dibenzofurans, dibenzothiophenes and carbazoles. It is also possible to use mixed (once iodinated+once brominated) compounds.

The preparation is described, inter alia, in Tetrahedron. Lett. 2006, 47, 6957-6960, Eur. J. Inorg. Chem. 2005, 24, 4976-4984, J. Heterocyclic Chem. 2002, 39, 933-941, J. Am. Chem. Soc. 2002, 124, 11900-11907, J. Heterocyclic Chem. 2001, 38, 77-87.

For the nucleophilic substitution, Cl- or F-substituted dibenzofurans, dibenzothiophenes and carbazoles are required. The chlorination is described, inter alia, in J. Heterocyclic Chemistry, 1997, 34, 891-900, Org. Lett., 2004, 6, 3501-3504; J. Chem. Soc. [Section] C: Organic, 1971, 16, 2775-7, Tetrahedron Lett. 1984, 25, 5363-6, J. Org. Chem. 2004, 69, 8177-8182. The fluorination is described in J. Org. Chem. 1998, 63, 878-880 and J. Chem. Soc., Perkin Trans. 2 2002, 5, 953-957.

Step iia), ib) and iiic)

The R radical is introduced by methods known to those skilled in the art.

The radical is introduced preferably by reacting the base skeleton of the formula (III) or the compound of the formula (III) with an alkyl halide or aryl halide or heteroaryl halide of the formula R-Hal where R has already been defined above and Hal is F, Cl, Br or I, preferably Br, I or F.

The introduction of the R radical is performed generally in the presence of a base. Suitable bases are known to those skilled in the art and are preferably selected from the group consisting of alkali metal and alkaline earth metal hydroxides such as NaOH, KOH, Ca(OH)₂, alkali metal hydrides such as NaH, KH, alkali metal amides such as NaNH₂, alkali metal or alkaline earth metal carbonates such as K₂CO₃ or Cs₂CO₃, and alkali metal alkoxides such as NaOMe, NaOEt. In addition, mixtures of the aforementioned bases are suitable. Particular preference is given to NaOH, KOH, NaH, or K₂CO₃.

N-Alkylation (for example disclosed in M. Tosa et al., Heterocycl. Communications, Vol. 7, No. 3, 2001, p. 277-282) or N-arylation or N-heteroarylation (for example (N-arylation) disclosed in H. Gilman and D. A. Shirley, J. Am. Chem. Soc. 66 (1944) 888; D. Li et al., Dyes and Pigments 49 (2001) 181-186) is preferably performed in a solvent. Suitable solvents are, for example, polar aprotic solvents such as dimethyl sulfoxide, dimethylformamide or alcohols. It is likewise possible to use an excess of the alkyl halide or (hetero)aryl halide as a solvent. The reaction can additionally be performed in a nonpolar aprotic solvent, for example toluene, when a phase transfer catalyst, for example tetra-n-butylammonium hydrogensulfate, is present (as disclosed, for example, in I. Gozlan et al., J. Heterocycl. Chem. 21 (1984) 613-614).

The N-(hetero)arylation can be effected, for example, by copper-catalyzed coupling of the compound of the formula (II) or (III) to a (hetero)aryl halide, for example an aryl iodide (Ullmann reaction).

Preference is given to introducing the R radical by reacting the compound of the formula (II) or (III) with an alkyl, aryl or heteroaryl fluoride in the presence of NaH in DMF (nucleophilic substitution) or by reaction with an alkyl, aryl or heteroaryl bromide or alkyl, aryl or heteraryl iodide under Cu/base (Ullmann, see above) or Pd catalysis.

The molar ratio of the compound of the formula (II) or (III) to the alkyl halide or (hetero)aryl halide of the formula R¹-Hal is generally 1:1 to 1:15, preferably 1:1 to 1:6, more preferably 1:4.

The N-alkylation or N-(hetero)arylation is generally performed at a temperature of 0 to 220° C., preferably 20 to 200° C. The reaction time is generally 0.5 to 48 h, preferably 1 to 24 h. In general, the N-alkylation or N-arylation is performed at standard pressure.

The resulting crude product is worked up by processes known to those skilled in the art.

Preferred embodiments of steps iia), ib) and iiic) are shown below in general form using the example of R=substituted phenyl (R"=aforementioned substitutent on the aryl radical; q=0, 1, 2, 3, 4 or 5):

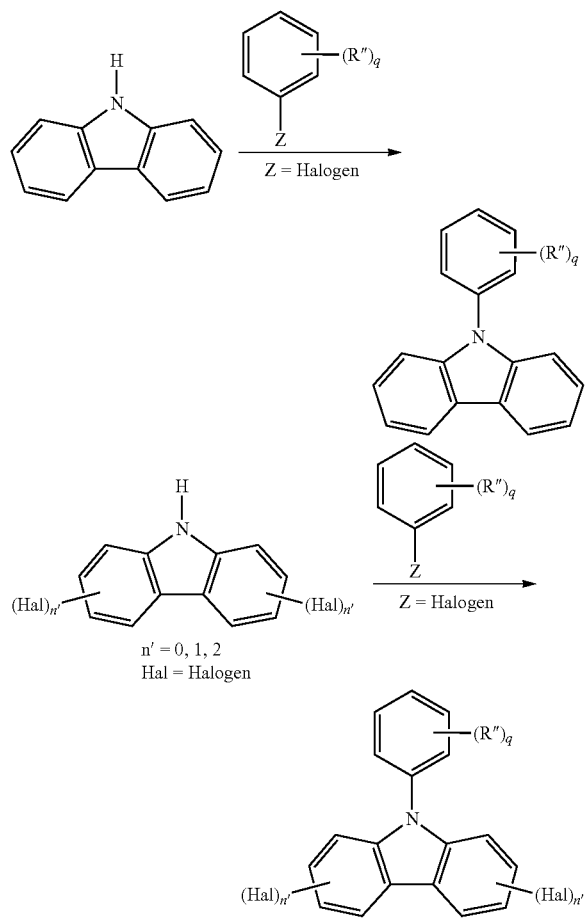

Steps iiia), iiib), iic) and iid)

The desired compounds of the formula (I) or (I*) are prepared proceeding from the halogenated precursor compounds of the formula (III) generally by the following steps:
aa) halogen/metal exchange or metallation, preferably lithiation, more preferably ortholithiation, and subsequent silylation by processes known to those skilled in the art to obtain a compound of the formula (IVa);

(IVa)

ab) coupling step to introduce the A radical to obtain the desired compound of the formula (I) or (I*).

Alternatively, the desired compounds of the formula (I) or (I*) can be prepared proceeding from the halogenated precursor compounds of the formula (III) generally by the following steps:
ba) coupling step to introduce the A radical to obtain the desired compound of the formula (IVb);

(IVb)

bb) halogen/metal exchange and subsequent silylation by processes known to those skilled in the art to obtain the desired compound of the formula (I) or (I*).

Step aa) or Schritt bb): Halogen/Metal Exchange and Subsequent Silylation

Preferably, step aa) or step bb) is effected, in a first step, by halogen/metal exchange by reacting the halogenated compounds of the formula (III) with alkyllithium compounds or Mg at temperatures of generally −80° C. to +80° C., preferably at −40° C. to 30° C. (for alkyllithium compounds) or 0° C. to 80° C. (for Mg), more preferably of 0° C. to 40° C. (for Mg). Particular preference is given to using alkyllithium compounds, especially n-BuLi or tert-BuLi. Particular preference is given to first initially charging the (chloro)silane and aryl halides, i.e. the halogenated base skeleton (II), together, then to adding dropwise n-BuLi or tert-BuLi.

The present invention therefore relates more particularly to the process according to the invention wherein the silane reactant is initially charged simultaneously with the halogenated base skeleton (II) and then the metal reagent is added.

The reaction is generally effected in a solvent, preferably in THF or ethers, preferably diethyl ether. According to the invention, the synthesis yields are particularly good when diethyl ether is utilized as a solvent.

The present invention therefore preferably relates to the process according to the invention wherein a halogen-metal exchange is performed on the halogenated base skeleton (II) in diethyl ether as a solvent.

In a further embodiment, in step aa), instead of the halogen/metal exchange, a metallation is effected, preferably a lithiation, more preferably an ortholithiation. A lithiation, preferably an ortholithiation, is known per se to those skilled in the art, for example at a temperature of −100° C. to 25° C., preferably at −78° C. to RT, more preferably −40° C. to 0° C. The inventive metallation is preferably performed in an aprotic solvent, for example in THF. On completion of metallation, in a second step, the appropriate silane reagent is subsequently added in a solvent, for example in THF. This is explained in detail hereinafter.

In a second step which follows directly, a silylation is effected to give the compounds of the formula (IVa), preferably by reaction with $SiR_mCl_{(4-m)}$ or $SiR_mH_{(4-m-n)}Cl_n$, where m is 0, 1, 2 or 3 and n is 0, 1, 2 and n+m≤3. The utilization of Si—H compounds is described in H. Gilman, W. J. Trepka *J. Org. Chem.* 1962, 27(4), 1418-1422. Si—H compounds are generally more stable than the chlorosilanes. The silylation is generally performed in a solvent. Preferred solvents are THF or ethers, preferably diethyl ether. In general, the silylation is effected directly after the reaction in the first step, without workup or isolation of the product obtained after the first step.

In the case when the halogen/metal exchange and the subsequent silylation are performed on a compound of the formula (III) in which X=NH or PH (variant c), step iic)), it is necessary to protect the NH or PH group by means of a protecting group and to deprotect it again after the silylation.

The protecting group is introduced by processes known to those skilled in the art. In general, initial deprotonation is followed by the introduction of a protecting group. Suitable N—H and P—H protecting groups are known to those skilled in the art, particularly suitable protecting groups for this process being silyl protecting groups, especially $SiR_3$ where R=alkyl or aryl, preferably methyl, ethyl, phenyl. The deprotonation is effected typically with bases, for example with NaH, nBuLi or tert-BuLi.

The deprotection is likewise effected by processes known to those skilled in the art. Suitable reagents for deprotection are guided by the protecting groups used. In the case of use of $SiR_3$ as the protecting group, the deprotection is generally effected with an acid or TBAF (tetrabutylammonium fluoride).

Step ab) or ba): Coupling

The introduction of the A group can be performed by the processes specified for the introduction of the R radical. In general, the A group is introduced in the presence of a base. Suitable bases are known to those skilled in the art and are preferably selected from the group consisting of alkali metal and alkaline earth metal hydroxides such as NaOH, KOH, $Ca(OH)_2$, alkali metal hydrides such as NaH, KH, alkali metal amides such as $NaNH_2$, alkali metal or alkaline earth metal carbonates such as $K_2CO_3$ or $Cs_2CO_3$, and alkali metal alkoxides such as NaOMe, NaOEt. In addition, mixtures of the aforementioned bases are suitable. Particular preference is given to NaOH, KOH, NaH or $K_2CO_3$.

Heteroarylation can be effected, for example, by copper-catalyzed coupling of the A radical to a halogenated compound of the formula (III) or (IVa) (Ullmann reaction).

The N-arylation was, for example, disclosed in H. Gilman and D. A. Shirley, J. Am. Chem. Soc. 66 (1944) 888; D. Li et al., Dyes and Pigments 49 (2001) 181-186). The reaction can be performed in solvent or in a melt. Suitable solvents are, for example, (polar) aprotic solvents such as dimethyl sulfoxide, dimethylformamide, NMP, tridecane or alcohols. It is likewise possible to use an excess of one of the starting materials used (compound of the formula (III) or (IVa) or precursor compound of the A group) as the solvent.

Preference is given to introducing the A radical by converting the compound of the formula (III) or (IVa) in the presence of NaH in DMF (nucleophilic substitution) or by reaction under Cu/base (Ullmann, see above) or Pd catalysis conditions.

The N-alkylation or N-(hetero)arylation is generally performed at a temperature of 0 to 220° C., preferably 20 to 200° C. The reaction time is generally 0.5 to 76 h, preferably 1 to 48 h.

The resulting crude product (desired compound of the formula (I) or (I*)) is worked up by processes known to those skilled in the art.

Alternatively, it is also possible to perform additional halogenation steps on the desired compound of the formula (I) or (I*), followed by couplings and/or silylations, in order if appropriate to introduce the $R^4$ and $R^5$ radicals.

Substituents attached via phosphorus are introduced by means of a halogen/metal exchange, as described above, and a subsequent reaction with a chlorophosphine compound. When the target product is a phosphine oxide, subsequent oxidation is effected with, for example, $H_2O_2$ in water or mCPBA in $CH_2Cl_2$.

A general process scheme for preparation of the inventive compounds of the formula (I) or (I*) is shown below:

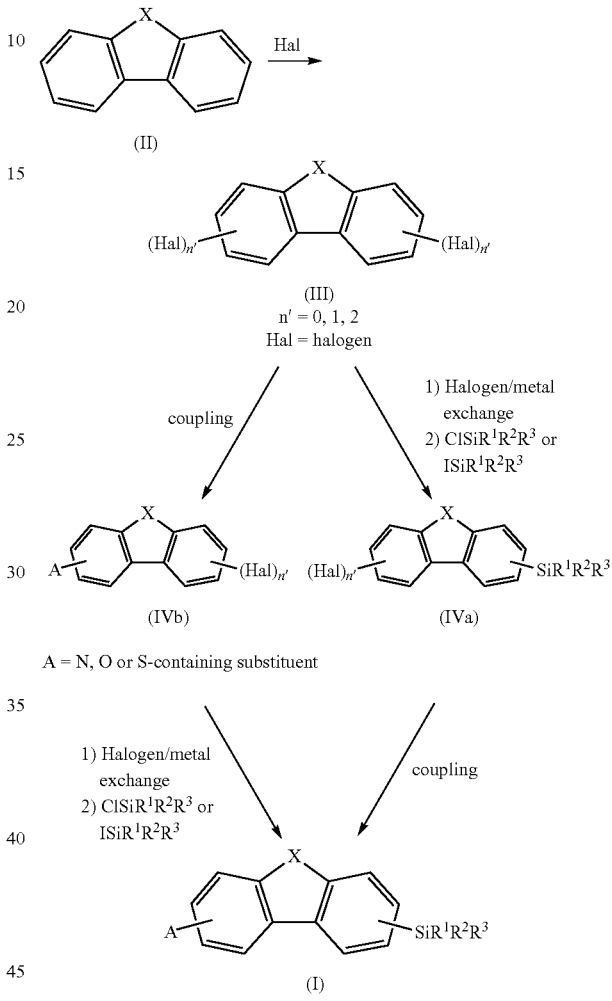

Compounds of the general formula (I*) are prepared analogously or via ortholithiation and silylation, as described above.

The inventive compounds of the formula (I) or (I*) used or an inventive crosslinked or polymerized material can be used in organic electronics applications selected from switching elements such as organic transistors, for example organic FETs and organic TFTs, organic solar cells and organic light-emitting diodes (OLEDs), preference being given to using the compounds of the formula (I) or (I*) in OLEDs.

The present application therefore further provides for the use of the compounds of the formula (I) or (I*) or an inventive crosslinked or polymerized material in organic electronics applications, preferably in OLEDs.

The compounds of the formula (I) or (I*) or an inventive crosslinked or polymerized material are notable in that they have at least one silyl and at least one heteroatom substitution on a carbazole, dibenzofuran, dibenzothiophene or dibenzophosphole base skeleton. These specific compounds are notable especially in that they ensure good efficiencies, good operative lifetimes and a high stability to thermal stress, and a low use and operating voltage of the organic electronics applications, especially of the OLEDs.

The compounds of the formula (I) or (I*) or an inventive crosslinked or polymerized material can be used as matrix material and/or hole/exciton blocker material and/or electron/exciton blocker material and/or hole injection material and/or electron injection material and/or hole conductor material and/or electron conductor material, preferably as matrix material and/or hole/exciton blocker material in organic electronics applications, especially in OLEDs. The inventive compounds of the formula (I) or (I*) are more preferably used as matrix and/or hole/exciton blocker materials in organic electronics applications, especially in OLEDs.

The use of one of the compounds of the formula (I) or (I*) or an inventive crosslinked or polymerized material as a matrix material in combination with an emitter material leads to improved efficiency values and to a decrease in the voltage in OLEDs with equal luminance compared to OLEDs which do not comprise a matrix material with a compound of the formula (I) or (I*). The decreased voltage is attributable to a good conductivity of charge carriers, for example of electrons, in the OLED.

In the emission layer or one of the emission layers of an OLED, it is also possible to combine an emitter material with a matrix material of the compound of the formula (I) or (I*) or an inventive crosslinked or polymerized material and a further matrix material which has, for example, a good hole conductor property. This achieves a high quantum efficiency of this emission layer.

Owing to the transport properties and the position of the triplet level and hence the exciton blocker properties of the compounds of the formula (I) or (I*) or the inventive crosslinked or polymerized material, these compounds can also be used as hole/exciton blocker material and/or electron/exciton blocker material. Compounds of the formula (I) or (I*) or an inventive crosslinked or polymerized material which have a good electron conductor property can especially be used on the cathode side of an OLED.

When a compound of the formula (I) or (I*) or an inventive crosslinked or polymerized material is used as matrix material in an emission layer and additionally as hole/exciton blocker material and/or electron/exciton blocker material, owing to the chemical identity or similarity of the materials, an improved interface between the emission layer and the adjacent hole/exciton blocker material and/or electron/exciton blocker material is obtained, which can lead to a decrease in the voltage with equal luminance and to an extension of the lifetime of the OLED. Moreover, the use of the same material for hole/exciton blocker material and/or electron/exciton blocker material and for the matrix of an emission layer allows the production process of an OLED to be simplified, since the same source can be used for the application of the material comprising at least one of the compounds of the formula (I) or (I*) or an inventive crosslinked or polymerized material.

Suitable structures of the organic electronics applications are known to those skilled in the art and are specified below.

The organic transistor generally includes a semiconductor layer formed from an organic layer with hole transport capacity and/or electron transport capacity; a gate electrode formed from a conductive layer; and an insulating layer introduced between the semiconductor layer and the conductive layer. A source electrode and a drain electrode are mounted on this arrangement in order thus to produce the transistor element. In addition, further layers known to those skilled in the art may be present in the organic transistor. The compound of the formula (I) or (I*) or an inventive crosslinked or polymerized material may be present in any desired layer of the organic transistor.

The organic solar cell (photoelectric conversion element) generally comprises an organic layer present between two plate-type electrodes arranged in parallel. The organic layer may be configured on a comb-type electrode. There is no particular restriction regarding the site of the organic layer and there is no particular restriction regarding the material of the electrodes. When, however, plate-type electrodes arranged in parallel are used, at least one electrode is preferably formed from a transparent electrode, for example an ITO electrode or a fluorine-doped tin oxide electrode. The organic layer is formed from two sublayers, i.e. a layer with p-type semiconductor properties or hole transport capacity, and a layer formed with n-type semiconductor properties or electron transport capacity. In addition, it is possible for further layers known to those skilled in the art to be present in the organic solar cell. The compound of the formula (I) or (I*) or an inventive crosslinked or polymerized material may be present in any desired layer of the organic solar cell.

In a further embodiment, the present invention relates to an organic light-emitting diode comprising at least one compound of the formula (I) or (I*) or an inventive crosslinked or polymerized material. The compound of the formula (I) or (I*) or an inventive crosslinked or polymerized material can be used in the organic light-emitting diode as matrix material and/or hole/exciton blocker material and/or electron/exciton blocker material and/or hole injection material and/or electron injection material and/or hole conductor material and/or electron conductor material, preferably as matrix material and/or hole/exciton blocker material in organic electronics applications, especially in OLEDs.

In a preferred embodiment of the invention, compounds of the general formula I or I* or an inventive crosslinked or polymerized material in a mixture, for example together with another hole conductor or electron conductor, are used in the hole-conducting or electron-conducting layer. The further hole conductors or electron conductors used may generally be materials known to those skilled in the art, especially the hole or electron conductors specified below.

In a further embodiment, the present invention relates to an organic light-emitting diode, in which the compounds of the formula (I) or (I*) or an inventive crosslinked or polymerized material are used as hole/exciton blockers, preferably in a blocking layer for holes, or in the light-emitting layer, preferably as matrix material.

It is likewise possible that the compounds of the formula (I) or (I*) or an inventive crosslinked or polymerized material are present both in the light-emitting layer (preferably as matrix material) and in the blocking layer for holes (as hole/exciton blockers).

In a particularly preferred embodiment, the present invention relates to an OLED in which all layers, i.e. hole conductor, electron blocker, matrix, hole blocker and electron conductor, comprise compounds of the formula (I) or (I*) or a material crosslinked or polymerized in accordance with the invention, more preferably consist thereof, the emission layer additionally comprising an emitter.

The present invention further provides an organic light-emitting diode comprising an anode An and a cathode Ka and a light-emitting layer E arranged between the anode An and the cathode Ka, and if appropriate at least one further layer selected from the group consisting of at least one blocking layer for holes/excitons, at least one blocking layer for electrons/excitons, at least one hole injection layer, at least one hole conductor layer, at least one electron injection layer and at least one electron conductor layer, wherein the at least one compound of the formula (I) or (I*) or an inventive crosslinked or polymerized material is present in the light-emitting layer E and/or in at least one of the further layers. The at least one compound of the formula (I) or (I*) is preferably present in the light-emitting layer and/or the blocking layer for holes.

The present application further relates to a light-emitting layer comprising at least one compound of the formula (I) or (I*) or an inventive crosslinked or polymerized material.

The present invention further provides an OLED comprising an inventive light-emitting layer.

The present invention further relates to a blocking layer for holes/excitons comprising at least one compound of the formula (I) or (I*) or an inventive crosslinked or polymerized material.

Structure of the Inventive OLED

The inventive organic light-emitting diode (OLED) thus generally has the following structure:
an anode (An) and a cathode (Ka) and a light-emitting layer E arranged between the anode (An) and the cathode (Ka).

The inventive OLED may, for example—in a preferred embodiment—be formed from the following layers:
1. Anode
2. Hole conductor layer
3. Light-emitting layer
4. Blocking layer for holes/excitons
5. Electron conductor layer
6. Cathode Layer sequences different than the aforementioned structure are also possible, and are known to those skilled in the art. For example, it is possible that the OLED does not have all of the layers mentioned; for example, an OLED with layers (1) (anode), (3) (light-emitting layer) and (6) (cathode) is likewise suitable, in which case the functions of the layers (2) (hole conductor layer) and (4) (blocking layer for holes/excitons) and (5) (electron conductor layer) are assumed by the adjacent layers. OLEDs which have layers (1), (2), (3) and (6), or layers (1), (3), (4), (5) and (6), are likewise suitable. In addition, the OLEDs may have a blocking layer for electrons/excitons between the anode (1) and the hole conductor layer (2).

It is additionally possible that a plurality of the aforementioned functions (electron/exciton blocker, hole/exciton blocker, hole injection, hole conduction, electron injection, electron conduction) are combined in one layer and are assumed, for example, by a single material present in this layer. For example, a material used in the hole conductor layer, in one embodiment, may simultaneously block excitons and/or electrons.

Furthermore, the individual layers of the OLED among those specified above may in turn be formed from two or more layers. For example, the hole conductor layer may be formed from a layer into which holes are injected from the electrode, and a layer which transports the holes away from the hole-injecting layer into the light-emitting layer. The electron conduction layer may likewise consist of a plurality of layers, for example a layer in which electrons are injected by the electrode, and a layer which receives electrons from the electron injection layer and transports them into the light-emitting layer. These layers mentioned are each selected according to factors such as energy level, thermal resistance and charge carrier mobility, and also energy difference of the layers specified with the organic layers or the metal electrodes. The person skilled in the art is capable of selecting the structure of the OLEDs such that it is matched optimally to the organic compounds used as emitter substances in accordance with the invention.

In order to obtain particularly efficient OLEDs, for example, the HOMO (highest occupied molecular orbital) of the hole conductor layer should be matched to the work function of the anode, and the LUMO (lowest unoccupied molecular orbital) of the electron conductor layer should be matched to the work function of the cathode, provided that the aforementioned layers are present in the inventive OLEDs.

The anode (1) is an electrode which provides positive charge carriers. It may be formed, for example, from materials which comprise a metal, a mixture of various metals, a metal alloy, a metal oxide or a mixture of various metal oxides. Alternatively, the anode may be a conductive polymer. Suitable metals comprise metals and alloys of the metals of the main groups, transition metals and of the lanthanoids, especially the metals of groups Ib, IVa, Va and VIa of the periodic table of the elements, and the transition metals of group VIIIa. When the anode is to be transparent, generally mixed metal oxides of groups IIb, IIIb and IVb of the periodic table of the elements (IUPAC version) are used, for example indium tin oxide (ITO). It is likewise possible that the anode (I) comprises an organic material, for example polyaniline, as described, for example, in Nature, Vol. 357, pages 477 to 479 (Jun. 11, 1992). At least either the anode or the cathode should be at least partly transparent in order to be able to emit the light formed. The material used for the anode (1) is preferably ITO.

Suitable hole conductor materials for layer (2) of the inventive OLEDs are disclosed, for example, in Kirk-Othmer Encyclopedia of Chemical Technology, 4th edition, Vol. 18, pages 837 to 860, 1996. Both hole-transporting molecules and polymers can be used as the hole transport material. Hole-transporting molecules typically used are selected from the group consisting of tris[N-(1-naphthyl)-N-(phenylamino)]triphenylamine (1-NaphDATA), 4,4'-bis[N-(1-naphthyl)-N-phenylamino]biphenyl (α-NPD), N,N'-diphenyl-N,N'-bis(3-methylphenyl)-[1,1'-biphenyl]-4,4'-diamine (TPD), 1,1-bis[(di-4-tolylamino)-phenyl]cyclohexane (TAPC), N,N'-bis(4-methylphenyl)-N,N'-bis(4-ethylphenyl)-[1,1'-(3,3'-dimethyl)biphenyl]-4,4'-diamine (ETPD), tetrakis(3-methylphenyl)-N,N,'N'-2,5-phenylenediamine (PDA), α-phenyl-4-N,N-diphenylaminostyrene (TPS), p-(diethylamino)benzaldehyde diphenylhydrazone (DEH), triphenylamine (TPA), bis[4-(N,N-diethylamino)-2-methylphenyl](4-methylphenyl)methane (MPMP), 1-phenyl-3-[p-(diethylamino)styryl]-5-[p-(diethylamino)phenyl]pyrazoline (PPR or DEASP), 1,2-trans-bis(9H-carbazol-9-yl)cyclobutane (DCZB), N,N,N',N'-tetrakis(4-methylphenyl)-(1,1'-biphenyl)-4,4'-diamine (TTB), 4,4',4"-tris(N,N-diphenylamino)triphenylamine (TDTA), 4,4',4"-tris(N-carbazolyl)triphenylamine (TCTA), N,N'-bis(naphthalen-2-yl)-N,N'-bis(phenyl)benzidine (β-NPB), N,N'-bis(3-methylphenyl)-N,N'-bis(phenyl)-9,9-spirobifluorene (Spiro-TPD), N,N'-bis(naphthalen-1-yl)-N,N'-bis(phenyl)-9,9-spirobifluorene (Spiro-NPB), N,N'-bis(3-methylphenyl)-N,N'-bis(phenyl)-9,9-dimethylfluorene (DMFL-TPD), di[4-(N,N-ditolylamino)phenyl]cyclohexane, N,N'-bis(naphthalen-1-yl)-N,N'-bis(phenyl)-9,9-dimethylfluorene, N,N'-bis(naphthalen-1-yl)-N,N'-bis(phenyl)-2,2-dimethylbenzidine, N,N'-bis(naphthalen-1-yl)-N,N'-bis(phenyl)benzidine, N,N'-bis(3-methylphenyl)-N,N'-bis(phenyl)benzidine, 2,3,5,6-tetrafluoro-7,7,8,8-tetracyanoquinodimethane (F4-TCNQ), 4,4',4"-tris(N-3- methylphenyl-N-phenylamino)triphenylamine, 4,4',4"-tris(N-(2-naphthyl)-N-phenyl-amino)triphenylamine, pyrazino[2,3-f][1,10]phenanthroline-2,3-dicarbonitrile (PPDN), N,N,N',N'-tetrakis(4-methoxyphenyl)benzidine (MeO-TPD), 2,7-bis[N,N-bis(4-methoxyphenyl)amino]-9,9-spirobifluorene (MeO-Spiro-TPD), 2,2'-bis[N,N-bis(4-methoxyphenyl)amino]-9,9-spirobifluorene (2,2'-MeO-Spiro-TPD), N,N'-diphenyl-N,N'-di[4-(N,N-ditolylamino)phenyl]benzidine (NTNPB), N,N'-diphenyl-N,N'-di[4-(N,N-diphenylamino)phenyl]benzidine (NPNPB), N,N'-di(naphthalen-2-yl)-N,N'-diphenylbenzene-1,4-diamine (β-NPP), N,N'-bis(3-methylphenyl)-N,N'-bis(phenyl)-9,9-diphenylfluorene (DPFL-TPD), N,N'-bis(naphthalen-1-yl)-N,N'-bis(phenyl)-9,9-diphenylfluorene (DPFL-NPB), 2,2',7,7'-tetrakis(N,N-diphenylamino)-9,9'-spirobifluorene (Spiro-TAD), 9,9-bis[4-(N,N-bis(biphenyl-4-yl)amino)phenyl]-9H-fluorene (BPAPF), 9,9-bis[4-(N,N-bis(naphthalen-2-yl)amino)phenyl]-9H-fluorene (NPAPF), 9,9-bis[4-(N,N-bis(naphthalen-2-yl)-N,N'-bisphenylamino)phenyl]-9H-fluorene (NPBAPF), 2,2',7,7'-tetrakis[N-naphthalenyl(phenyl)amino]-9,9'-spirobifluorene (Spiro-2NPB), N,N'-bis(phenanthren-9-yl)-N,N'-bis(phenyl)benzidine (PAPB), 2,7-bis[N,N-bis(9,9-spirobifluoren-2-yl)amino]-9,9-spirobifluorene (Spiro-5), 2,2'-bis[N,N-bis(biphenyl-4-yl)amino]-9,9-spirobifluorene (2,2'-Spiro-DBP), 2,2'-bis(N,N-diphenylamino)-9,9-spirobifluorene (Spiro-BPA), 2,2',7,7'-tetra(N,N-ditolyl)aminospirobifluorene (Spiro-TTB), N,N,N',N'-tetranaphthalen-2-ylbenzidine (TNB), porphyrin compounds and phthalocyanines such as copper phthalocyanines and titanium oxide phthalocyanines. Hole-transporting polymers typically used are selected from the group consisting of polyvinylcarbazoles, (phenylmethyl)polysilanes and polyanilines. It is likewise possible to obtain hole-transporting polymers by doping hole-transporting molecules into polymers such as polystyrene and polycarbonate. Suitable hole-transporting molecules are the molecules already mentioned above.

In addition—in one embodiment—it is possible to use carbene complexes as hole conductor materials, the band gap of the at least one hole conductor material generally being greater than the band gap of the emitter material used. In the context of the present application, "band gap" is understood to mean the triplet energy. Suitable carbene complexes are, for example, carbene complexes as described in WO 2005/019373 A2, WO 2006/056418 A2, WO 2005/113704, WO 2007/115970, WO 2007/115981 and WO 2008/000727. One example of a suitable carbene complex is Ir(dpbic)₃ with the formula:

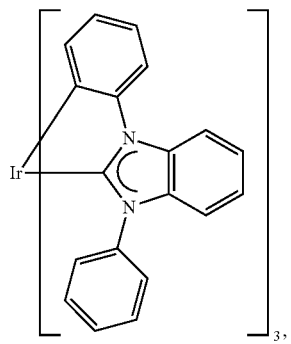

which is disclosed, for example, in WO2005/019373. In principle, it is possible that the hole conductor layer comprises at least one compound of the formula (I) or (I*) as hole conductor material.

The light-emitting layer (3) comprises at least one emitter material. In principle, it may be a fluoroescence or phosphorescence emitter, suitable emitter materials being known to those skilled in the art. The at least one emitter material is preferably a phosphorescence emitter. The phosphorescence emitter compounds used with preference are based on metal complexes, and especially the complexes of the metals Ru, Rh, Ir, Pd and Pt, in particular the complexes of Ir, have gained significance. The compounds of the formula (I) or (I*) or an inventive crosslinked or polymerized material can be used as the matrix in the light-emitting layer.

Suitable metal complexes for use in the inventive OLEDs are described, for example, in documents WO 02/60910 A1, US 2001/0015432 A1, US 2001/0019782 A1, US 2002/0055014 A1, US 2002/0024293 A1, US 2002/0048689 A1, EP 1 191 612 A2, EP 1 191 613 A2, EP 1 211 257 A2, US 2002/0094453 A1, WO 02/02714 A2, WO 00/70655 A2, WO 01/41512 A1, WO 02/15645 A1, WO 2005/019373 A2, WO 2005/113704 A2, WO 2006/115301 A1, WO 2006/067074 A1, WO 2006/056418, WO 2006121811 A1, WO 2007095118 A2, WO 2007/115970, WO 2007/115981 and WO 2008/000727.

Further suitable metal complexes are the commercially available metal complexes tris(2-phenylpyridine)indium(III), iridium(III) tris(2-(4-tolyl)pyridinato-N,C$^{2'}$), bis(2-phenylpyridine)(acetylacetonato)indium(III), indium(III) tris(1-phenylisoquinoline), indium(III) bis(2,2'-benzothienyl)pyridinato-N,C$^{3'}$)(acetylacetonate), tris(2-phenylquinoline)indium(III), indium(III) bis(2-(4,6-difluorophenyl)pyridinato-N,C$^{2}$)picolinate, indium(III) bis(1-phenylisoquinoline)(acetylacetonate), bis(2-phenylquinoline)(acetylacetonato)iridium(III), indium(III) bis(dibenzo[f,h]quinoxaline)(acetylacetonate), iridium(III) bis(2-methyldibenzo[f,h]quinoxaline)(acetylacetonate) and tris(3-methyl-1-phenyl-4-trimethylacetyl-5-pyrazolino)terbium(III), bis[1-(9,9-dimethyl-9H-fluoren-2-yl)isoquinoline](acetyl-bis(2-phenylbenzothiazolato)(acetylacetonato)indium(III), bis(2-(9,9-dihexylfluorenyl)-1-pyridine)(acetylacetonato)iridium(III), bis(2-benzo[b]thiophen-2-yl-pyridine)(acetylacetonato)iridium(III).

In addition, the following commercially available materials are suitable: tris(dibenzoylacetonato)mono(phenanthroline)europium(III), tris(dibenzoylmethane)-mono(phenanthroline)europium(III), tris(dibenzoylmethane)mono(5-aminophenanthroline)europium(III), tris(di-2-naphthoylmethane)mono(phenanthroline)europium(III), tris(4-bromobenzoylmethane)mono(phenanthroline)europium(III), tris(di(biphenyl)methane)mono(phenanthroline)europium(III), tris(dibenzoylmethane)mono(4,7-diphenylphenanthroline)europium(III), tris(dibenzoylmethane)mono(4,7-di-methylphenanthroline)europium(III), tris(dibenzoylmethane)mono(4,7-dimethylphenanthrolinedisulfonic acid)europium(III) disodium salt, tris[di(4-(2-(2-ethoxyethoxy)ethoxy)benzoylmethane)]mono(phenanthroline)europium(III) and tris[d][4-(2-(2-ethoxy-ethoxy)ethoxy)benzoylmethane)]mono(5-aminophenanthroline)europium(III), osmium(II) bis(3-(trifluoromethyl)-5-(4-tert-butylpyridyl)-1,2,4-triazolato)diphenylmethylphosphine, osmium(II) bis(3-(trifluoromethyl)-5-(2-pyridyl)-1,2,4-triazole)dimethylphenylphosphine, osmium(II) bis(3-(trifluoromethyl)-5-(4-tert-butylpyridyl)-1,2,4-triazolato)dimethylphenylphosphine, osmium(II) bis(3-(trifluoromethyl)-5-(2-pyridyl)pyrazolato)dimethylphenylphosphine, tris[4,4'-di-tert-butyl(2,2')-bipyridine]-ruthenium(III), osmium(II) bis(2-(9,9-dibutylfluorenyl)-1-isoquinoline(acetylacetonate).

Suitable triplet emitters are, for example, carbene complexes. In one embodiment of the present invention, the compounds of the formula (I) or (I*) or (Ib) are used in the light-emitting layer as matrix material together with carbene complexes as triplet emitters. Suitable carbene complexes are known to those skilled in the art and are described, for example, in WO 2005/019373 A2, WO 2006/056418 A2, WO 2005/113704, WO 2007/115970, WO 2007/115981 and WO 2008/000727.

The light-emitting layer may comprise further components in addition to the emitter material. For example, a fluorescent dye may be present in the light-emitting layer in order to alter the emission color of the emitter material. In addition—in a preferred embodiment—a matrix material can be used. This matrix material may be a polymer, for example poly(N-vinylcarbazole) or polysilane. The matrix material may, however, be a small molecule, for example 4,4'-N,N'-dicarbazolebiphenyl (CDP=CBP) or tertiary aromatic amines, for example TCTA. In a preferred embodiment of the present invention, at least one compound of the formula (I) or (I*) is used as matrix material.

In a preferred embodiment, the light-emitting layer is formed from 2 to 20% by weight, preferably 5 to 17% by weight, of at least one of the aforementioned emitter materials and 80 to 98% by weight, preferably 83 to 95% by weight, of at least one of the aforementioned matrix materials—in one embodiment at least one compound of the formula (I) or (I*) or an inventive crosslinked or polymerized material—where the sum total of the emitter material and of the matrix material adds up to 100% by weight.

In a further embodiment, the compounds of the formula (I) or (I*) or an inventive crosslinked or polymerized material are used as hole/exciton blocker material, preferably together with carbene complexes as triplet emitters. The compounds of the formula (I) or (I*) or an inventive crosslinked or polymerized material may additionally—as mentioned above—be used as matrix materials or both as matrix materials and as hole/exciton blocker materials together with carbene complexes as triplet emitters. In addition, it is possible that at least one compound of the formula (I) or (I*) or an inventive crosslinked or polymerized material is present in a blocking layer for holes/excitons, a blocking layer for electrons/excitons, a hole injection layer, a hole conductor layer, an electron injection layer and/or an electron conductor layer of the OLED, preferably together with carbene complexes as triplet emitters.

Suitable metal complexes for use together with the compounds of the formula (I) or (I*) or an inventive crosslinked or polymerized material as matrix material and/or hole/exciton blocker material and/or electron/exciton blocker material and/or hole injection material and/or electron injection material and/or hole conductor material and/or electron conductor material, preferably as matrix material and/or hole/exciton blocker material, in OLEDs are thus, for example, also carbene complexes as described in WO 2005/019373 A2, WO 2006/056418 A2, WO 2005/113704, WO 2007/115970, WO 2007/115981 and WO 2008/000727. Explicit reference is made here to the disclosure of the WO applications cited, and these disclosures shall be considered to be incorporated into the content of the present application.

If the blocking layer for holes/excitons (4) does not comprise any compounds of the formula (I) or (I*) or an inventive crosslinked or polymerized material, the OLED has—if a blocking layer for holes is present—hole blocker materials typically used in OLEDs, such as 2,6-bis(N-carbazolyl)pyridine (mCPy), 2,9-dimethyl-4,7-diphenyl-1,10-phenanthroline (bathocuproin, (BCP)), bis(2-methyl-8-quinolinato)-4-phenylphenylato)aluminum(III) (BAlq), phenothiazine S,S-dioxide derivates and 1,3,5-tris(N-phenyl-2-benzylimidazolyl)benzene) (TPBI), TPBI also being suitable as electron-conducting material. Further suitable hole blockers and/or electron conductor materials are 2,2',2"-(1,3,5-benzenetriyl)tris(1-phenyl-1-H-benzimidazole), 2-(4-biphenylyl)-5-(4-tert-butylphenyl)-1,3,4-oxadiazole, 8-hydroxyquinolinolatolithium, 4-(naphthalen-1-yl)-3,5-diphenyl-4H-1,2,4-triazole, 1,3-bis[2-(2,2'-bipyridin-6-yl)-1,3,4-oxadiazo-5-yl]benzene, 4,7-diphenyl-1,10-phenanthroline, 3-(4-biphenylyl)-4-phenyl-5-tert-butylphenyl-1,2,4-triazole, 6,6'-bis[5-(biphenyl-4-yl)-1,3,4-oxadiazo-2-yl]-2,2'-bipyridyl, 2-phenyl-9,10-di(naphthalene-2-yl)anthracene, 2,7-bis[2-(2,2'-bipyridin-6-yl)-1,3,4-oxadiazo-5-yl]-9,9-dimethylfluorene, 1,3-bis[2-(4-tert-butylphenyl)-1,3,4-oxadiazo-5-yl]benzene, 2-(naphthalene-2-yl)-4,7-diphenyl-1,10-phenanthroline, tris(2,4,6-trimethyl-3-(pyridin-3-yl)phenyl)borane, 2,9-bis(naphthalene-2-yl)-4,7-diphenyl-1,10-phenanthroline, 1-methyl-2-(4-(naphthalene-2-yl)phenyl)-1H-imidazo[4,5-f][1, 10]-phenanthroline. In a further embodiment, it is possible to use compounds which comprise aromatic or heteroaromatic rings joined via groups comprising carbonyl groups, as disclosed in WO2006/100298, disilyl compounds selected from the group consisting of disilylcarbazoles, disilylbenzofurans, disilylbenzothiophenes, disilylbenzophospholes, disilylbenzothiophene S-oxides and disilylbenzothiophene S,S-dioxides, as specified, for example, in PCT applications WO 2009/003919 and WO 2009/000872, and disilyl compounds as disclosed in WO2008/034758, as a blocking layer for holes/excitons (4) or as matrix materials in the light-emitting layer (3).

In a preferred embodiment, the present invention relates to an inventive OLED comprising the layers (1) anode, (2) hole conductor layer, (3) light-emitting layer, (4) blocking layer for holes/excitons, (5) electron conductor layer and (6) cathode, and if appropriate further layers, wherein the blocking layer for holes/excitons or the light-emitting layer comprises at least one compound of the formula (I) or (I*) or (Ib).

In a further preferred embodiment, the present invention relates to an inventive OLED comprising the layers (1) anode, (2) hole conductor layer, (3) light-emitting layer, (4) blocking layer for holes/excitons, (5) electron conductor layer and (6) cathode, and if appropriate further layers, wherein the light-emitting layer (3) comprises at least one compound of the formula (I) or (I*) or (Ib) and the blocking layer for holes/excitons comprises at least one compound of the formula (I) or (I*) or (Ib).

Suitable electron conductor materials for the layer (5) of the inventive OLEDs comprise metals chelated to oxinoid compounds, such as 2,2',2"-(1,3,5-phenylene)tris[1-phenyl-1H-benzimidazole] (TPBI), tris(8-quinolinolato)aluminum ($Alq_3$), compounds based on phenanthroline, such as 2,9-dimethyl-4,7-diphenyl-1,10-phenanthroline (DDPA=BCP) or 4,7-diphenyl-1,10-phenanthroline (DPA), and azole compounds such as 2-(4-biphenylyl)-5-(4-t-butylphenyl)-1,3,4-oxadiazole (PBD) and 3-(4-biphenylyl)-4-phenyl-5-(4-t-butylphenyl)-1,2,4-triazole (TAZ), 8-hydroxyquinolinolatolithium (Liq), 4,7-diphenyl-1,10-phenanthroline (BPhen), bis(2-methyl-8-quinolinolato)-4-(phenylphenolato)-aluminum (BAIq), 1,3-bis[2-(2,2'-bipyridin-6-yl)-1,3,4-oxadiazo-5-yl]benzene (Bpy-OXD), 6,6'-bis[5-(biphenyl-4-yl)-1,3,4-oxadiazo-2-yl]-2,2'-bipyridyl (BP-OXD-Bpy), 4-(naphthalen-1-yl)-3,5-diphenyl-4H-1,2,4-triazole (NTAZ), 2,9-bis(naphthalen-2-yl)-4,7-diphenyl-1,10-phenanthroline (NBphen), 2,7-bis[2-(2,2'-bipyridin-6-yl)-1,3,4-oxadiazo-5-yl]-9,9-dimethylfluorene (Bby-FOXD), 1,3-bis[2-(4-tert-butylphenyl)-1,3,4-oxadiazo-5-yl]benzene (OXD-7), tris(2,4,6-trimethyl-3-(pyridin-3-yl)phenyl)borane (3TPYMB), 1-methyl-2-(4-(naphthalen-2-yl)phenyl)-1H-imidazo[4,5-f][1,10]phenanthroline (2-NPIP), 2-phenyl-9,10-di(naphthalen-2-yl)anthracene (PADN), 2-(naphthalen-2-yl)-4,7-diphenyl-1,10-phenanthroline (HN-Bphen). The layer (5) may serve both to facilitate electron transport and as a buffer layer or barrier layer in order to prevent quenching of the exciton at the interfaces of the layers of the OLED. The layer (5) preferably improves the mobility of the electrons and reduces quenching of the exciton. In a preferred embodiment, TPBI is used as the electron conductor material. In principle, it is possible that the electron conductor layer comprises at least one compound of the formula (I) or (I*) or an inventive crosslinked or polymerized material as electron conductor material.

Among the materials mentioned above as hole conductor materials and electron conductor materials, some may fulfil several functions. For example, some of the electron-conducting materials are simultaneously hole-blocking materials when they have a low-lying HOMO. These can be used, for example, in the blocking layer for holes/excitons (4). However, it is likewise possible that the function as a hole/exciton blocker is also adopted by the layer (5), such that the layer (4) can be dispensed with.

The charge transport layers can also be electronically doped in order to improve the transport properties of the materials used, in order firstly to make the layer thicknesses more generous (avoidance of pinholes/short circuits) and in order secondly to minimize the operating voltage of the device. p-Doping is achieved by the addition of oxidizing materials. These mixtures may, for example, be mixtures of the abovementioned hole transport materials with $MoO_2$, $MoO_3$, $WO_x$, $ReO_3$, $V_2O_5$, 7,7,8,8-tetracyanoquinodimethane (TCNQ), 2,3,5,6-tetrafluoro-7,7,8,8-tetracyanoquinodimethane ($F_4$-TCNQ), 2,5-bis(2-hydroxyethoxy)-7,7,8,8-tetracyanoquinodimethane, bis(tetra-n-butylammonium)tetracyanodiphenoquinodimethane, 2,5-dimethyl-7,7,8,8-tetracyanoquinodimethane, tetracyanoethylene, 11,11,12,12-tetracyanonaphtho-2,6-quinodimethane, 2-fluoro-7,7,8,8-tetracyanoquinodimethane, 2,5-difluoro-7,7,8,8-tetracyanoquinodimethane, dicyanomethylene-1,3,4,5,7,8-hexafluoro-6H-naphthalen-2-ylidene)malononitrile ($F_6$-TNAP), Mo(tfd)$_3$ (from Kahn et al., J. Am. Chem. Soc. 2009, 131 (35), 12530-12531), and with quinone compounds as mentioned in EP 09153776.1.

The electron conductor materials can be doped, for example, with alkali metals, for example $Alq_3$ with lithium. In addition, electron conductors can be doped with salts such as $Cs_2CO_3$. Electronic doping is known to those skilled in the art and is disclosed, for example, in W. Gao, A. Kahn, J. Appl. Phys., Vol. 94, No. 1, 1 Jul. 2003 (p-doped organic layers); A. G. Werner, F. Li, K. Harada, M. Pfeiffer, T. Fritz, K. Leo. Appl. Phys. Lett., Vol. 82, No. 25, 23 Jun. 2003 and Pfeiffer et al., Organic Electronics 2003, 4, 89-103. For example, the hole conductor layer may, in addition to a carbene complex, e.g. Ir(dpbic)$_3$, be doped with $MoO_3$ or $WO_3$.

The cathode (6) is an electrode which serves to introduce electrons or negative charge carriers. Suitable materials for the cathode are selected from the group consisting of alkali metals of group Ia, for example Li, Cs, alkaline earth metals of group IIa, for example calcium, barium or magnesium, metals of group IIb of the periodic table of the elements (old IUPAC version), comprising the lanthanides and actinides, for example samarium. In addition, it is also possible to use metals such as aluminum or indium, and combinations of all metals mentioned. In addition, lithium-comprising organometallic compounds or LiF can be applied between the organic layer and the cathode in order to reduce the operating voltage.

The OLED according to the present invention may additionally comprise further layers which are known to those skilled in the art. For example, a layer which facilitates the transport of the positive charge and/or matches the band gaps of the layers to one another may be applied between the layer (2) and the light-emitting layer (3). Alternatively, this further layer may serve as a protective layer. In an analogous manner, additional layers may be present between the light-emitting layer (3) and the layer (4) in order to facilitate the transport of negative charge and/or to match the band gaps between the layers to one another. Alternatively, this layer may serve as a protective layer.

In a preferred embodiment of the inventive OLED, all layers, i.e. hole conductor, electron blocker, matrix, hole blocker and electron conductor, consist of materials of the formula (I) or (I*) or an inventive crosslinked or polymerized material; only the emission layer additionally comprises at least one emitter.

In a preferred embodiment, the inventive OLED, in addition to layers (1) to (6), comprises at least one of the following layers mentioned below:
  a hole injection layer between the anode (1) and the hole-transporting layer (2);
  a blocking layer for electrons between the hole-transporting layer (2) and the light-emitting layer (3);
  an electron injection layer between the electron-transporting layer (5) and the cathode (6).

Materials for a hole injection layer may be selected from copper phthalocyanine, 4,4',4"-tris(N-3-methylphenyl-N-phenylamino)triphenylamine (m-MTDATA), 4,4',4"-tris-(N-(2-naphthyl)-N-phenylamino)triphenylamine (2T-NATA), 4,4',4"-tris(N-(1-naphthyl)-N-phenylamino)triphenylamine (1T-NATA), 4,4',4"-tris(N,N-diphenylamino)triphenylamine (NATA), titanium oxide phthalocyanine, 2,3,5,6-tetrafluoro-7,7,8,8-tetracyanoquinodimethane (F4-TCNQ), pyrazino[2,3-f][1,10]phenanthroline-2,3-dicarbonitrile (PPDN), N,N,N',N'-tetrakis(4-methoxyphenyl)benzidine (MeO-TPD), 2,7-bis[N,N-bis(4-methoxyphenyl)amino]-9,9-spirobifluorene (MeO-Spiro-TPD), 2,2'-bis[N,N-bis(4-methoxyphenyl)amino]-9,9-spirobifluorene (2,2'-MeO-Spiro-TPD), N,N'-diphenyl-N,N'-di-[4-(N,N-ditolylamino)phenyl]benzidine (NTNPB), N,N'-diphenyl-N,N'-di-[4-(N,N-diphenylamino)phenyl]benzidine (NPNPB), N,N'-di(naphthalen-2-yl)-N,N'-diphenylbenzene-1,4-diamine (β-NPP). In principle, it is possible that the hole injection layer comprises at least one compound of the formula (I) or (I*) as hole injection material.

As a material for the electron injection layer, LiF, CsF or $Cs_2CO_3$, for example, can be selected. In principle, it is possible that the electron injection layer comprises at least one compound of the formula (I) or (I*) or an inventive crosslinked or polymerized material as electron injection material.

The person skilled in the art is aware (for example on the basis of electrochemical studies) of how suitable materials have to be selected. Suitable materials for the individual layers are known to those skilled in the art and are disclosed, for example, in WO 00/70655.

In addition, it is possible that some of the layers used in the inventive OLED have been surface-treated in order to increase the efficiency of charge carrier transport. The selection of the materials for each of the layers mentioned is preferably determined by obtaining an OLED with a high efficiency and lifetime.

The inventive OLED can be produced by methods known to those skilled in the art. In general, the inventive OLED is produced by successive vapor deposition of the individual layers onto a suitable substrate. Suitable substrates are, for example, glass, inorganic semiconductors or polymer films. For vapor deposition, it is possible to use customary techniques, such as thermal evaporation, chemical vapor deposition (CVD), physical vapor deposition (PVD) and others. In an alternative process, the organic layers of the OLED can be applied from solutions or dispersions in suitable solvents, employing coating techniques known to those skilled in the art.

In general, the different layers have the following thicknesses: anode (1) 50 to 500 nm, preferably 100 to 200 nm; hole-conducting layer (2) 5 to 100 nm, preferably 20 to 80 nm, light-emitting layer (3) 1 to 100 nm, preferably 10 to 80 nm, blocking layer for holes/excitons (4) 2 to 100 nm, preferably 5 to 50 nm, electron-conducting layer (5) 5 to 100 nm, preferably 20 to 80 nm, cathode (6) 20 to 1000 nm, preferably 30 to 500 nm. The relative position of the recombination zone of holes and electrons in the inventive OLED in relation to the cathode and hence the emission spectrum of the OLED can be influenced, among other factors, by the relative thickness of each layer. This means that the thickness of the electron transport layer should preferably be selected such that the position of the recombination zone is matched to the optical resonator property of the diode and hence to the emission wavelength of the emitter. The ratio of the layer thicknesses of the individual layers in the OLED depends on the materials used. The layer thicknesses of any additional layers used are known to those skilled in the art. It is possible that the electron-conducting layer and/or the hole-conducting layer have greater thicknesses than the layer thicknesses specified when they are electrically doped.

Use of the compounds of the formula (I) or (I*) or an inventive crosslinked or polymerized material in at least one layer of the OLED, preferably in the light-emitting layer (preferably as a matrix material) and/or in the blocking layer for holes/excitons makes it possible to obtain OLEDs with high efficiency and with low use and operating voltage. Frequently, the OLEDs obtained by the use of the compounds of the formula (I) additionally have high lifetimes. The efficiency of the OLEDs can additionally be improved by optimizing the other layers of the OLEDs. For example, high-efficiency cathodes such as Ca or Ba, if appropriate in combination with an intermediate layer of LiF, CsF or $Cs_2CO_3$, can be used. Shaped substrates and novel hole-transporting materials which bring about a reduction in the operating voltage or an increase in the quantum efficiency are likewise usable in the inventive OLEDs. Moreover, additional layers may be present in the OLEDs in order to adjust the energy level of the different layers and to facilitate electroluminescence.

The OLEDs may further comprise at least one second light-emitting layer. The overall emission of the OLEDs may be composed of the emission of the at least two light-emitting layers and may also comprise white light.

The OLEDs can be used in all apparatus in which electroluminescence is useful. Suitable devices are preferably selected from stationary and mobile visual display units and illumination units. Stationary visual display units are, for example, visual display units of computers, televisions, visual display units in printers, kitchen appliances and advertising panels, illuminations and information panels. Mobile visual display units are, for example, visual display units in cellphones, laptops, digital cameras, MP3 players, vehicles and destination displays on buses and trains. Further devices in which the inventive OLEDs can be used are, for example, keyboards; items of clothing; furniture; wallpaper.

In addition, the compounds of the formula (I) or (I*) or an inventive crosslinked or polymerized material can be used in OLEDs with inverse structure. The compounds of the formula (I) or (I*) or an inventive crosslinked or polymerized material used in accordance with the invention are preferably used in these inverse OLEDs in turn as hole/exciton blocker materials. The structure of inverse OLEDs and the materials typically used therein are known to those skilled in the art.

In addition, the present invention relates to a device selected from the group consisting of stationary visual display units such as visual display units of computers, televisions, visual display units in printers, kitchen appliances and advertising panels, illuminations, information panels, and mobile visual display units such as visual display units in cellphones, laptops, digital cameras, MP3 players, vehicles and destination displays on buses and trains; illumination units; keyboards; items of clothing; furniture; wallpaper, comprising at least one inventive organic light-emitting diode or at least one inventive light-emitting layer.

The examples which follow provide additional illustration of the invention.

Synthesis Examples

Synthesis Example 1

Synthesis of 3-bromo-9-phenyl-6-triphenylsilylcarbazole (Compound 1)

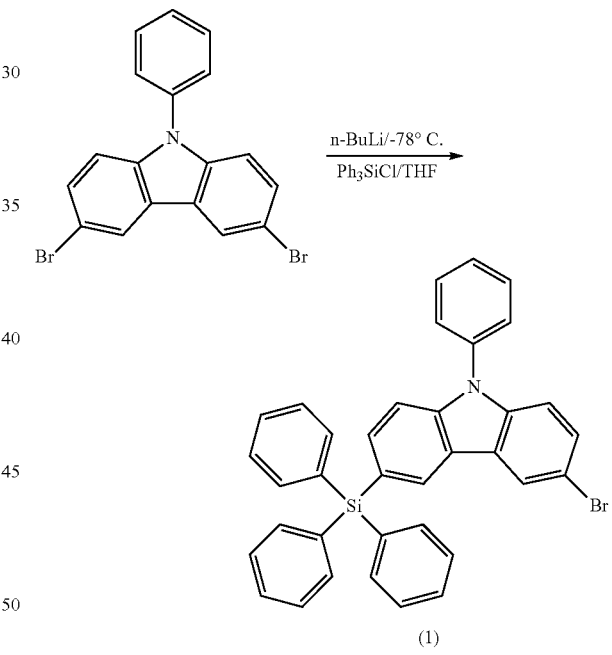

(1)

A solution of 9-(3-methoxyphenyl)-3,6-dibromo-9H-carbazole (26 g, 1 eq) in dry THF (700 ml) is admixed, at −78° C. under argon, gradually with n-butyllithium (1.6 M in hexane, 41 ml, 1 eq), and stirred at −78° C. for 2 h. After a solution of chlorotriphenylsilane (30 g, 1.5 eq) in dry THF (150 ml) has been added at −78° C., the mixture is warmed to room temperature overnight with stirring. Excess butyllithium is hydrolyzed with saturated ammonium chloride solution. The precipitated product is filtered off and washed thoroughly with methylene chloride. The combined methylene chloride filtrates are extracted with water and concentrated to dryness. The residue is stirred with acetone and filtered off. Yield 74%.

$^1$H NMR (CDCl$_3$, 400 MHz):

δ=8.15 (s, 1H), 8.28 (s, 1H), 7.3-7.7 (m, 24H).

Synthesis Example 2

Synthesis of 3-diphenylphosphinyl-9-phenyl-6-triphenylsilylcarbazole (Compound 2)

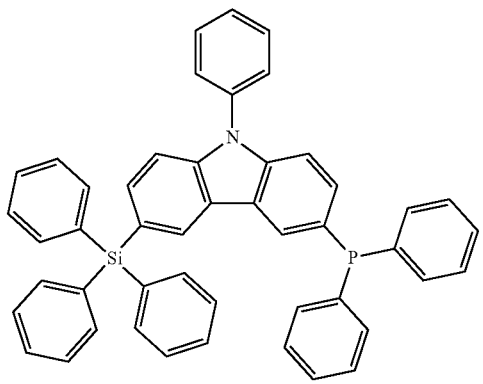

2

A solution of 3-bromo-9-phenyl-6-triphenylsilylcarbazole 1 (5.0 g, 8.6 mmol) in dry THF (80 ml) is admixed, at −78° C. under argon, gradually with n-butyllithium (1.6 M in hexane, 6.7 ml, 11 mmol), and stirred at −78° C. for 1.5 h. After a solution of chlorodiphenylphosphine (2.85 g, 12.9 mmol) in dry THF (25 ml) has been added at −78° C., the mixture is warmed to room temperature with stirring overnight. EtOH (20 ml) is added to the suspension. The precipitated product is filtered off, washed with EtOH and dried. Yield 82%. The product is converted further without purification.

Synthesis Example 3

Synthesis of 3-diphenylphosphinoyl-9-phenyl-6-triphenylsilylcarbazole (Compound 3)

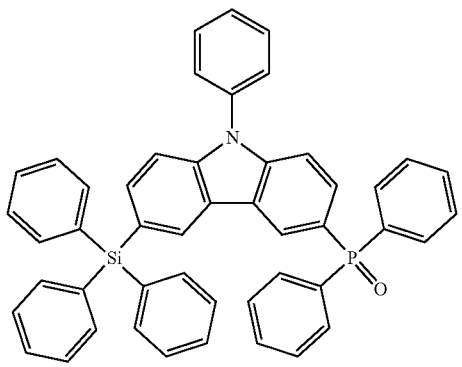

3

To a solution of compound 2 (3.5 g, 5.1 mmol) in methylene chloride (200 ml) is added 70% m-chloroperbenzoic acid (1.8 g, 7.4 mmol) in portions. The reaction solution is stirred at room temperature for 48 h. The organic phase is washed with 10% sodium hydroxide solution (3×50 ml), 5% hydrochloric acid (2×50 ml) and with saturated sodium hydrogencarbonate solution (80 ml), and concentrated. The residue is digested in ethanol, filtered and dried. FC (SiO$_2$, CH$_2$Cl$_2$ to 97:3 CH$_2$Cl$_2$/MeOH) gives the product 3 (2.3 g, 64%).

$^1$H NMR (CDCl$_3$, 400 MHz): δ=7.3-7.7 (m, 34H), 8.30 (s, 1H), 8.52 (d, 1H).

Synthesis Example 4

Synthesis of Compound 4

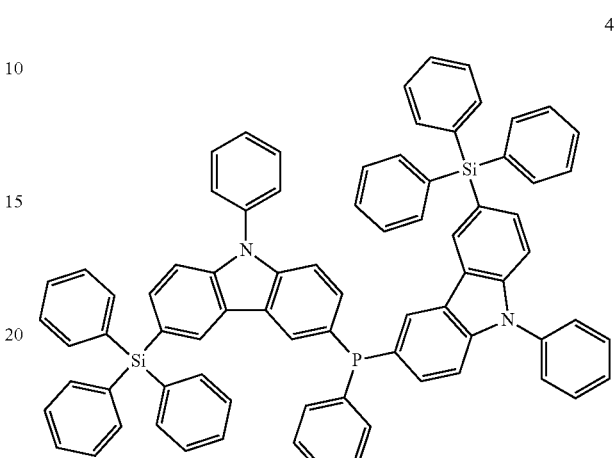

4

A solution of 3-bromo-9-phenyl-6-triphenylsilylcarbazole 1 (6.4 g, 11 mmol) in dry THF (100 ml) is admixed, at −78° C. under argon, slowly with n-butyllithium (1.6 M in hexane, 8.6 ml, 14 mmol), and stirred at −78° C. for 1 h. After a solution of dichlorophenylphosphine (0.92 g, 5.1 mmol) in dry THF (15 ml) has been added slowly at −78° C., the mixture is warmed to room temperature with stirring overnight. The solution is admixed with sat. NH$_4$Cl solution (20 ml) and stirred for 30 min. The precipitate is filtered off and washed with CH$_2$Cl$_2$. The organic phase is washed with water (4×75 ml), dried over Na$_2$SO$_4$ and concentrated. The solid is suspended in EtOH and filtered off. Yield 3.73 g (67%). The product 4 is converted further without purification.

MALDI-MS: m/z: 1108 (M$^+$), 1165 ([M+K$^+$ O]$^+$)

Synthesis Example 5

Synthesis of Compound 5

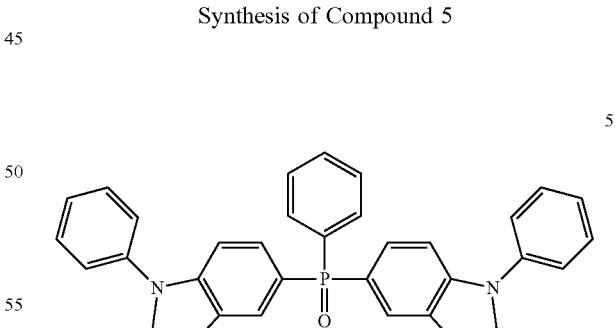

5

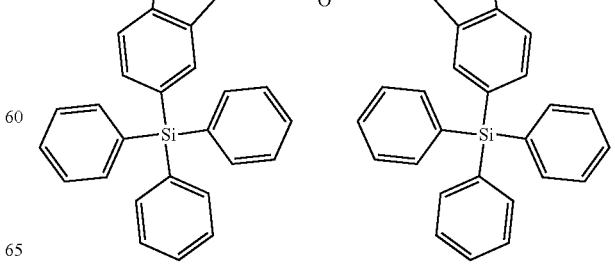

To a suspension of product 4 (3.7 g, 3.4 mmol) in methylene chloride (100 ml) is added 70% m-chloroperbenzoic acid (0.91 g, 3.7 mmol) in portions. The reaction solution is stirred at room temperature for 18 h. The organic phase is washed with 10% sodium hydroxide solution (4×40 ml), 5% hydrochloric acid (3×40 ml) and with saturated sodium hydrogencarbonate solution (30 ml), and concentrated. FC (SiO$_2$, 2:1 ethyl acetate/cyclohexane) and digestion in acetone give the product 5 (1.5 g, 41%).

$^1$H NMR (CDCl$_3$, 400 MHz): δ=7.45 (m, 24H), 7.6 (m, 27H), 7.68 (dd, 2H), 8.28 (s, 2H), 8.54 (d, 2H).

Synthesis Example 6

Synthesis of Compound 6

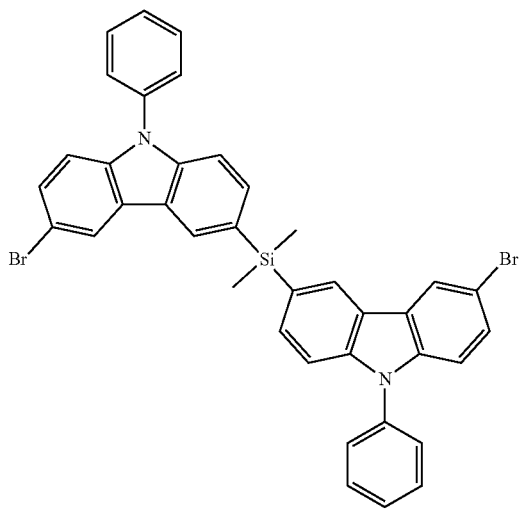

6

A solution of 9-phenyl-3,6-dibromo-9H-carbazole (12 g, 1 eq) in dry THF (230 ml) is admixed, at −78° C. under argon, gradually with n-butyllithium (1.6 m in hexane, 18.8 ml, 1 eq), and stirred at −78° C. for 1.5 h. After a solution of dichlorodimethylsilane (1.9 g, 0.5 eq) in dry THF (20 ml) has been added at −78° C., the mixture is warmed to room temperature with stirring overnight. Excess butyllithium is hydrolyzed with saturated ammonium chloride solution. The precipitated product is filtered off and washed thoroughly with CH$_2$Cl$_2$. Column chromatography (SiO$_2$, 10:1 hexane/EtOAc) gives the product 6. Yield 74%. $^1$H NMR (CDCl$_3$, 400 MHz): δ=0.7 (s, 6H), 7.25 (dd, 4H), 7.40 (d, 2H), 7.42-7.50 (m, 6H), 7.55-7.65 (m, 6H) 8.22 (s, 2H), 8.30 (s, 2H).

Synthesis Example 7

Synthesis of Compound 7

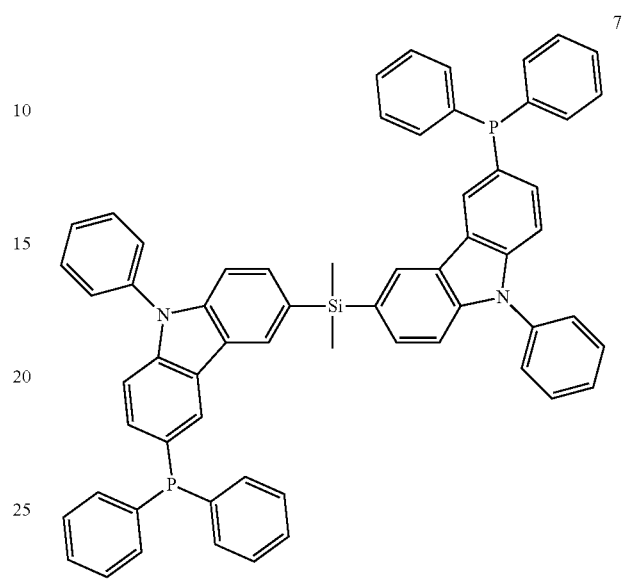

7

A solution of compound 6 (4.2 g, 6.0 mmol) in dry THF (100 ml) is admixed, at −78° C. under argon, gradually with n-butyllithium (1.6 m in hexane, 9.4 ml, 15 mmol), and stirred at −78° C. for 1.5 h. After a solution of chlorodiphenylphosphine (3.4 g, 15 mmol) in dry THF (20 ml) has been added at −78° C., the mixture is warmed to room temperature with stirring overnight. The solution is admixed with sat. NH$_4$Cl solution (25 ml) and stirred for 30 min. The precipitate is filtered off and washed with CH$_2$Cl$_2$. The organic phase is washed with water (4×100 mL), dried over Na$_2$SO$_4$ and concentrated. The solid is suspended in MeOH and filtered off. Yield: 4.4 g (80%). The product 7 is converted further without purification.

Synthesis Example 8

Synthesis of Compound 8

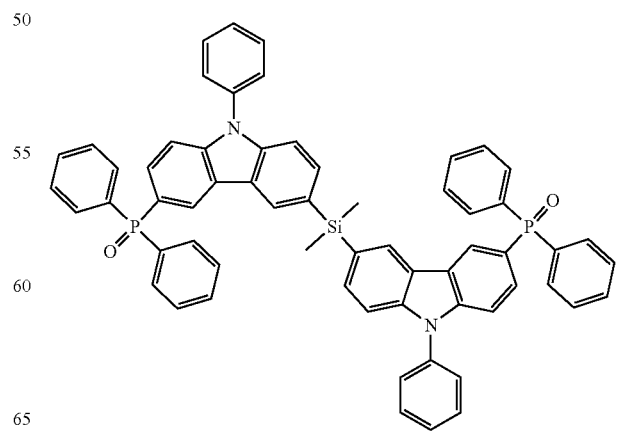

8

To a solution of product 7 (4.5 g, 4.9 mmol) in methylene chloride (120 ml) is added 70% m-chloroperbenzoic acid (3.1 g, 12 mmol) in portions. The reaction solution is stirred at room temperature for 18 h. The organic phase is washed with 10% sodium hydroxide solution (3×50 ml), 5% hydrochloric acid (3×50 ml) and with saturated sodium hydrogencarbonate solution (30 ml), and concentrated. FC (SiO$_2$, CH$_2$Cl$_2$ to 99:1 CH$_2$Cl$_2$/MeOH) gives the product 8 (2.2 g, 48%).

$^1$H NMR (CDCl$_3$, 400 MHz): δ=0.70 (s, 6H), 7.35-7.55 (m, 24H), 7.60 (m, 6H), 7.70 (m, 8H), 8.28 (s, 2H), 8.54 (d, 2H).

Synthesis Example 9

Synthesis of Compound 9

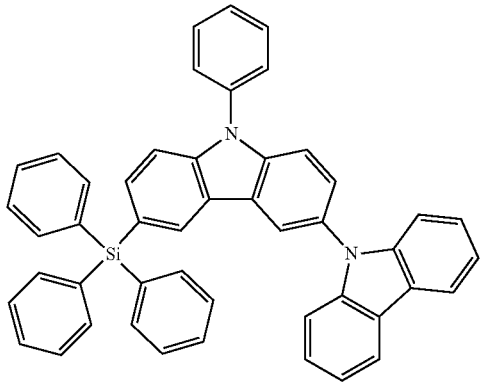

9

Carbazole (95%, 1.1 g, 6.0 mmol), compound 1 (7.0 g, 12 mmol), potassium carbonate (2.1 g, 15 mmol) and copper powder (80 mg, 1.3 mmol) are heated to 180° C. and stirred at this temperature for 60 h. After cooling to room temperature, the mixture is extracted with methylene chloride. FC (SiO$_2$, 8:1 to 6:1 cyclohexane/CH$_2$Cl$_2$) gives the product 9 (2.1 g, 53%).

$^1$H NMR (CDCl$_3$, 400 MHz): δ=7.2-7.4 (m, 15H), 7.5 (m, 3H), 7.6-7.7 (m, 12H), 8.15 (m, 3H), 8.30 (s, 1H).

Synthesis Example 10

Synthesis of Compound 10

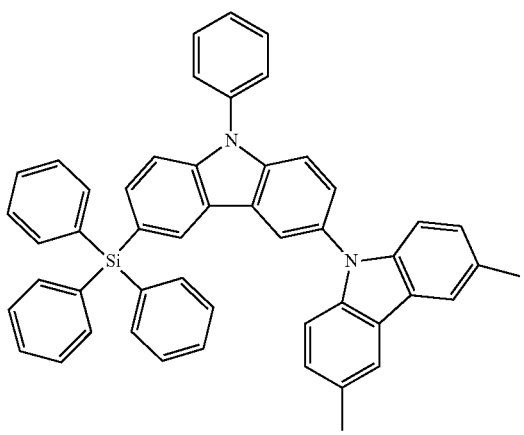

10

The synthesis of 3,6-dimethylcarbazole is described in *J. Chem. Soc.*, 1949, 1384-1388, *J. Org. Chem.*, 2003, 68, 2209-2215 and in *Dalton Trans.*, 2003, 13, 2718-2727.

3,6-dimethylcarbazole (1.1 g, 5.7 mmol), compound 1 (6.7 g, 12 mmol), potassium carbonate (2.0 g, 14 mmol) and copper powder (76 mg, 1.2 mmol) are heated to 180° C. and stirred at this temperature for 72 h. After cooling to room temperature, the mixture is extracted with methylene chloride. FC (SiO$_2$, 8:1 cyclohexane/CH$_2$Cl$_2$) gives the product 10 (1.2 g, 30%).

$^1$H NMR (CDCl$_3$, 400 MHz): δ=2.5 (s, 6H), 7.2 (m, 4H), 7.35 (m, 9H), 7.48 (m, 3H), 7.55 (d, 1H), 7.62 (m, 11H), 7.9 (s, 2H), 8.1 (s, 1H), 8.3 (s, 1H).

Synthesis Example 11

Synthesis of Compound 11

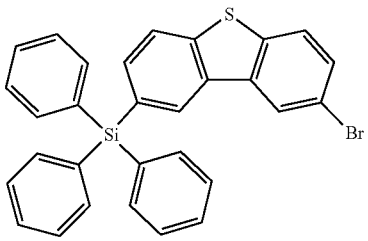

11

The synthesis of 2,8-dibromodibenzothiophene is described in W. Yang et al., *J. Mater. Chem.* 2003, 13, 1351.

A solution of 2,8-dibromodibenzothiophene (7.3 g, 21 mmol) in dry THF (215 ml) is admixed, at −78° C. under argon, gradually with n-butyllithium (1.6 m in hexane, 16.6 ml, 26.6 mmol), and stirred at −78° C. for 1.5 h. After a solution of triphenylchlorosilane (9.7 g, 32 mmol) in dry THF (25 ml) has been added slowly at −78° C., the mixture is warmed to room temperature overnight with stirring. The solution is admixed with sat. NH$_4$Cl solution (20 ml) and stirred for 30 min. The precipitate is filtered off and washed with CH$_2$Cl$_2$. The organic phase is washed with water (4×100 ml), dried over Na$_2$SO$_4$ and concentrated. FC (SiO$_2$, 20:1 cyclohexane/CH$_2$Cl$_2$) gives the product 11 (3.4 g, 31%).

$^1$H NMR (CDCl$_3$, 400 MHz): δ=7.40 (dd, 6H), 7.48 (t, 3H), 7.54 (d, 1H), 7.62 (d, 6H), 7.65 (d, 1H), 7.71 (d, 1H), 7.86 (d, 1H), 8.13 (s, 1H), 8.31 (s, 1H).

Synthesis Example 12

Synthesis of Compound 12

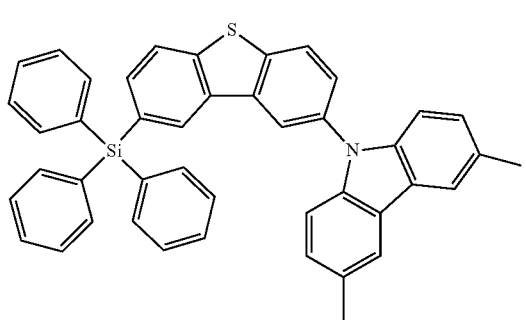

12

3,6-dimethylcarbazole (0.73 g, 3.8 mmol), compound 11 (2.3 g, 4.3 mmol), potassium carbonate (1.3 g, 9.5 mmol) and copper powder (48 mg, 0.76 mmol) are heated to 185° C. and stirred at this temperature for 48 h. After cooling to room temperature, the mixture is extracted with methylene chloride. The residue is suspended in EtOH, stirred for 24 h and filtered. FC (SiO$_2$, 9:1 cyclohexane/CH$_2$Cl$_2$) gives the product 12 (1.0 g, 43%).

MALDI-MS: m/z: 636 (M$^+$).

Synthesis Example 13

Synthesis of Compound 13

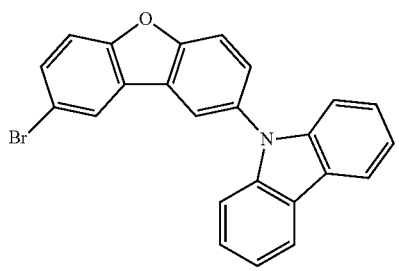

The synthesis of 2,8-dibromodibenzofuran is described, among other places, in *Org. Lett.*, 2006, 8, 4211-4214 and *J. Med. Chem.*, 1985, 28, 1728-1740.

2,8-dibromobenzofuran (16 g, 49 mmol), carbazole (95%, 8.6 g, 49 mmol), potassium carbonate (16.9 g, 123 mmol) and copper powder (622 mg, 9.8 mmol) in tridecane (50 ml) are heated to 185° C. and stirred at this temperature for 76 h. After cooling to room temperature, the mixture is extracted with methylene chloride. Tridecane is distilled off. Recrystallization from cyclohexane and FC (SiO$_2$, cyclohexane/CH$_2$Cl$_2$, 100:0 to 9:1) gives the product 13 (6.9 g, 34%).

$^1$H NMR (CDCl$_3$, 400 MHz): δ=7.26-7.45 (m, 6H), 7.54 (d, 1H), 7.60-7.68 (2× d, 2H), 7.78 (d, 1H), 8.08 (2×s, 2H), 8.18 (d, 2H).

Synthesis Example 14

Synthesis of Compound 14

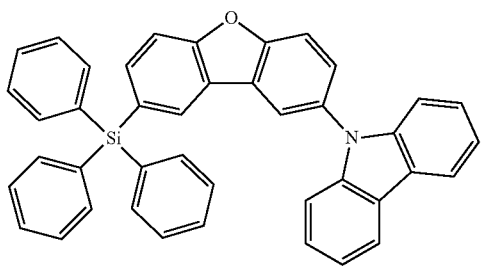

A solution of 13 (1.0 g, 2.4 mmol) in dry diethyl ether (5 ml) is admixed, under argon, gradually with n-butyllithium (1.6 m in hexane, 1.6 ml, 2.6 mmol), and stirred at reflux for 25 min. A solution of triphenylchlorosilane (2.2 g, 7.3 mmol) in dry diethyl ether (7.5 ml) is added dropwise under reflux and stirred under reflux for a further 30 min. The mixture is admixed with MeOH (5 ml) and diluted further with CH$_2$Cl$_2$. The organic phases are washed with water (3×25 ml), dried over Na$_2$SO$_4$ and concentrated. FC (RP-C18-SiO$_2$ MeCN/CH$_2$Cl$_2$ 7:3) gives product 14 (0.43 g, 30%).

$^1$H NMR (CDCl$_3$, 400 MHz): δ=8.16 (s, 1H), 8.13 (d, 2H), 8.00 (s, 1H), 7.77 (d, 1H), 7.73 (d, 1H), 7.66 (d, 1H), 7.59 (m, 7H), 7.39 (m, 11H), 7.31 (d, 2H), 7.26 (d, 2H).

Improved Synthesis of Compound 14:

A solution of 13 (11.0 g, 26.7 mmol) and triphenylchlorosilane (8.12 g, 26.7 mmol) in dry diethyl ether (85 ml) is admixed under argon slowly with n-butyllithium (1.6 M in hexane, 18.4 ml, 29.4 mmol) and stirred overnight. The mixture is admixed with MeOH and diluted further with CH$_2$Cl$_2$. The organic phases are washed with water, dried with Na$_2$SO$_4$ and concentrated. FC(RP-C18-SiO$_2$ MeCN/CH$_2$Cl$_2$ 7:3) or recrystallization from CH$_2$Cl$_2$/MeCN gives product 14 (10.6 g, 67%).

A secondary component which can be isolated in the synthesis of compound 14 is compound 34:

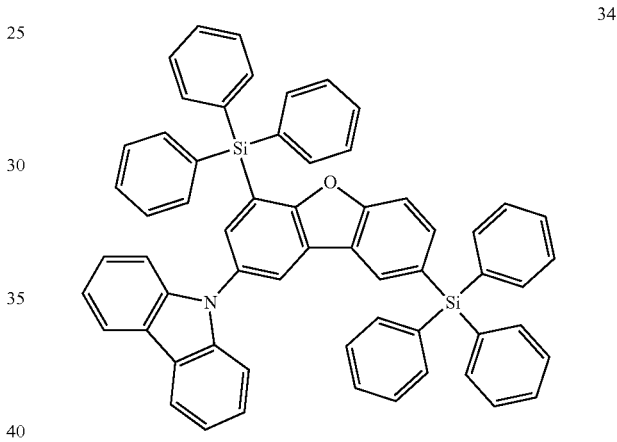

$^1$H NMR (CD$_2$Cl$_2$, 400 MHz): δ=7.20-7.50 (m, 26H), 7.58 (m, 9H), 7.65 (d, 1H), 7.95 (d, 3H), 8.10 (d, 2H), 8.14 (s, 1H), 8.19 (s, 1H).

Synthesis Example 15

Synthesis of Compound 15

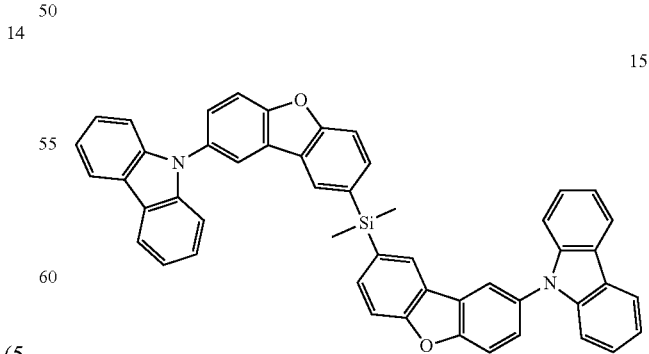

A solution of 13 (1.0 g, 2.4 mmol) and dichlorodimethylsilane (0.16 g) in dry diethyl ether (10 ml) is admixed, under argon, gradually with tert-butyllithium (1.7 m in pentane, 2.9 ml, 4.9 mmol), and stirred overnight. The mixture is admixed with MeOH (5 ml) and diluted further with CH$_2$Cl$_2$. The organic phases are washed with water (3×25 ml), dried over Na$_2$SO$_4$ and concentrated. FC(RP-C18-SiO$_2$ MeCN/CH$_2$Cl$_2$ 75:25) gives product 15 (0.37 g, 42%).

$^1$H NMR (CDCl$_3$, 400 MHz): δ=8.12 (d, 4H), 8.05 (2×s, 4H), 7.73 (d, 2H), 7.67 (d, 2H), 7.61 (d, 2H), 7.56 (d, 2H), 7.30 (m, 12H), 0.65 (s, 6H).

Synthesis Example 16

Synthesis of Compound 16

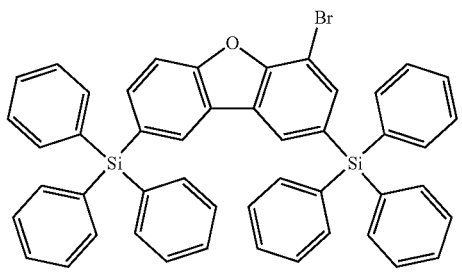

Step 1

Synthesis of 2,8-bis(triphenylsilyl)dibenzofuran

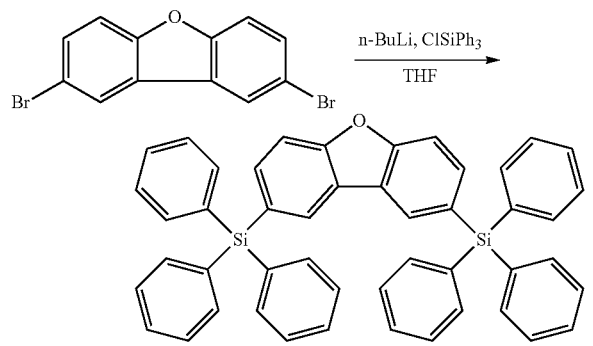

6.02 g (18.47 mmol) of 2,8-dibromodibenzofuran are suspended in 120 ml of THF and admixed cautiously at −78° C. with 22.9 ml (36.64 mmol) of n-BuLi (1.6 m in hexane). Thereafter, the mixture is stirred at −78° C. for 3 h. The reaction mixture is admixed with a solution of 10.91 g (37.00 mmol) of chlorotriphenylsilane in 120 ml of THF, allowed to warm up to room temperature and stirred at room temperature for 16 h. The mixture is quenched cautiously with 10 ml of methanol and then concentrated to dryness. The residue is digested first in methanol, then in water and then again in methanol, filtered off and dried. The crude product is dissolved in methylene chloride, filtered through silica gel and crystallized by blanketing with cyclohexane. The crystals are filtered off and dried. This affords 9.28 g (73%) of white powder.

$^1$H NMR: (CD$_2$Cl$_2$, 500 MHz):

δ=7.35-7.38 (m, 12H, CH$_{Ar}$), 7.41-7.44 (m, 6H, CH$_{Ar}$), 7.56-7.57 (m, 12H, CH$_{Ar}$), 7.58-7.63 (m, 4H, CH$_{Ar}$), 8.09 (s, 2H, CH$_{Ar}$).

Mass (EI): m/e=684 (M$^+$)

Step 2

A solution of 2,8-bis(triphenylsilyl)dibenzofuran (10.0 g, 14.6 mmol) in dry THF (200 ml) is admixed, at −78° C. under argon, gradually with n-butyllithium (1.6 m in hexane, 11.0 ml, 17.5 mmol), and stirred at 0° C. for 2 h. After a solution of 1,2-dibromethane (3.88 g, 20.4 mmol) in dry THF (8 ml) has been added slowly at −78° C., the mixture is warmed to room temperature with stirring overnight. The solution is admixed with MeOH (20 ml) and stirred for 30 min. Methylene chloride is added until a solution forms. The organic phase is washed with water (3×100 ml), dried over Na$_2$SO$_4$ and concentrated. Yield 11.2 g. The mixture of ~25% reactant and ~75% product is used in the next step (example 17).

Synthesis Example 17

Synthesis of Compound 17

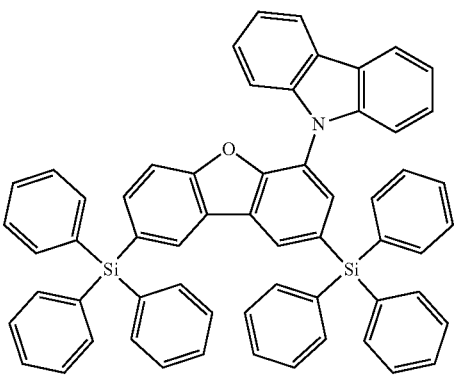

Product 16 (see example 16, 11.0 g), carbazole (95%, 2.53 g, 14.4 mmol), potassium carbonate (4.98 g, 36.0 mmol) and copper powder (183 mg, 2.88 mmol) in tridecane (50 ml) are heated to 195° C. and stirred at this temperature for 96 h. After cooling to room temperature, the mixture is extracted with methylene chloride. Tridecane is distilled off. FC (SiO$_2$, 85:15 cyclohexane/CH$_2$Cl$_2$) gives the product 17 (6.3 g, 51%) (over two steps).

$^1$H NMR (CDCl$_3$, 400 MHz): δ=7.28 (dd, 2H), 7.33-7.48 (m, 22H), 7.57-7.66 (m, 14H), 7.83 (s, 1H), 8.15 (m, 4H).

Synthesis Example 18

Synthesis of Compound 18

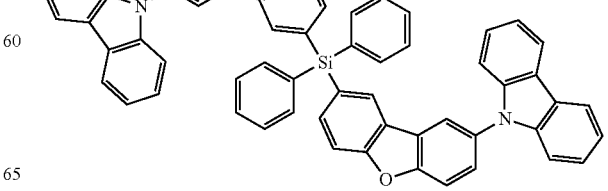

A solution of 13 (1.0 g, 2.4 mmol) and dichlorodiphenylsilane (0.32 g, 1.2 mmol) in dry diethyl ether (10 ml) is admixed under argon gradually with tert-butyllithium (1.7 m in pentane, 2.9 ml, 4.9 mmol), and stirred overnight. The mixture is admixed with MeOH (5 ml) and diluted further with $CH_2Cl_2$. The organic phases are washed with water (3×25 ml), washed with $Na_2SO_4$, dried and concentrated. FC(RP-C18-$SiO_2$ MeCN/$CH_2Cl_2$ 2:3) gives product 18 (0.50 g, 49%).

$^1$H NMR (CDCl$_3$, 400 MHz): δ=8.12 (s, 2H), 8.10 (m, 4H), 7.96 (s, 2H), 7.74 (d, 4H), 7.65 (d, 2H), 7.60 (d, 4H), 7.56 (d, 2H), 7.36 (m, 10H), 7.26 (m, 8H).

Synthesis Example 19

Synthesis of Compound 19

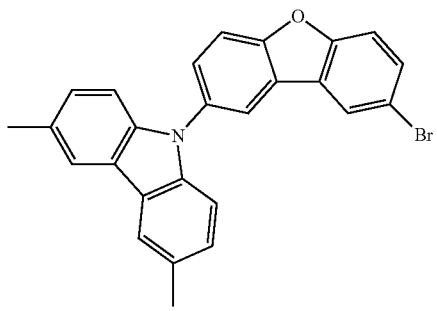

2,8-Dibromobenzofuran (18.8 g, 57.7 mmol), 3,6-dimethylcarbazole (12.4 g, 63.4 mmol), potassium carbonate (21.9 g, 159 mmol) and copper powder (732 mg, 11.5 mmol) in tridecane (200 ml) are heated to 185° C. and stirred at this temperature for 240 h. Cooling to room temperature is followed by extraction with methylene chloride. Tridecane is distilled off. Recrystallization from cyclohexane and FC (SiO$_2$, cyclohexane/$CH_2Cl_2$, 100:0 to 9:1) gives the product 19 (8.6 g, 33%).

$^1$H NMR (CDCl$_3$, 400 MHz): (δ=2.55 (s, 6H), 7.18-7.28 (m, 6H), 7.51 (d, 1H), 7.59-7.65 (2× d, 2H), 7.75 (d, 1H), 7.92 (2×s, 2H), 8.05 (d, 2H).

Synthesis Example 20

Synthesis of Compound 20

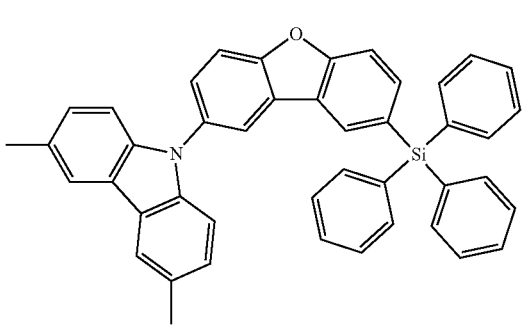

A solution of 19 (2.8 g, 6.4 mmol) and triphenylchlorosilane (2.0 g, 6.4 mmol) in dry diethyl ether (20 ml) is admixed slowly under argon with n-butyllithium (1.6 M in hexane, 5.2 ml, 8.3 mmol) and stirred overnight. The mixture is admixed with MeOH (10 ml) and diluted further with $CH_2Cl_2$. The organic phases are washed with water (3×50 ml), dried with $Na_2SO_4$ and concentrated. Recrystallization (2×) gives product 20 (2.25 g, 57%).

$^1$H NMR (CDCl$_3$, 400 MHz): δ=2.50 (s, 6H), 7.20 (m, 4H), 7.40 (m, 9H), 7.58 (m, 7H), 7.65 (d, 1H), 7.74 (dd, 2H), 7.90 (s, 2H), 7.98 (s, 1H), 8.10 (s, 1H).

Synthesis Example 21

Synthesis of Compound 21

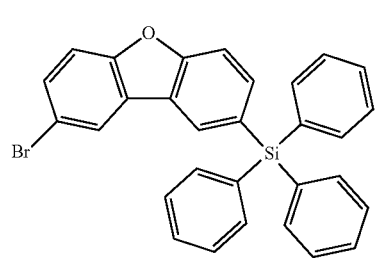

A cold solution (−15° C.) of 2,8-dibromodibenzofuran (20.0 g, 61.3 mmol) in dry diethyl ether (200 ml) is admixed slowly under argon with n-butyllithium (1.6 M in hexane, 40.3 ml, 64.4 mmol) and stirred at −15° C. for 2 h, after which a solution of triphenylchlorosilane (18.6 g, 61.3 mmol) in dry diethyl ether (100 ml) is added dropwise. The mixture is stirred to RT overnight and is then admixed with MeOH (25 ml) and diluted further with $CH_2Cl_2$. The organic phases are washed with water (3×100 ml), dried with $Na_2SO_4$ and concentrated. FC (SiO$_2$, cyclohexane/$CH_2Cl_2$, 100:0 to 9:1) gives product 21 (9.3 g, 30%).

$^1$H NMR (CD$_2$Cl$_2$, 400 MHz): δ=7.38-7.50 (m, 10H), 7.56 (d, 1H), 7.60 (m, 7H), 7.68 (d, 1H), 8.01 (s, 1H), 8.12 (s, 1H).

Synthesis Example 22

Synthesis of Compound 22

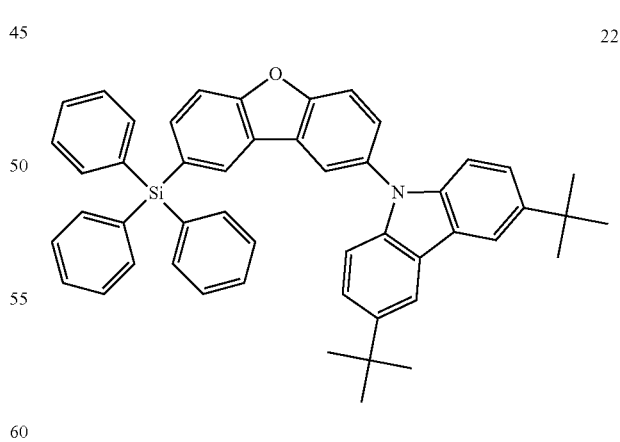

The synthesis of 3,6-bis(tert-butyl)carbazole is described in Chemistry Letters, 37(9), 986-987; 2008.

Compound 21 (5.13 g, 10.1 mmol), 3,6-bis(tert-butyl)carbazole (2.91 g, 10.4 mmol), potassium carbonate (3.59 g, 26.0 mmol) and copper powder (133 mg, 2.1 mmol) in tridecane (20 ml) are heated to 185° C. and stirred at this temperature for 60 h. Cooling to room temperature is followed by extraction with methylene chloride. The solution is concentrated and the residue is suspended in heptane (2×60 ml), stirred and filtered off. Product 22 (4.69 g, 66%).

$^1$H NMR (CDCl$_3$, 400 MHz): δ=1.48 (s, 18H), 7.27 (d, 2H), 7.40 (m, 11H), 7.58 (m, 7H), 7.70 (dd, 2H), 7.78 (d, 1H), 8.02 (s, 1H), 8.18 (2×s, 3H).

Synthesis Example 23

Synthesis of Compound 23

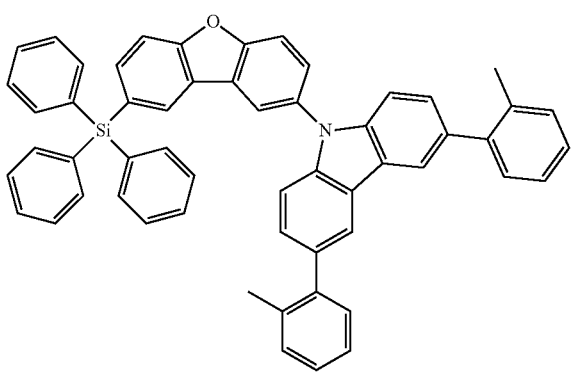

23

3,6-Bis(2-Tolyl)carbazole can be prepared by the process described in US 2005/0084711 A1.

Compound 21 (4.30 g, 8.50 mmol), 3,6-bis(2-tolyl)carbazole (2.95 g, 8.5 mmol), potassium carbonate (2.94 g, 21.2 mmol) and copper powder (108 mg, 1.70 mmol) in tridecane (25 ml) are heated to 185° C. and stirred at this temperature for 96 h. Cooling to room temperature is followed by extraction with methylene chloride. The solution is concentrated and the residue is suspended in heptane (25 ml), stirred and filtered off. FC (SiO$_2$, cyclohexane/CH$_2$Cl$_2$, 100:0 to 9:1) gives product 23 (3.14 g, 48%).

$^1$H NMR (CD$_2$Cl$_2$, 400 MHz): δ=2.35 (s, 6H), 7.23-7.47 (m, 21H), 7.60 (d, 6H), 7.72 (m, 3H), 7.85 (d, 1H), 8.08 (s, 2H), 8.13 (s, 1H) 8.22 (s, 1H).

Synthesis Example 24

Synthesis of Compound 24

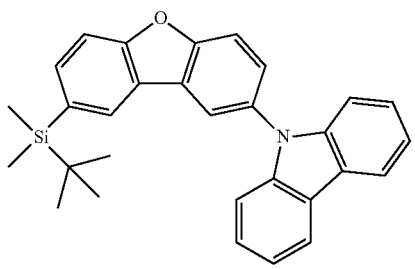

24

A solution of 13 (0.50 g, 0.12 mmol) and tert-butyldimethylchlorosilane (0.28 g, 0.18 mmol) in dry diethyl ether (9 ml) is admixed slowly under argon with n-butyllithium (1.6 M in hexane, 0.8 ml, 0.13 mmol) and stirred overnight. The mixture is admixed with sat. NH$_4$Cl solution (10 ml) and extracted with CH$_2$Cl$_2$. The organic phases are dried with Na$_2$SO$_4$ and concentrated. FC(C18-SiO$_2$, MeCN) gives product 24 (0.15 g, 27%). The yield is low owing to the small batch size.

$^1$H NMR (CD$_2$Cl$_2$, 400 MHz): δ=0.36 (s, 6H), 0.90 (s, 9H), 7.30 (dd, 2H), 7.42 (dd, 4H), 7.66 (m, 3H), 7.80 (d, 1H), 8.13 (s, 1H), 8.18 (s, 1H), 8.19 (d, 2H).

Synthesis Example 25

Synthesis of Compound 25

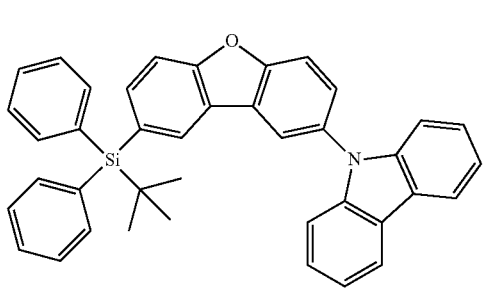

25

A solution of 13 (0.50 g, 0.12 mmol) and tert-butyldiphenylchlorosilane (0.50 g, 0.18 mmol) in dry diethyl ether (9 ml) is admixed slowly under argon with n-butyllithium (1.6 M in hexane, 1.14 ml, 0.18 mmol) and stirred overnight. The mixture is admixed with sat. NH$_4$Cl solution (10 ml) and extracted with CH$_2$Cl$_2$. The organic phases are dried with Na$_2$SO$_4$ and concentrated. FC(C18-SiO$_2$, MeCN) gives product 25 (0.12 g, 17%). The yield is low owing to the small batch size.

$^1$H NMR (CD$_2$Cl$_2$, 400 MHz): δ=1.21 (s, 9H), 7.28 (dd, 2H), 7.37 (m, 10H), 7.60 (m, 5H), 7.64 (d, 1H), 7.74 (d, 1H), 7.81 (d, 1H), 8.04 (s, 1H), 8.15 (s, 1H), 8.18 (d, 2H).

Synthesis Example 26

Synthesis of Compound 26

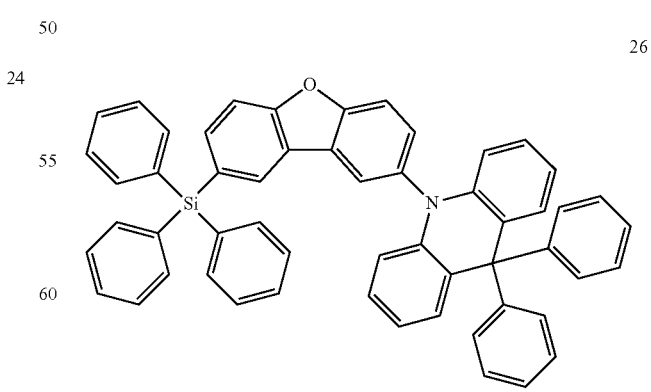

26

The synthesis of 9,9-dimethyl-9,10-dihydroacridine is described in Chemische Berichte; 37; 1904; 3202.

Compound 21 (6.07 g, 12.0 mmol), 9,9-dimethyl-9,10-dihydroacridine (4.00 g, 12.0 mmol), potassium carbonate (4.15 g, 30.0 mmol) and copper powder (152 mg, 2.4 mmol) in tridecane (30 ml) are heated to 220° C. and stirred at this temperature for 48 h. Cooling to room temperature is followed by extraction with methylene chloride. The solution is concentrated and the residue is suspended in a little heptane, stirred and filtered off, and subsequently suspended in methylene chloride, stirred and filtered off, and, after being suspended in methylene chloride, stirred and filtered off, gives the product 26 (2.13 g, 23%).

$^1$H NMR (CD$_2$Cl$_2$, 400 MHz): δ=6.42 (d, 2H), 6.87 (dd, 4H), 7.00 (m, 6H), 7.18-7.28 (m, 7H), 7.40 (t, 6H), 7.45 (m, 4H), 7.60 (d, 6H), 7.65 (d, 1H), 7.69 (d, 1H), 7.73 (d, 1H), 8.03 (s, 1H).

Synthesis Example 27

Synthesis of Compound 27

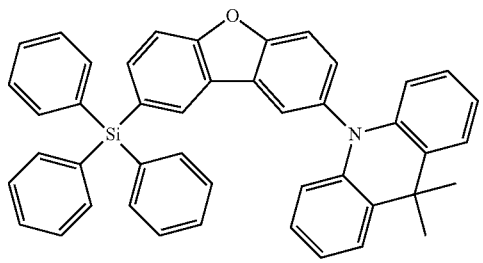

27

The synthesis of 9,9-dimethyl-9,10-dihydroacridine is described in Chemische Berichte, 113(1), 358-84; 1980.

Compound 21 (3.99 g, 7.89 mmol), 9,9-dimethyl-9,10-dihydroacridine (1.82 g, 8.68 mmol), potassium carbonate (3.00 g, 21.7 mmol) and copper power (100 mg, 1.58 mmol) in tridecane (40 ml) are heated to 225° C. and stirred at this temperature for 92 h. Cooling to room temperature is followed by extraction with methylene chloride. The solution is concentrated and FC (SiO$_2$, cyclohexane/CH$_2$Cl$_2$, 9:1 to 1:1) gives product 27 (0.85 g, 17%).

$^1$H NMR (CD$_2$Cl$_2$, 400 MHz): g=1.68 (s, 6H), 6.24 (d, 2H), 6.89 (dd 4H), 7.36-7.48 (m, 12H), 7.58 (d, 6H), 7.70 (dd, 2H), 7.83 (d+s, 2H), 8.13 (s, 1H).

Synthesis Example 28

Synthesis of Compound 28

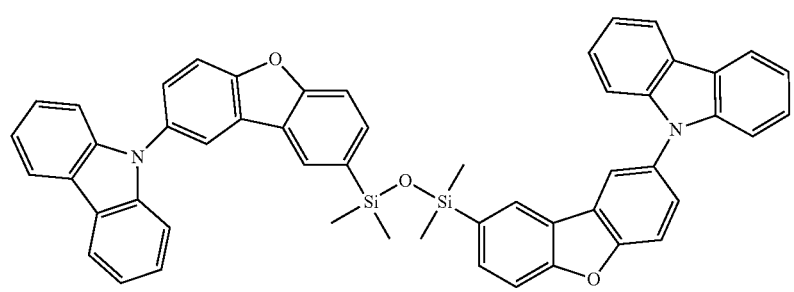

28

A mixture of 13 (5.15 g, 12.5 mmol) and 1,3-dichloro-1,1,3,3-tetramethyldisiloxane (1.31 g, 6.25 mmol) in dry diethyl ether (150 ml) is admixed slowly under argon with t-butyllithium (1.7 M in pentane, 14.7 ml, 25 mmol) and stirred overnight. The mixture is admixed with sat. NR$_4$Cl solution (30 ml) and extracted with CH$_2$Cl$_2$. The organic phases are dried with Na$_2$SO$_4$ and concentrated. FC (SiO$_2$, cyclohexane/CH$_2$Cl$_2$, 9:1 to 1:9) gives product 28 (2.90 g, 58%).

$^1$H NMR (CD$_2$Cl$_2$, 400 MHz): δ=0.40 (s, 12H), 7.28 (dd, 4H), 7.37 (d, 4H), 7.42 (dd, 4H), 7.53 (d, 2H), 7.55 (d, 2H), 7.60 (d, 2H), 7.68 (d, 2H), 7.96 (s, 2H), 8.04 (s, 2H), 8.18 (d, 4H).

Synthesis Example 29

Synthesis of Compound 29

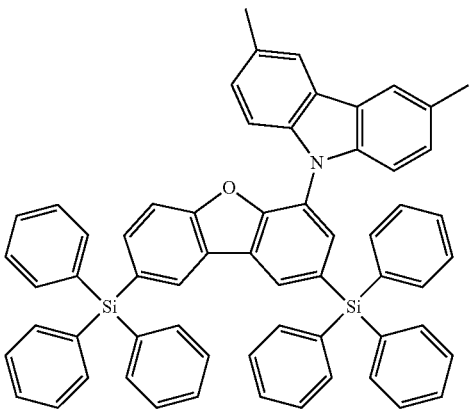

29

Product 16 (see Example 16, 10.0 g), 3,6-dimethylcarbazole (2.55 g, 13.1 mmol), potassium carbonate (4.61 g, 32.7 mmol) and copper powder (166 mg, 2.61 mmol) in tridecane (100 ml) are heated to 205° C. and stirred at this temperature for 72 h. Cooling to room temperature is followed by extraction with methylene chloride. Tridecane is distilled off. FC (SiO$_2$, cyclohexane/CH$_2$Cl$_2$ 9:1 to 1:1) gives the product 29 (3.1 g, 26% (over two steps)).

$^1$H NMR (CDCl$_3$, 400 MHz): δ=2.50 (s, 6H), 7.04 (d, 2H), 7.11 (d, 2H), 7.32-7.46 (m, 19H), 7.52-7.62 (m, 13H), 7.80 (s, 1H), 7.88 (s, 2H), 8.12 (s, 2H).

Synthesis Example 30

Synthesis of Compound 30

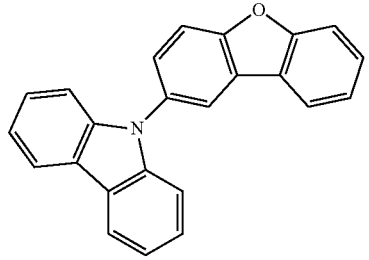

30

2-Bromodibenzofuran (24.7 g, 100 mmol), carbazole (95%, 26.4 g, 150 mmol), potassium carbonate (51.8 g, 375 mmol) and copper powder (1.27 g, 20 mmol) in tridecane (150 ml) are heated to 180° C. and stirred at this temperature for 72 h. Cooling to room temperature is followed by extraction with methylene chloride. The solution is concentrated and the residue is suspended in heptane (25 ml), stirred and filtered off. FC (SiO$_2$, cyclohexane/CH$_2$Cl$_2$ 5:1) gives product 30 (19.6 g, 59%).

$^1$H NMR (CD$_2$Cl$_2$, 400 MHz): δ=7.3 (dd, 2H), 7.4 (m, 5H), 7.5 (dd, 1H), 7.6 (dd, 2H), 7.8 (d, 1H), 8.0 (d, 1H), 8.2 (s+d, 1+2H).

Synthesis Example 31

Synthesis of Compound 31

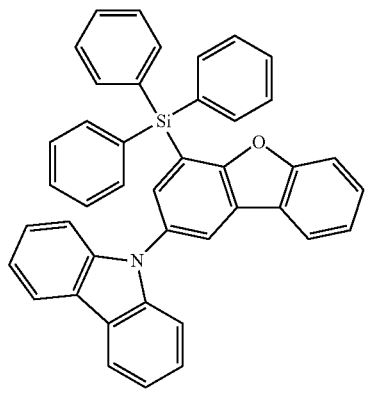

31

A solution of 30 (3.3 g, 10 mmol) in THF (130 ml) is admixed slowly at −78° C. under argon with n-butyllithium (1.6 M in hexane, 7.5 ml, 12 mmol) and stirred at 0° C. for two hours. The solution is cooled to −78° C. and a solution of triphenylchlorosilane (4.42 g, 15 mmol) in THF (10 ml) is added. The solution is stirred to RT overnight, admixed with NR$_4$Cl solution (30 ml) and extracted with CH$_2$Cl$_2$. The organic phases are dried with Na$_2$SO$_4$ and concentrated. FC(C18-SiO$_2$, MeCN) gives product 31 (2.35 g, 40%).

$^1$H NMR (CDCl$_3$, 400 MHz): δ=7.28 (d, 1H), 7.32-7.48 (m, 17H), 7.60 (s, 1H), 7.70 (d, 6H), 7.95 (d, 1H), 8.2 (d, 2H), 8.20 (s, 1H).

Synthesis Example 32

Synthesis of Compound 32

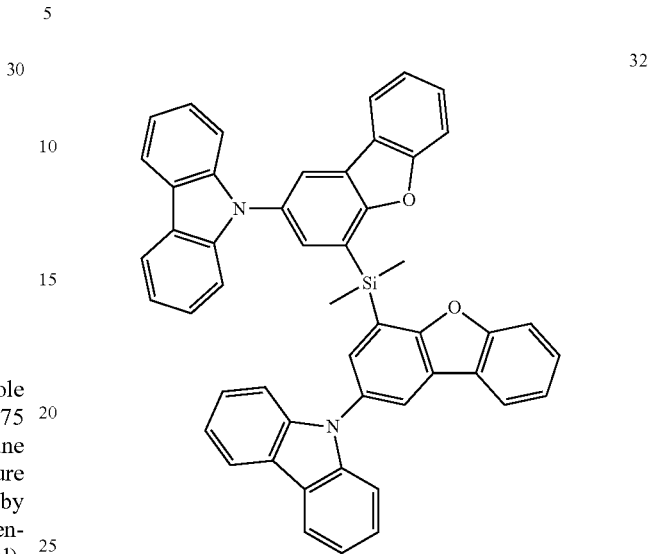

32

A solution of 30 (3.0 g, 9 mmol) in THF (80 ml) is admixed slowly at −40° C. under argon with n-butyllithium (1.6 M in hexane, 9.5 ml, 15 mmol) and stirred at 0° C. for two hours. The solution is cooled to −78° C. and a solution of dimethyldichlorosilane (0.59 g, 4.5 mmol) in THF (5 ml) is added. The solution is stirred to RT overnight, admixed with NH$_4$Cl solution (20 ml) and extracted with CH$_2$Cl$_2$. The organic phases are dried with Na$_2$SO$_4$ and concentrated. FC (SiO$_2$, cyclohexane:CH$_2$Cl$_2$ 9:1) gives product 32 (2.08 g, 64%).

$^1$H NMR (CD$_2$Cl$_2$, 400 MHz): δ=1.02 (s, 6H), 7.24 (m, 8H), 7.30 (d, 4H), 7.40 (dd, 2H), 7.55 (dd, 2H), 7.65 (d, 2H), 7.80 (s, 2H), 7.98 (d, 2H), 8.15 (d+s, 4+2H)

Synthesis Example 33

Synthesis of Compound 33

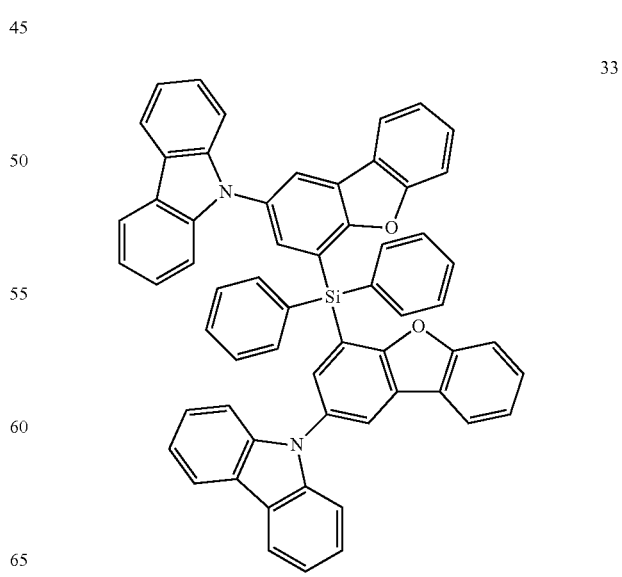

33

A solution of 30 (2.2 g, 6.7 mmol) in THF (60 ml) is admixed slowly at −40° C. under argon with n-butyllithium (1.6 M in hexane, 7.3 ml, 11.7 mmol) and stirred at 0° C. for two hours. The solution is cooled to −78° C. and a solution of diphenyldichlorosilane (0.86 g, 3.35 mmol) in THF (5 ml) is added. The solution is stirred to RT overnight, admixed with NH$_4$Cl solution (20 ml) and extracted with CH$_2$Cl$_2$. The organic phases are dried with Na$_2$SO$_4$ and concentrated. FC (SiO$_2$, cyclohexane: CH$_2$Cl$_2$ 9:1) gives product 33 (1.82 g, 64%).

$^1$H NMR (CD$_2$Cl$_2$, 400 MHz): δ=7.18 (m, 8H), 7.32 (d, 4H), 7.40 (m, 8H), 7.50 (m, 4H), 7.70 (s, 2H), 7.88 (d, 4H), 7.98 (d, 2H), 8.08 (d, 4H), 8.25 (s, 2H)

DIODE EXAMPLES

Comparative Example

Production of an OLED Comprising 9-phenyl-3,6-bis(triphenylsilyl)carbazole as Matrix Material (91.5% by Weight) and as Hole/Exciton Blocker The ITO substrate used as the anode is first cleaned with commercial detergents for LCD production (Deconex® 20NS, and 250RGAN-ACID® neutralizing agent) and then in an acetone/isopropanol mixture in an ultrasound bath. To eliminate any possible organic residues, the substrate is exposed to a continuous ozone flow in an ozone oven for a further 25 minutes. This treatment also improves the hole injection properties of the ITO.

Thereafter, the organic materials specified below are applied by vapor deposition to the cleaned substrate at a rate of approx. 0.5-5 nm/mn at about 10$^{-8}$ mbar. As a hole conductor and exciton blocker, Ir(dpbic)$_3$ (V1) is applied to the substrate with a thickness of 45 nm.

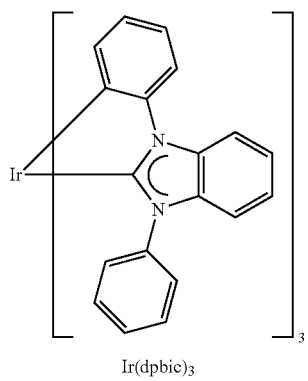

Ir(dpbic)$_3$ (for preparation, see Ir complex (7) in the application WO 2005/019373).

Subsequently, a mixture of 8.5% by weight of the compound (V2) and 91.5% by weight of the compound (V1) are applied by vapor deposition in a thickness of 10 nm, the former compound functioning as emitter material, the latter as matrix material.

Subsequently, a mixture of 8.5% by weight of compound (V2) and 91.5% by weight of the compound 9-phenyl-3,6-bis(triphenylsilyl)carbazole (V3) is applied by vapor deposition in a thickness of 40 nm, the former compound functioning as an emitter material, the latter as a matrix material.

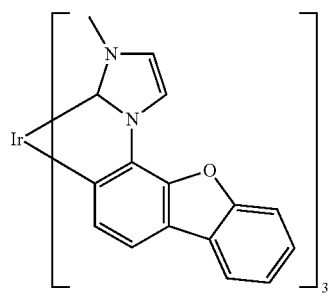

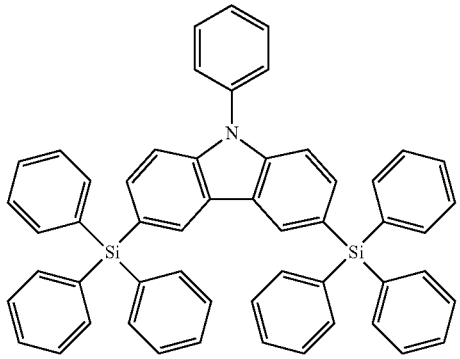

Subsequently, the material 9-phenyl-3,6-bis(triphenylsilyl)carbazole (V3) is applied by vapor deposition with a thickness of 10 nm as exciton and hole blocker.

Next, an electron conductor BCP is applied by vapor deposition in a thickness of 40 nm, as are a 0.75 nm-thick lithium fluoride layer and finally a 110 nm-thick Al electrode.

To characterize the OLED, electroluminescence spectra are recorded at various currents and voltages. In addition, the current-voltage characteristic is measured in combination with the light output emitted. The light output can be converted to photometric parameters by calibration with a photometer.

Diode Example 1

Production and construction of an OLED as in the comparative example, except compound 3 is used instead of 9-phenyl-3,6-bis(triphenylsilyl)carbazole (V3).

Table 1 shows a comparison of the electrical properties of the OLEDs from the comparative example and diode example 1. The use of compound 3 instead of compound V3 increases both the power efficiency and the quantum efficiency QE, and lowers the voltage.

In the first two columns of table 1, the materials of the matrix of an emission layer and of the hole blocker/exciton blocker layer and the structural formulae thereof are reported.

In the right-hand column of table 1, the structure of the particular OLED with the materials of the various layers, and the thicknesses thereof, are reported. The anode is a 125 nm±20 nm-thick ITO layer, on which are deposited

- a 45 nm-thick hole conductor/exciton blocker layer of material (V1),
- a first, 10 nm-thick emission layer with 8.5% by weight of (V2) as an emitter in a matrix material of (V1),
- a second, 40 nm-thick emission layer with 8.5% by weight of (V2) as an emitter and (V3) (comparative example) or 3 (diode example 1) as a matrix material,
- a 10 nm-thick hole blocker/exciton blocker layer composed of (V3) (comparative example) or 3 (diode example 1),
- a 40 nm-thick electron conductor layer of BCP, and
- a cathode of LiF/aluminum.

TABLE 1

| Material | Structure | Power efficiency at 300 cd/m2 | QE at 300 cd/m2 | Voltage at 300 cd/m2 [V] | Structure of the OLED on an anode (Thickness = 125 +/− 20 nm) (Production analogous to the comparative example) |
|---|---|---|---|---|---|
| V3 | (structure) | 100 | 100 | 100 | V1 (45 nm)//8.5% V2:V1 (10 nm)//8.5% V2:V3 (40 nm)//V3 (10 nm)//BCP (40 nm)//LiF//Alu |
| 3 | (structure) | 157 | 156 | 81 | V1 (45 nm)//8.5% V2:V1 (10 nm)//8.5% V2:3 (40 nm)//3 (10 nm)//BCP (40 nm)//LiF//Alu |
| 14 | (structure) | 142 | 162 | 58 | PEDOT-PSS//V1:MoO3 (10%) (35 nm)//V1 (10 nm)// 10% V2:V1 (10 nm)//10% V2:14 (30 nm)//V4 (5 nm)// BCP (30 nm)//LiF//Alu |

The power efficiency, quantum efficiency and voltage are each relative values based on the OLED comprising material V3.

PEDOT-PSS is used as the hole injection layer (see diode example 16)

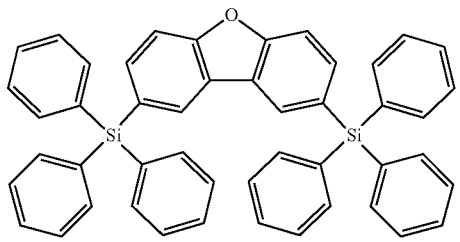

V4

Diode Example 2

As in the comparative example, except compound 12 is used instead of 9-phenyl-3,6-bis(triphenylsilyl)carbazole V3.

Diode Example 3

According to diode example 1, except that, instead of the light blue-emitting emitter material (V2), a green-emitting emitter material is used, which is selected from tris(2-phenylpyridine)iridium(III), tris(2-(p-tolyl)pyridine)iridium (III) and bis(2-phenyl-pyridine)(acetylacetonate)iridium (III).

Diode Example 4

According to diode example 1, except that, instead of the light blue-emitting emitter material (V2), a red-emitting emitter material is used, which is selected from: iridium(III) tris(1-phenylisoquinoline), tris(2-phenylquinoline)iridium (III), iridium(III) bis(2,2'-benzothienyl)pyridinato-N,C$^{3'}$) (acetylacetonate), iridium(III) bis(1-phenylisoquinoline) (acetylacetonate), bis(2-phenylquinoline)(acetylacetonato) iridium (III), iridium(III) bis(dibenzo[f,h]quinoxaline) (acetylacetonate), iridium(III) bis(2-methyldibenzo[f,h] quinoxaline)(acetylacetonate), bis[1-(9,9-dimethyl-9H-fluoren-2-yl)isoquinoline](acetylacetonate)iridium(III), bis (2-benzo[b]-thiophen-2-ylpyridine)(acetylacetonato)iridium (III), bis(2-phenylbenzothiazolato)-(acetylacetonato)-iridium(III), bis(2-(9,9-dihexylfluorenyl)-1-pyridine) (acetylacetonato)-indium(III), bis[3-(9,9-dimethyl-9H-fluoren-2-yl)isoquinoline](acetylacetonato)-iridium(III), tris (dibenzoylacetonato)mono(phenanthroline)europium(III), osmium(II) bis(3-(trifluoromethyl)-5-(4-tert-butylpyridyl)-1,2,4-triazolato)diphenylmethylphosphine, osmium(II) bis (3-(trifluoromethyl)-5-(2-pyridyl)-1,2,4-triazole)dimethyl-phenylphosphine, osmium(II) bis(3-(trifluoromethyl)-5-(4-tert-butylpyridyl)-1,2,4-triazolato) dimethylphenylphosphine, osmium(II) bis(3-(trifluoromethyl)-5-(2-pyridyl)pyrazolato) dimethylphenylphosphine, tris[4,4'-di-tert-butyl(2,2')-bipyridine]ruthenium(III), osmium(II) bis(2-(9,9-dibutylfluorenyl)-1-isoquinoline(acetylacetonate).

Diode Example 5

According to diode example 1, except that, instead of the material for the hole conductor/exciton blocker layer (V1), a material is used, which is selected from: 4,4',4"-tris(N,N-diphenylamino)triphenylamine (TDTA), N,N'-bis(naphthalen-2-yl)-N,N'-bis(phenyl)benzidine (6-NPB), N,N'-bis(3-methylphenyl)-N,N'-bis(phenyl)-9,9-spirobifluorene (Spiro-TPD), N,N'-bis(naphthalen-1-yl)-N,N'-bis(phenyl)-9,9-spirobifluorene (Spiro-NPB), N,N'-bis(3-methylphenyl)-N, N'-bis(phenyl)-9,9-dimethylfluorene (DMFL-TPD), N,N'-bis(naphthalen-1-yl)-N,N'-bis(phenyl)-9,9-dimethylfluorene, N,N'-bis(naphthalen-1-yl)-N,N'-bis(phenyl)-2,2-dimethylbenzidine, N,N'-bis(naphthalen-1-yl)-N,N'-bis(phenyl)benzidine, N,N'-bis(3-methylphenyl)-N,N'-bis(phenyl)benzidine, 2,3,5,6-tetrafluoro-7,7,8,8-tetracyanoquinodimethane (F4-TCNQ), 4,4',4"-tris(N-3-methylphenyl-N-phenylamino)triphenylamine, 4,4',4"-tris (N-(2-naphthyl)-N-phenylamino)triphenylamine, pyrazino [2,3-f][1,10]phenanthroline-2,3-dicarbonitrile (PPDN), N,N,N',N'-tetrakis(4-methoxyphenyl)benzidine (MeO-TPD), 2,7-bis[N,N-bis(4-methoxyphenyl)amino]-9,9-spiro-bifluorene (MeO-Spiro-TPD), 2,2'-bis[N,N-bis(4-methoxy-phenyl)amino]-9,9-spirobifluorene (2,2'-MeO-Spiro-TPD), N,N'-diphenyl-N,N'-di[4-(N,N-ditolylamino)phenyl]benzi-dine (NTNPB), N,N'-diphenyl-N,N'-di[4-(N,N-diphe-nylamino)phenyl]benzidine (NPNPB), N,N'-di(naphthalen-2-yl)-N,N'-diphenylbenzene-1,4-diamine (6-NPP), N,N'-bis (3-methylphenyl)-N,N'-bis(phenyl)-9,9-diphenylfluorene (DPFL-TPD), N,N'-bis(naphthalen-1-yl)-N,N'-bis(phenyl)-9,9-diphenylfluorene (DPFL-NPB), 2,2',7,7'-tetrakis(N,N-diphenylamino)-9,9'-spirobifluorene (Spiro-TAD), 9,9-bis [4-N,N-bis(biphenyl-4-yl)amino)phenyl]-9H-fluorene (BPAPF), 9,9-bis[4-(N,N-bis(naphthalen-2-yl)amino)phe-nyl]-9H-fluorene (NPAPF), 9,9-bis[4-(N,N-bis(naphthalen-2-yl)-N,N'-bisphenylamino)phenyl]-9H-fluorene (NPBAPF), 2,2',7,7'-tetrakis[N-naphthalenyl(phenyl) amino]-9,9'-spirobifluorene (Spiro-2NPB), N,N'-bis (phenanthren-9-yl)-N,N'-bis(phenyl)benzidine (PAPB), 2,7-bis[N,N-bis(9,9-spirobifluoren-2-yl)amino]-9,9-spirobifluorene (Spiro-5), 2,2'-bis[N,N-bis(biphenyl-4-yl) amino]-9,9-spirobifluorene (2,2'-Spiro-DBP), 2,2'-bis(N,N-diphenylamino)-9,9-spirobifluorene (Spiro-BPA), 2,2',7,7'-tetra(N,N-ditolyl)aminospirobifluorene (Spiro-TTB), N,N, N',N'-tetranaphthalen-2-ylbenzidine (TNB), di[4-(N,N-ditolylamino)phenyl]cyclohexane, copper phthalocyanines and titanium oxide phthalocyanines.

Diode Example 6

According to diode examples 1 and 3 to 5, except that the hole blocker/exciton blocker material and/or electron conductor material used, instead of the compounds (V3) or 3 and BCP, is a material selected from:

2,9-dimethyl-4,7-diphenyl-1,10-phenanthroline (bathocuproin, (BCP)), bis(2-methyl-8-quinolinato)-4-phenylphenylato)aluminum(III) (BAlq), 2,2',2"-(1,3,5-benzenetriyl)-tris(1-phenyl-1-H-benzimidazole), 2-(4-biphenylyl)-5-(4-tert-butylphenyl)-1,3,4-oxadiazole, 8-hydroxyquinolinolatolithium, 4-(naphthalen-1-yl)-3,5-di-phenyl-4H-1,2,4-triazole, 1,3-bis[2-(2,2'-bipyridin-6-yl)-1, 3,4-oxadiazo-5-yl]benzene, 4,7-diphenyl-1,10-phenanthro-line, 3-(4-biphenylyl)-4-phenyl-5-tert-butylphenyl-1,2,4-triazole, 6,6'-bis[5-(biphenyl-4-yl)-1,3,4-oxadiazo-2-yl]-2, 2'-bipyridyl, 2-phenyl-9,10-di(naphthalene-2-yl)-anthracene, 2,7-bis[2-(2,2'-bipyridin-6-yl)-1,3,4-oxadiazo-5-yl]-9,9-dimethylfluorene, 1,3-bis[2-(4-tert-butylphenyl)-1,3,4-oxadiazo-5-yl]benzene, 2-(naphthalene-2-yl)-4,7-diphenyl-1,10-phenanthroline, tris(2,4,6-trimethyl-3-(pyridin-3-yl)phenyl)borane, 2,9-bis(naphthalene-2-yl)-4,7- diphenyl-1,10-phenanthroline, 1-methyl-2-(4-(naphthalene-2-yl)phenyl)-1H-imidazo[4,5-f][1, 10]phenanthroline.

Diode Example 7

According to diode example 1 with a first additional emission layer which emits red light and a second additional emission layer which emits green light. The first and second additional emission layers are arranged between the anode and the cathode together with the emission layers which emit light blue light and which comprise materials (V2) as emitters and 3 and (V1) as matrix material, and comprise, in addition to the emitter materials, in each case matrix materials such as charge carrier transport materials and/or charge carrier blocker materials. This OLED has an emission which is composed of the emission of all emission layers and comprises white light.

Diode Example 8

Use of OLEDs according to one of examples 1, 3, 4, 5, 6 in each case for a component which emits white light. For this purpose, a plurality of monochrome OLEDs which emit light of different colors are stacked one on top of another and connected to one another by means of "Charge generation layers" (CGLs). The CGLs may transport the charge carriers of an OLED to the OLED arranged above or below. The compound 3 is used in the OLEDs as matrix material and/or as hole blocker/exciton blocker material.

Diode Example 9

Use of OLEDs according to one of examples 1, 3, 4, 5 or 6 in each case for a component which emits white light. For this purpose, a plurality of monochrome OLEDs which emit light of different colors are arranged alongside one another in order to achieve a white light-emitting component. Appropriate control also allows a color-adjustable component to be obtained.

Diode Example 10

According to diode example 7, except that only one emission layer is present, which comprises a red emitter, a blue emitter and a green emitter, and the compound 3 as a matrix material. This affords a white light-emitting OLED which has all emitters in one layer.

Diode Example 11

As diode examples 1 to 10, except that a material selected from Cu, Au, Pt, Ph, Os, Al, Mg, Ca, Ba, Ag, Yb, Fe, Co, Ni, Au, ITO, AZO is selected for the first and/or second electrode.

Diode Example 12

As in the comparative example, except that compound 10 is used instead of 9-phenyl-3,6-bis(triphenylsilyl)carbazole V3.

Diode Example 13

As in the comparative example, except that compound 17 is used instead of 9-phenyl-3,6-bis(triphenylsilyl)carbazole V3.

Diode Example 14

The ITO substrate used as the anode is first cleaned with commercial detergents for LCD production (Deconex® 20NS, and 250RGAN-ACID® neutralizing agent) and then in an acetone/isopropanol mixture in an ultrasound bath. To eliminate any possible organic residues, the substrate is exposed to a continuous ozone flow in an ozone oven for a further 25 minutes. This treatment also improves the hole injection properties of the ITO. Next, the hole injection layer AJ20-1000 from Plexcore is applied by spin-coating from solution (~40 nm).

Thereafter, the organic materials specified below are applied by vapor deposition to the cleaned substrate at a rate of approx. 0.5-5 nm/min at about $10^{-8}$ mbar. As a hole conductor and exciton blocker, Ir(dpbic)$_3$ (V1) is applied to the substrate with a thickness of 45 nm, the first 35 nm of which are doped with $MoO_x$ (~50%) to improve the conductivity.

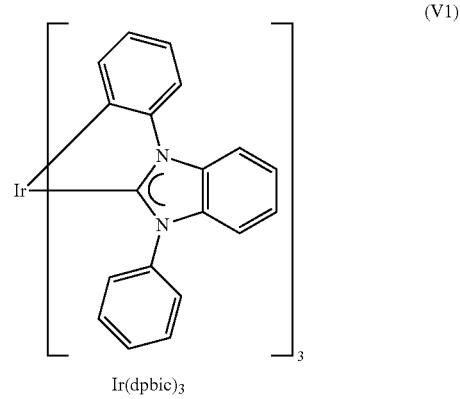

Ir(dpbic)$_3$ (V1)

(For preparation, see Ir complex (7) in the application WO 2005/019373).

Subsequently, a mixture of 15% by weight of the compound (V5)

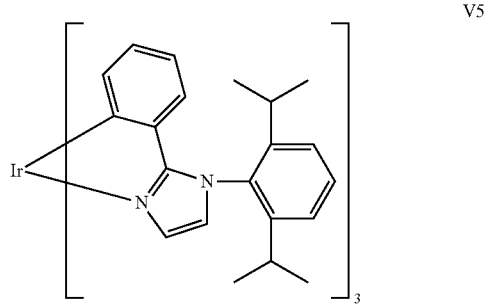

V5 and 85% by weight of the compound 28 are applied by vapor deposition in a thickness of 40 nm, the former compound functioning as emitter material, the latter as matrix material.

Subsequently, the material 14 is applied by vapor deposition with a thickness of 5 nm as exciton and hole blocker.

Next, as electron transporter a mixture of Liq and BCP (2,9-dimethyl-4,7-diphenyl-1,10-phenanthroline) is applied by vapor deposition in a thickness of 40 nm, as are a 1.0 nm-thick Liq layer and finally a 100 nm-thick Al electrode. All components are adhesive bonded to a glass lid in an inert nitrogen atmosphere.

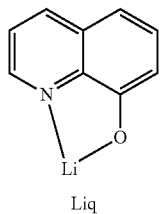

Liq

To characterize the OLED, electroluminescence spectra are recorded at various currents and voltages. In addition, the current-voltage characteristic is measured in combination with the light output emitted. The light output can be converted to photometric parameters by calibration with a photometer.

| CIE | Power efficiency at 300 cd/m$^2$ Cd/A | QE at 300 cd/m$^2$ (%) | Voltage at 300 cd/m$^2$ [V] |
|---|---|---|---|
| 0.19; 0.35 | 33.3 | 15.4 | 4.0 |

Diode Example 15

As in example 14, except that the matrix material used is compound 26 instead of compound 28, and the exciton and hole blocker used is compound 26 instead of 14. The dopant concentration of V5 is 20% instead of 15%.

| CIE | Power efficiency at 300 cd/m$^2$ Cd/A | QE at 300 cd/m$^2$ (%) | Voltage at 300 cd/m$^2$ [V] |
|---|---|---|---|
| 0.20; 0.35 | 33 | 15 | 5.9 |

Diode Example 16

The ITO substrate used as the anode is first cleaned with commercial detergents for LCD production (Deconex® 20NS, and 250RGAN-ACID® neutralizing agent) and then in an acetone/isopropanol mixture in an ultrasound bath. To eliminate any possible organic residues, the substrate is exposed to a continuous ozone flow in an ozone oven for a further 25 minutes. This treatment also improves the hole injection properties of the ITO. Next, the hole injection layer PEDOT-PSS(H. C. Starck, ~40 nm) is applied by spin-coating.

Thereafter, the organic materials specified below are applied by vapor deposition to the cleaned substrate at a rate of approx. 0.5-5 nm/min at about $10^{-8}$ mbar. As a hole conductor and exciton blocker, Ir(dpbic)$_3$ (V1) is applied to the substrate with a thickness of 55 nm, the first 35 nm of which are doped with MoO$_x$ (~50%) to improve the conductivity.

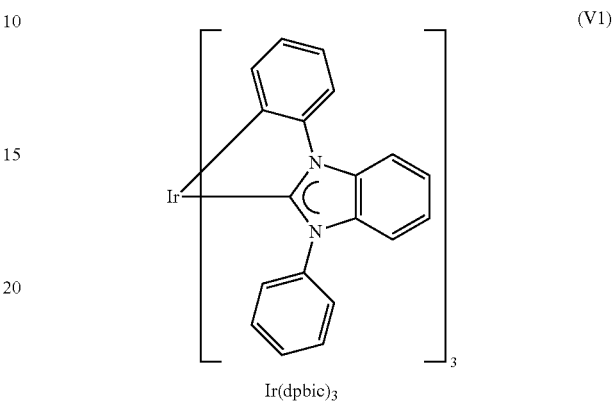

Ir(dpbic)$_3$ (For preparation, see Ir complex (7) in the application WO 2005/019373).

Subsequently, a mixture of 15% by weight of the compound (V5)

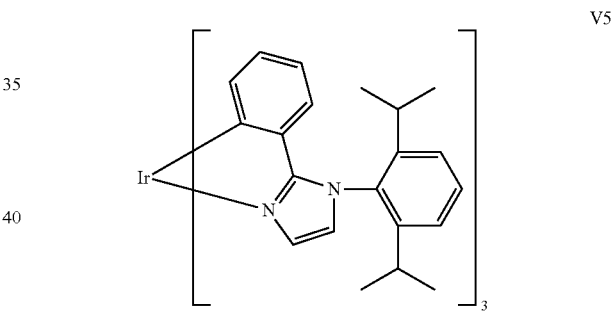

and 85% by weight of the compound 28 are applied by vapor deposition in a thickness of 30 nm, the former compound functioning as emitter material, the latter as matrix material.

Subsequently, the material V6 is applied by vapor deposition with a thickness of 5 nm as exciton and hole blocker.

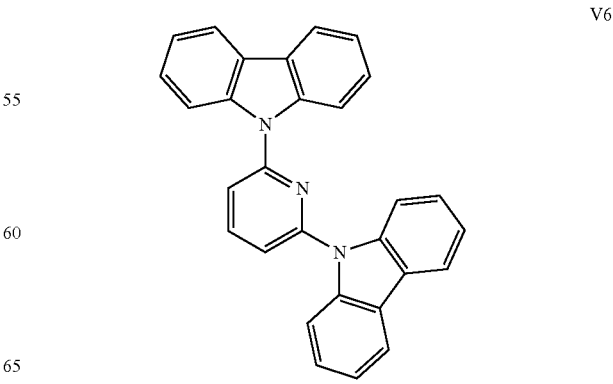

Next, as an electron transporter, tris(8-quinolinolato)aluminum (Alq$_3$) is applied by vapor deposition with a thickness of 50 nm, as are a 1.0 nm-thick LiF layer and finally a 100 nm-thick Al electrode. All components are adhesive bonded to a glass lid in an inert nitrogen atmosphere.

To characterize the OLED, electroluminescence spectra are recorded at various currents and voltages. In addition, the current-voltage characteristic is measured in combination with the light output emitted. The light output can be converted to photometric parameters by calibration with a photometer.

| CIE | Power efficiency at 300 cd/m$^2$ (Cd/A) | QE at 300 cd/m$^2$ (%) | Voltage at 300 cd/m$^2$ [V] |
|---|---|---|---|
| 0.19; 0.37 | 24.7 | 11.3 | 5.7 |

The invention claimed is:

1. A compound of formula (Ia), (Ib), (Ic), (Id), or (Ie)

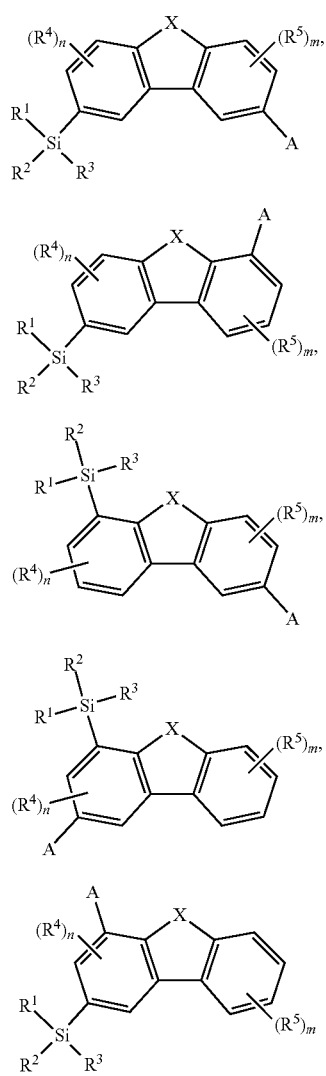

wherein

X is NR, S, or O;

R is aryl;

A is —NR$^6$R$^7$ or —P(O)R$^8$R$^9$;

R$^1$, R$^2$, and R$^3$ are each independently aryl, alkyl, or a crosslinkable or polymerizable group attached via a spacer, where at least one of the R$^1$, R$^2$, and R$^3$ radicals comprises at least two carbon atoms, or OR$^{22}$;

R$^4$ and R$^5$ are each independently alkyl, aryl, or a crosslinkable or polymerizable group attached via a spacer, an A group, or a group with donor or acceptor action;

n and m are each independently 0, 1, 2, or 3;

R$^6$ and R$^7$ together with the nitrogen atom form a cyclic radical which has 3 to 10 ring atoms and is optionally unsubstituted or substituted by one or more substituents selected from the group consisting of alkyl, cycloalkyl, heterocycloalkyl, aryl, heteroaryl, and a group with donor or acceptor action, and/or optionally fused to one or more further cyclic radicals having 3 to 10 ring atoms, where the fused radicals are optionally unsubstituted or substituted by one or more substituents selected from the group consisting of alkyl, cycloalkyl, heterocycloalkyl, aryl, heteroaryl, a crosslinkable or polymerizable group attached via a spacer, and a group with donor or acceptor action;

R$^{22}$ is SiR$^{23}$R$^{24}$R$^{25}$ or a crosslinkable or polymerizable group attached via a spacer;

R$^8$, R$^9$, R$^{23}$, R$^{24}$, and R$^{25}$ are each independently aryl, heteroaryl, alkyl, cycloalkyl, heterocycloalkyl, or a crosslinkable or polymerizable group attached via a spacer;

the group with donor or acceptor action in R$^4$, R$^5$, R$^6$, and R$^7$ is selected from the group consisting of C$_1$- to C$_{20}$-alkoxy, C$_6$- to C$_{30}$-aryloxy, a halogen radical, a halogenated C$_1$- to C$_{20}$-alkyl radical, amino, a pseudohalogen radical, —C(O)OC$_1$- to C$_4$-alkyl, and P(O)R$_2$; and two units of formula (Ia), (Ib), (Ic), (Id), and (Ie) are optionally bridged to one another via a linear or branched, saturated or unsaturated bridge optionally interrupted by at least one heteroatom or via O, where the bridge in formula (Ia), (Ib), (Ic), (Id), and/or (Ie) is in each case attached to the silicon atoms instead of R$^2$.

2. The compound of claim 1, wherein the —NR$^6$R$^7$ group is selected from the group consisting of pyrrolyl, 2,5-dihydro-1-pyrrolyl, pyrrolidinyl, indolyl, indolinyl, isoindolinyl, carbazolyl, azacarbazolyl, diazacarbazolyl, imidazolyl, benzimidazolyl, pyrazolyl, indazolyl, 1,2,3-triazolyl, benzotriazolyl, 1,2,4-triazolyl, tetrazolyl, 1,3-oxazolyl, 1,3-thiazolyl, pentazolyl, piperidyl, morpholinyl, 1,4-oxazinyl, and 9,10-dihydroacridinyl, which are optionally unsubstituted or substituted by one or more substituents selected from the group consisting of alkyl, cycloalkyl, heterocycloalkyl, aryl, heteroaryl, and a group with donor or acceptor action.

3. The compound of claim 1, wherein R$^8$ and R$^9$ are each independently aryl or heteroaryl, which are optionally unsubstituted or substituted by one or more substituents selected from the group consisting of alkyl, cycloalkyl, heterocycloalkyl, aryl, heteroaryl, and a group with donor or acceptor action.

4. The compound of claim 1, selected from the group consisting of

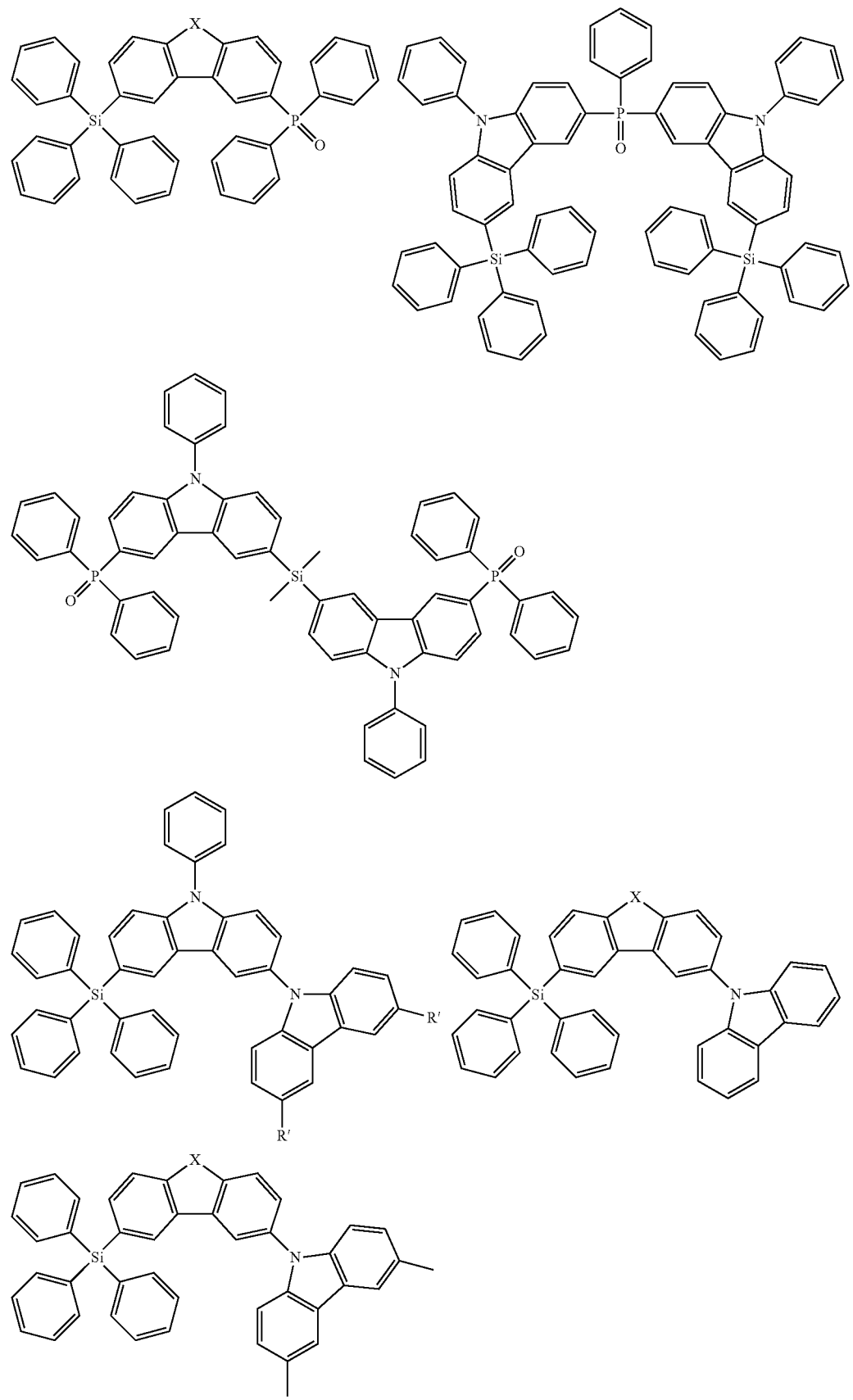

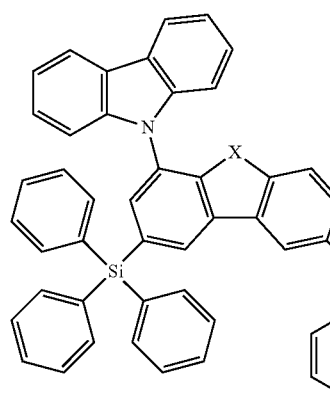
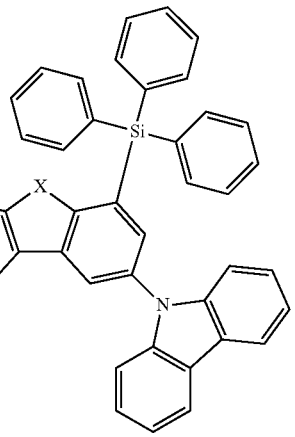
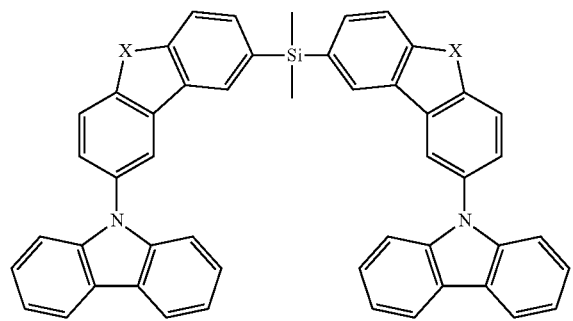
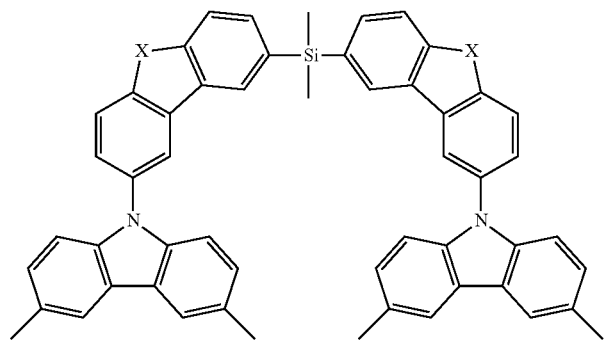
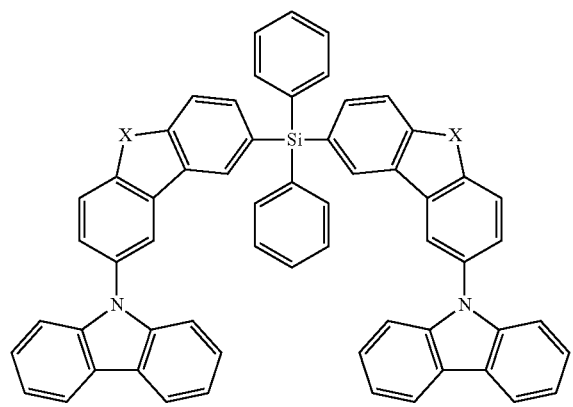
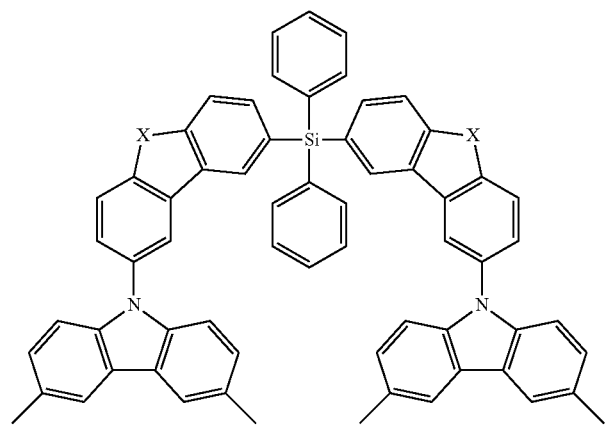
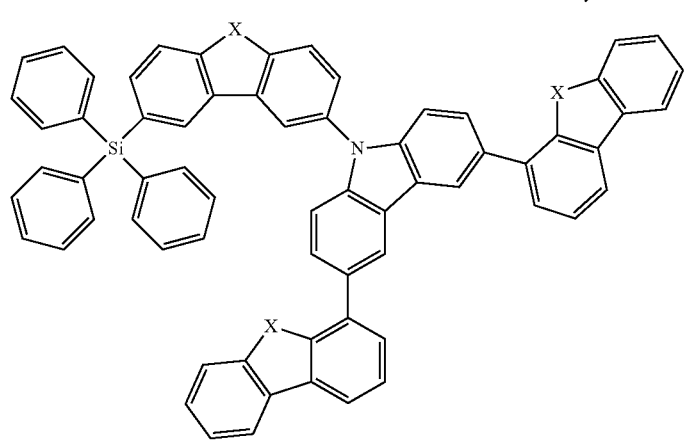

-continued
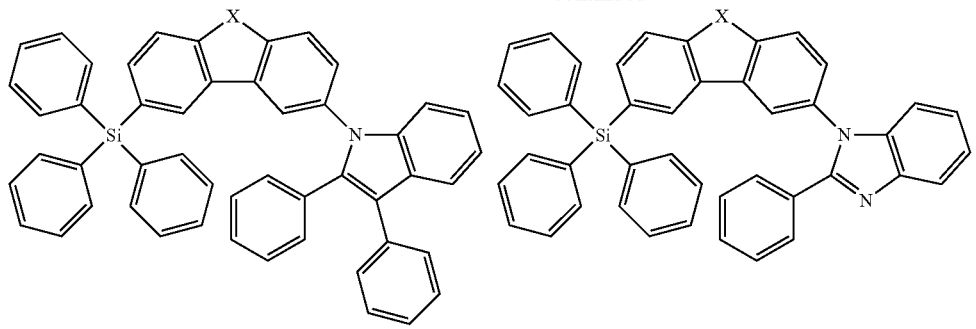
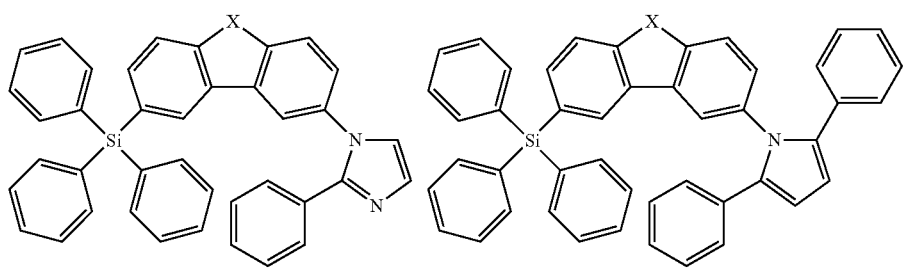
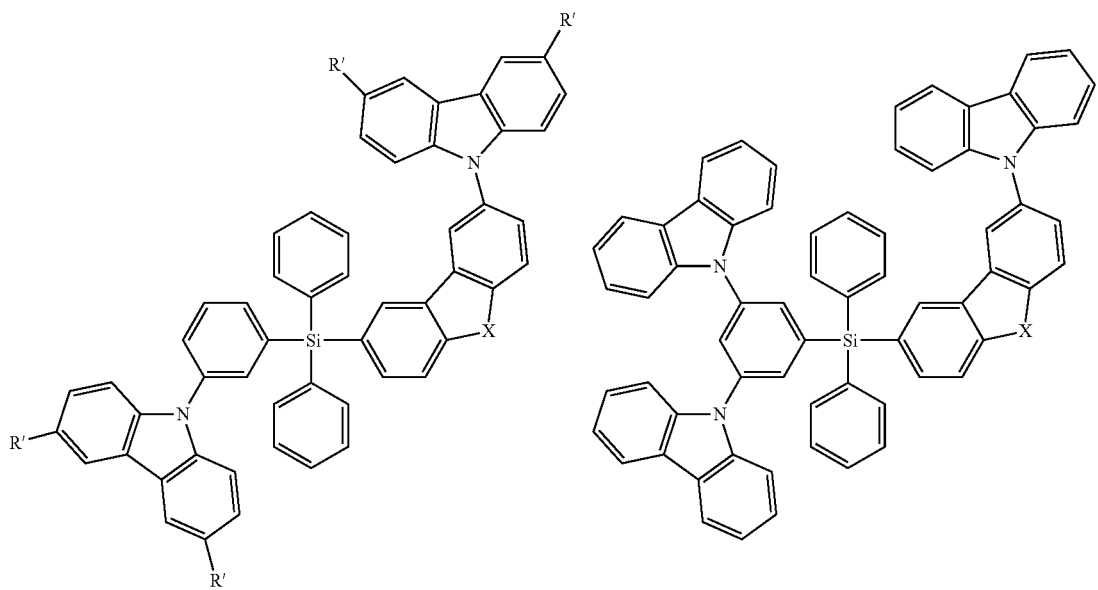
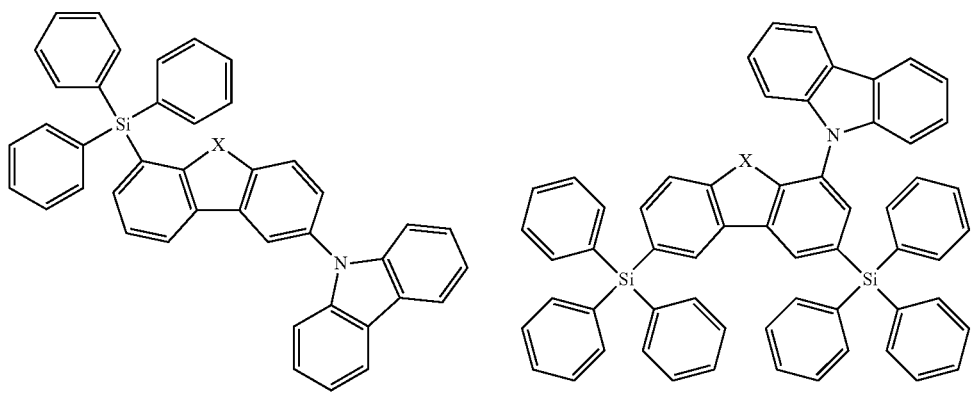

-continued
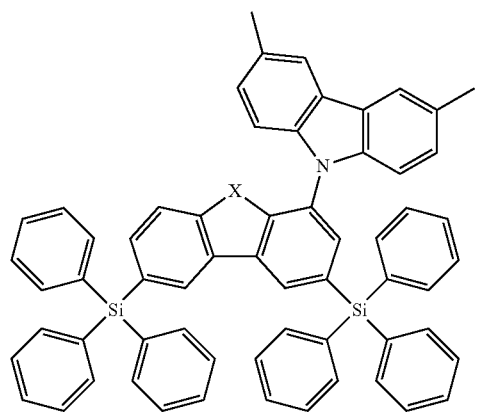
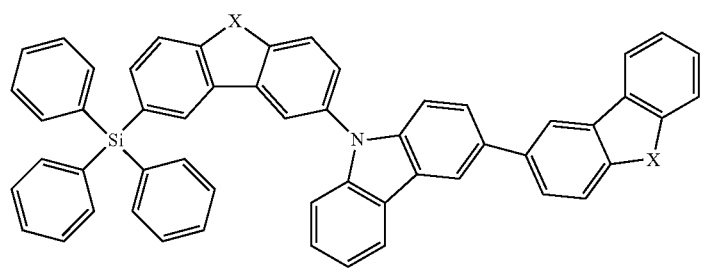
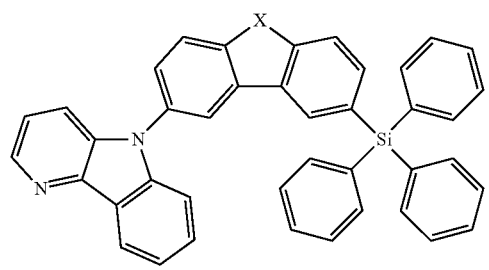
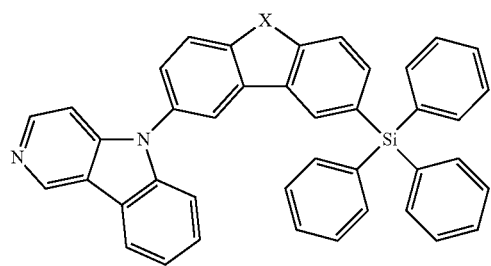
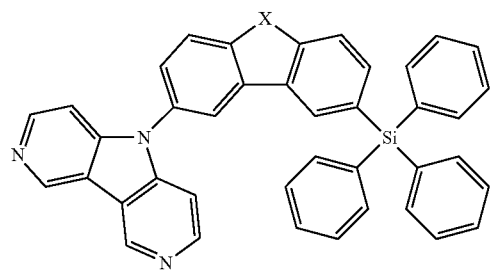
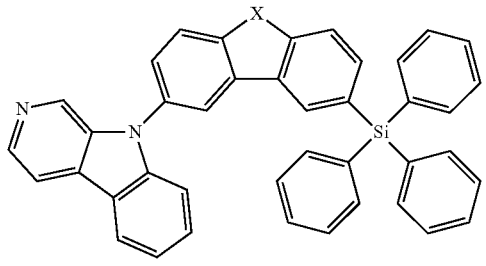

113
114
-continued
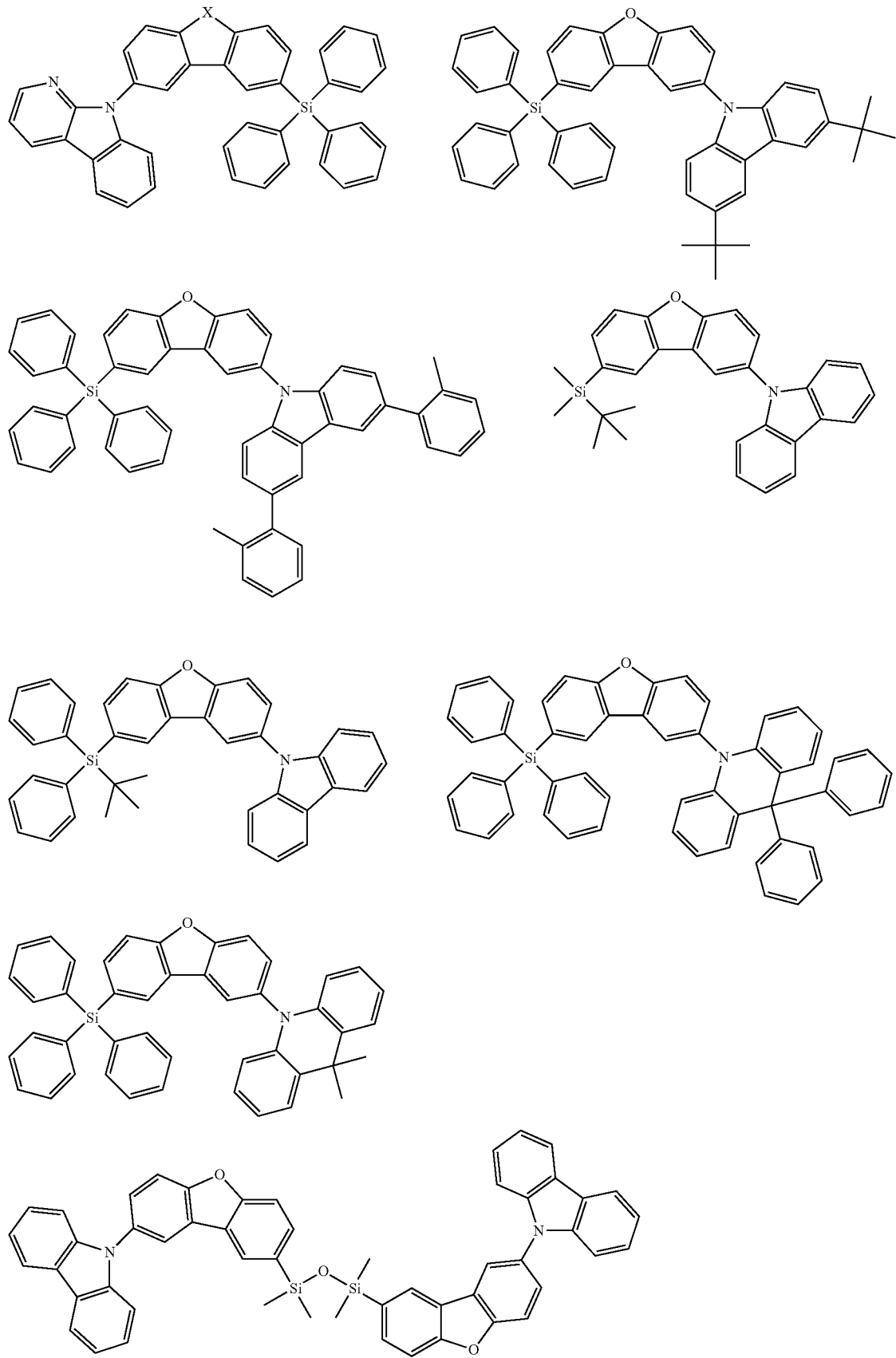

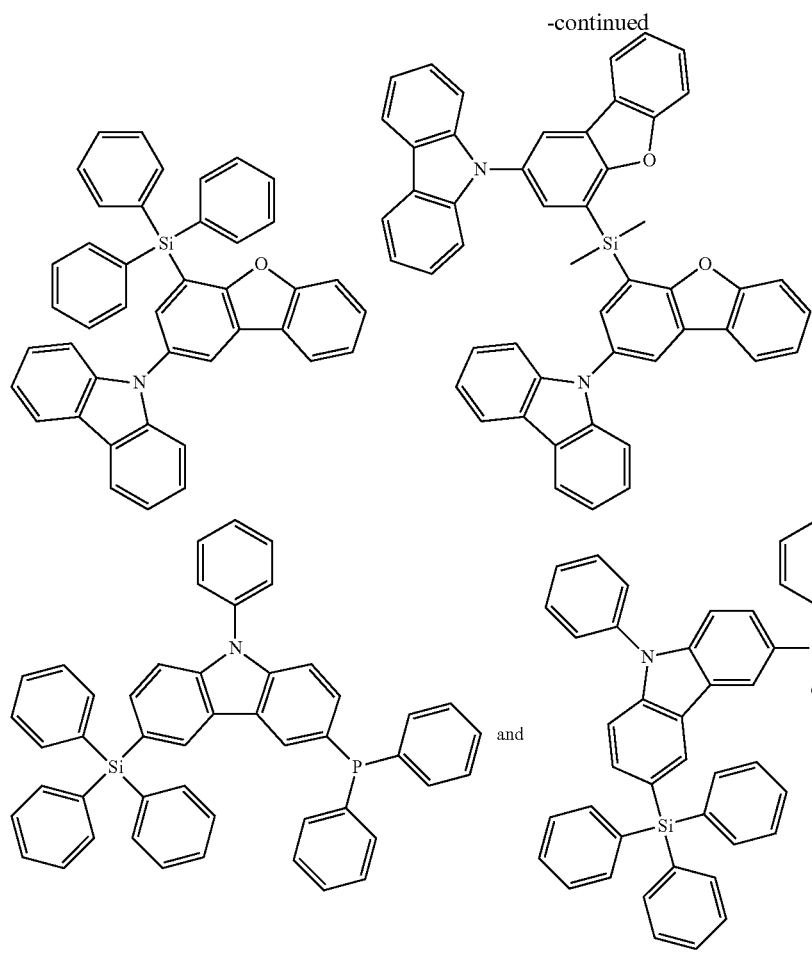

wherein
X is S or O, and
R' is H or CH₃.

5. The compound of claim 1, wherein at least one of $R^1$, $R^2$, $R^3$, $R^4$, $R^5$, $R^8$, $R^9$, $R^{22}$, $R^{23}$, $R^{24}$, and $R^{25}$ is independently a polymerizable or crosslinkable group which is attached via a spacer and is polymerizable or crosslinkable by a method selected from the group consisting of free-radical, cationic polyaddition, and coupling reaction.

6. The compound of claim 1, wherein at least one of $R^1$, $R^2$, and $R^3$ is independently a polymerizable or crosslinkable group attached via a spacer.

7. The compound of claim 1, wherein at least one of $R^1$, $R^2$, $R^3$, $R^4$, $R^5$, $R^6$, $R^7$, $R^8$, $R^9$, $R^{22}$, $R^{23}$, $R^{24}$, and $R^{25}$ comprises at least one polymerizable or crosslinkable group selected from the group consisting of a C—C double bond, an acrylate, a methacrylate, oxetanyl, and 1,2-epoxy ether.

8. A process for preparing at least one compound of formula (Ia), (Ib), (Ic), (Id), and (Ie) of claim 1, wherein the R, $SiR^1R^2R^3$, and A radicals and, where present, $R^4$ and $R^5$ radicals are introduced into a base skeleton of formula (II)

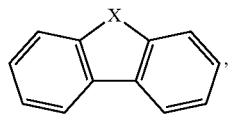
(II)

wherein X is NR, S, or O,
the process comprising Variant a), b), c), or d):
Variant a)
ia) preparing a precursor compound suitable for introduction of the $R^4$, $R^5$, $SiR^1R^2R^3$, and A radicals,
iia) introducing the R radical, and
iiia) introducing the $R^4$ and $R^5$ radicals, where present, and the $SiR^1R^2R^3$ and A radicals;
Variant b)
ib) introducing the R radical,
iib) preparing a precursor compound suitable for introduction of the $R^4$, $R^5$, $SiR^1R^2R^3$, and A radicals, and
iiib) introducing the $R^4$ and $R^5$ radicals, where present, and the $SiR^1R^2R^3$ and A radicals;
Variant c)
ic) preparing a precursor compound suitable for introduction of the $R^4$, $R^5$, $SiR^1R^2R^3$, and A radicals,
iic) introducing the $R^4$ and $R^5$ radicals, where present, and the $SiR^1R^2R^3$ and A radicals, and
iiic) introducing the R radical;
Variant d)
id) preparing a precursor compound suitable for introduction of the $R^4$, $R^5$, $SiR^1R^2R^3$, and A radicals, and
iid) introducing the $R^4$ and $R^5$ radicals, where present, and the $SiR^1R^2R^3$, and A radicals.

9. The process of claim 8, wherein a halogen-metal exchange is performed on a halogenated base skeleton (II) in diethyl ether as a solvent.

10. The process of claim 9, wherein a silane reactant is initially charged simultaneously with a halogenated base skeleton (II) and then a metal reagent is added.

11. The process of claim 8, wherein a silane reactant is initially charged simultaneously with a halogenated base skeleton (H) and then a metal reagent is added.

12. A formulation, comprising a compound of formula (Ia), (Ib), (Ic), (Id), or (Ie) of claim 1,
wherein the formulation is suitable for a liquid-processed application in organic electronics.

13. A process for producing a crosslinked or polymerized material comprising at least one compound of formula (Ia), (Ib), (Ic), (Id), and (Ie) of claim 1 in crosslinked or polymerized form, the process comprising:
(i) preparing a crosslinkable or polymerizable compound of formula (Ia), (Ib), (Ic), (Id), or (Ie), wherein at least one of $R^1$, $R^2$, $R^3$, $R^4$, $R^5$, $R^8$, $R^9$, $R^{22}$, $R^{23}$, $R^{24}$, and $R^{25}$ is a crosslinkable or polymerizable group attached via a spacer, and
(ii) crosslinking or polymerizing the compound of formula (Ia), (Ib), (Ic), (Id), or (Ie) obtained from the preparing (i).

14. A crosslinked or polymerized material, comprising at least one unit of formula (Ia), (Ib), (Ic), (Id), and (Ie) of claim 1 in a crosslinked or a polymerized form.

15. An organic electronics application, comprising the material of claim 14.

16. An organic light-emitting diode, comprising the material of claim 14.

17. A device, comprising at least one organic light-emitting diode of claim 16, wherein the device is selected from the group consisting of a stationary visual display unit, an illumination unit, a keyboard, an item of clothing, furniture, and a carpet.

18. A light-emitting layer, comprising the material of claim 14.

19. A blocking layer for holes/excitons, comprising the material of claim 14.

20. An organic electronics application, comprising at least one compound of formula (Ia), (Ib), (Ic), (Id), and (Ie) of claim 1.

21. The application of claim 20, wherein at least one compound of formula (Ia), (Ib), (Ic), (Id), and (Ie) is at least one of a matrix material, a hole/exciton blocker material, an electron/exciton blocker material, a hole injection material, an electron injection material, a hole conductor material, an electron conductor material, a hole conductor, and an electron conductor.

22. An organic light-emitting diode, comprising at least one compound of formula (Ia), (Ib), (Ic), (Id), and (Ie) of claim 1.

23. The organic light-emitting diode of claim 22, comprising:
an anode An;
a cathode Ka;
at least one light-emitting layer E arranged between the anode An and the cathode Ka; and
optionally, at least one further layer selected from the group consisting of a blocking layer for holes/excitons, a blocking layer for electrons/excitons, and a hole injection layer,
wherein the at least one compound of formula (Ia), (Ib), (Ic), (Id), and (Ie) or a crosslinked or polymerized material of the compound of formula (Ia), (Ib), (Ic), (Id), and (Ie) is present in the light-emitting layer E, in at least one of the further layers, or both.

24. The organic light-emitting diode of claim 23, wherein the at least one compound of formula (Ia), (Ib), (Ic), (Id), and (Ie) is present in the light-emitting layer, in the blocking layer for holes/excitons, or both.

25. The organic light-emitting diode of claim 22, wherein the compound of formula (Ia) has formula (3)

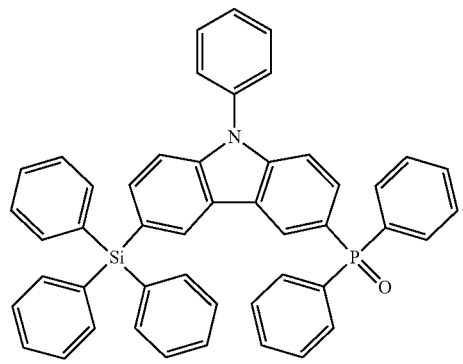

26. The organic light-emitting diode of claim 22, which emits white light.

27. A device, comprising at least one organic light-emitting diode of claim 22, wherein the device is selected from the group consisting of a stationary visual display unit, an illumination unit, a keyboard, an item of clothing, furniture, and a carpet.

28. A light-emitting layer, comprising at least one compound of formula (Ia), (Ib), (Ic), (Id), and (Ie) of claim 1.

29. A blocking layer for holes/excitons, comprising at least one compound of formula (Ia), (Ib), (Ic), (Id), and (Ie) of claim 1.

30. A compound of formula (Ia), (Ib), or (Ic)

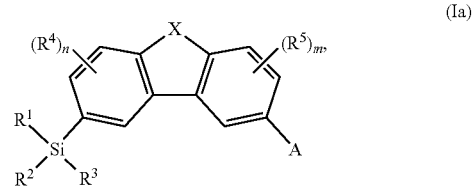

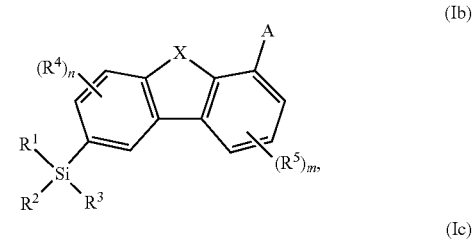

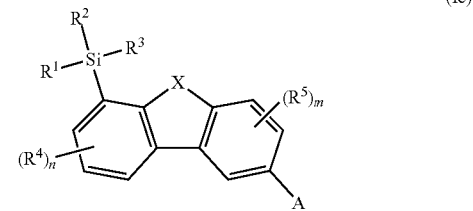

wherein
X is NR, S, or O;
R is aryl;
A is $-NR^6R^7$ or $-P(O)R^8R^9$;
$R^1$, $R^2$, and $R^3$ are each independently aryl, alkyl, wherein at least one of the $R^1$, $R^2$ and $R^3$ radicals is aryl;

R$^4$ and R$^5$ are each independently alkyl, aryl, an A group or a group with donor or acceptor action;

n and m are each independently 0, 1, 2, or 3;

R$^6$ and R$^7$ together with the nitrogen atom form a cyclic radical which has 3 to 10 ring atoms and is optionally unsubstituted or substituted by one or more substituents selected from the group consisting of alkyl, cycloalkyl, heterocycloalkyl, aryl, heteroaryl, and a group with donor or acceptor action, and/or are optionally fused to one or more further cyclic radicals having 3 to 10 ring atoms, where the fused radicals are optionally unsubstituted or substituted by one or more substituents selected from the group consisting of alkyl, cycloalkyl, heterocycloalkyl, aryl, heteroaryl and a group with donor or acceptor action; and R$^8$ and R$^9$, are each independently aryl, heteroaryl, alkyl, cycloalkyl, or heterocycloalkyl.

31. A process for preparing at least one compound of formula (Ia), (Ib), and (Ic) of claim 30, wherein the R, SiR$^1$R$^2$R$^3$, and A radicals and, where present, R$^4$ and R$^5$ radicals are introduced into a base skeleton of formula (II)

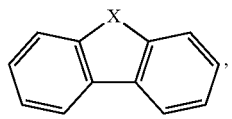
(II)

wherein X is NR, S, or O, the process comprising Variant a), b), c) or d):

Variant a)
ia) preparing a precursor compound suitable for introduction of the R$^4$, R$^5$, SiR$^1$R$^2$R$^3$, and A radicals,
iia) introducing the R radical, and
iiia) introducing the R$^4$ and R$^5$ radicals, where present, and the SiR$^1$R$^2$R$^3$ and A radicals;

Variant b)
ib) introducing the R radical,
iib) preparing a precursor compound suitable for introduction of the R$^4$, R$^5$, SiR$^1$R$^2$R$^3$, and A radicals, and
iiib) introducing the R$^4$ and R$^5$ radicals, where present, and the SiR$^1$R$^2$R$^3$ and A radicals;

Variant c)
ic) preparing a precursor compound suitable for introduction of the R$^4$, R$^5$, SiR$^1$R$^2$R$^3$ and A radicals,
iic) introducing the R$^4$ and R$^5$ radicals, where present, and the SiR$^1$R$^2$R$^3$ and A radicals, and
iiic) introducing the R radical;

Variant d)
id) preparing a precursor compound suitable for introduction of the R$^4$, R$^5$, SiR$^1$R$^2$R$^3$, and A radicals, and
iid) introducing the R$^4$ and R$^5$ radicals, where present, and the SiR$^1$R$^2$R$^3$ and A radicals.

32. A formulation, comprising a compound of formula (Ia), (Ib), or (Ic) of claim 30,
wherein the formulation is suitable for a liquid-processed application in organic electronics.

33. The compound of claim 30, wherein the —NR$^6$R$^7$ group is selected from the group consisting of pyrrolyl, 2,5-dihydro-1-pyrrolyl, pyrrolidinyl, indolyl, indolinyl, isoindolinyl, carbazolyl, azacarbazolyl, diazacarbazolyl, imidazolyl, imidazolinyl, benzimidazolyl, pyrazolyl, indazolyl, 1,2,3-triazolyl, benzotriazolyl, 1,2,4-triazolyl, tetrazolyl, 1,3-oxazolyl, 1,3-thiazolyl, pentazolyl, piperidyl, morpholinyl, 1,4-oxazinyl, and 9,10-dihydroacridinyl, which are optionally unsubstituted or substituted by one or more substituents selected from the group consisting of alkyl, cycloalkyl, heterocycloalkyl, aryl, heteroaryl, and a group with donor or acceptor action.

34. A compound of claim 30, wherein R$^8$ and R$^9$ are each independently aryl or heteroaryl, which are optionally unsubstituted or substituted by one or more substituents selected from the group consisting of alkyl, cycloalkyl, heterocycloalkyl, aryl, heteroaryl, and a group with donor or acceptor action.

35. An organic electronics application, comprising at least one compound of formula (Ia), (Ib), and (Ic) of claim 30.

36. An organic light-emitting diode, comprising at least one compound of formula (Ia), (Ib), and (Ic) of claim 30.

37. A device, comprising at least one organic light-emitting diode of claim 36, wherein the device is selected from the group consisting of a stationary visual display unit, an illumination unit, a keyboard, an item of clothing, furniture, and a carpet.

38. A light-emitting layer, comprising at least one compound of formula (Ia), (Ib), and (Ic) of claim 30.

39. A blocking layer for holes/excitons, comprising at least one compound of formula (Ia), (Ib), and (Ic) of claim 30.

40. A compound of formula (Ia), (Ib), (Ic), (Id), or (Ie)

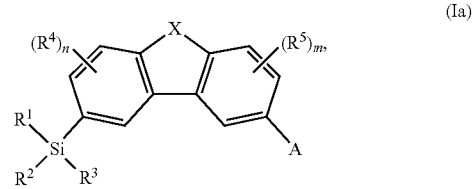
(Ia)

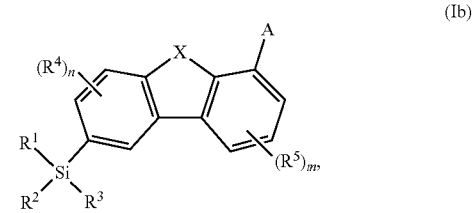
(Ib)

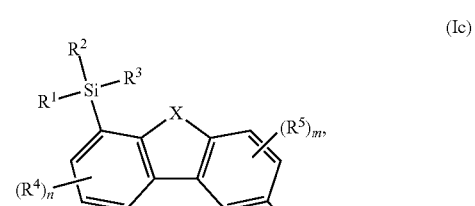
(Ic)

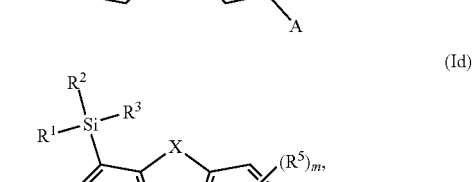
(Id)

-continued (Ie)

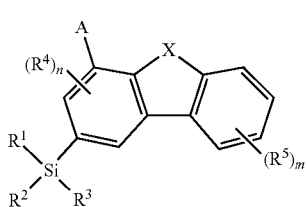

wherein

X is NR, S, O, or PR,

R is aryl, heteroaryl, alkyl, cycloalkyl, or heterocycloalkyl,

A is $-NR^6R^7$, $-P(O)R^8R^9$, $-PR^{10}R^{11}$, $-S(O)_2R^{12}$, $-S(O)R^{13}$, $-SR^{14}$ or $OR^{15}$, $R^1$, $R^2$, and $R^3$ are each independently aryl, heteroaryl, alkyl, cycloalkyl, heterocycloalkyl, where at least one of the $R^1$, $R^2$, and $R^3$ radicals comprises at least two carbon atoms, or $OR^{22}$, and at least one of $R^1$, $R^2$, and $R^3$, is independently a polymerizable or crosslinkable group attached via a spacer, $R^4$ and $R^5$ are each independently alkyl, cycloalkyl, heterocycloalkyl, aryl, heteroaryl, or a crosslinkable or polymerizable group attached via a spacer, an A group, or a group with donor or acceptor action, n and m are each independently 0, 1, 2, or 3, $R^6$ and $R^7$ together with the nitrogen atom form a cyclic radical which has 3 to 10 ring atoms and is optionally unsubstituted or substituted by one or more substituents selected from the group consisting of alkyl, cycloalkyl, heterocycloalkyl, aryl, heteroaryl and a group with donor or acceptor action, and/or optionally fused to one or more further cyclic radicals having 3 to 10 ring atoms, where the fused radicals are optionally unsubstituted or substituted by one or more substituents selected from the group consisting of alkyl, cycloalkyl, heterocycloalkyl, aryl, heteroaryl, a crosslinkable or polymerizable group attached via a spacer, and a group with donor or acceptor action, $R^{22}$ is independently $SiR^{23}R^{24}R^{25}$, aryl, heteroaryl, alkyl, cycloalkyl, heterocycloalkyl, or a crosslinkable or polymerizable group attached via a spacer, optionally substituted by an $OR^{28}$ group, $R^{28}$ is independently $SiR^{23}R^{24}R^{25}$, aryl, heteroaryl, alkyl, cycloalkyl, heterocycloalkyl, or a crosslinkable or polymerizable group attached via a spacer, $R^8$, $R^9$, $R^{10}$, $R^{11}$, $R^{12}$, $R^{13}$, $R^{14}$, $R^{23}$, $R^{24}$, and $R^{25}$ are each independently aryl, heteroaryl, alkyl, cycloalkyl, heterocycloalkyl, or a crosslinkable or polymerizable group attached via a spacer, $R^{15}$ is aryl or heteroaryl unsubstituted or substituted by one or more substituents selected from the group consisting of alkyl, cycloalkyl, heterocycloalkyl, aryl, heteroaryl and a group with donor or acceptor action, and two units of formula (Ia), (Ib), (Ic), (Id), and (Ie) are optionally bridged to one another via a linear or branched, saturated or unsaturated bridge optionally interrupted by at least one heteroatom or via O, where the bridge in formula (Ia), (Ib), (Ic), (Id), and/or (Ie) is in each case attached to the silicon atoms instead of $R^2$.

41. The compound of claim 40, wherein at least one of $R^1$, $R^2$, and $R^3$ is an aromatic unit of formula (IIa), (IIb), (IIc), (IId) or (IIe)

(IIa)
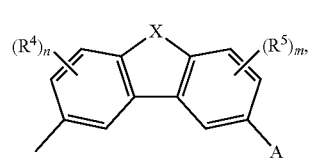

(IIb)
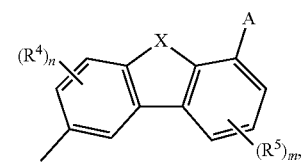

(IIc)
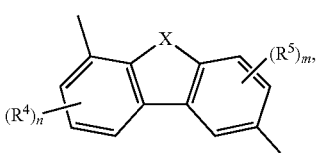

(IId)
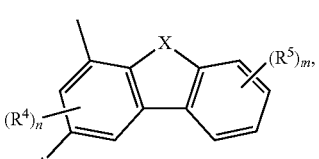

(IIe)
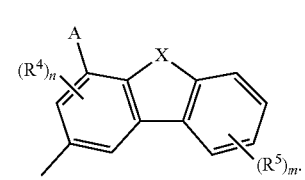

42. An organic electronics application, comprising at least one compound of formula (Ia), (Ib), (Ic), (Id), and (Ie) of claim 40.

43. A crosslinked or polymerized material, comprising at least one unit of formula (Ia), (Ib), (Ic), (Id), or (Ie) in crosslinked or polymerized form, (Ia)
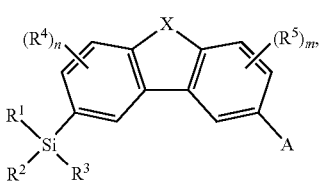

(Ib)
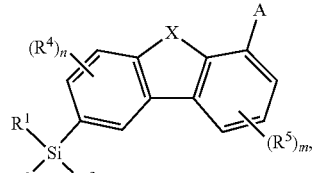

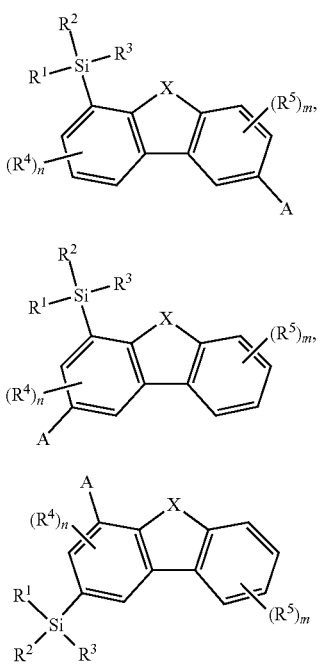

wherein
X is NR, S, O or PR,
R is aryl, heteroaryl, alkyl, cycloalkyl, or heterocycloalkyl,
A is $-NR^6R^7$, $-P(O)R^8R^9$, $-PR^{10}R^{11}$, $-S(O)_2R^{12}$, $-S(O)R^{13}$, $-SR^{14}$ or $-OR^{15}$,
$R^1$, $R^2$, and $R^3$ are each independently aryl, heteroaryl, alkyl, cycloalkyl, heterocycloalkyl, or a crosslinkable or polymerizable group attached via a spacer, where at least one of the $R^1$, $R^2$, and $R^3$ radicals comprises at least two carbon atoms, or $OR^{22}$,
$R^4$ and $R^5$ are each independently alkyl, cycloalkyl, heterocycloalkyl, aryl, heteroaryl, or a crosslinkable or polymerizable group attached via a spacer, an A group, or a group with donor or acceptor action,
n and m are each independently 0, 1, 2, or 3,
$R^6$ and $R^7$ together with the nitrogen atom form a cyclic radical which has 3 to 10 ring atoms and is optionally unsubstituted or substituted by one or more substituents selected from the group consisting of alkyl, cycloalkyl, heterocycloalkyl, aryl, heteroaryl, and a group with donor or acceptor action, and/or optionally fused to one or more further cyclic radicals having 3 to 10 ring atoms, where the fused radicals are optionally unsubstituted or substituted by one or more substituents selected from the group consisting of alkyl, cycloalkyl, heterocycloalkyl, aryl, heteroaryl, a crosslinkable or polymerizable group attached via a spacer, and a group with donor or acceptor action,
$R^{22}$ is independently $SiR^{23}R^{24}R^{25}$, aryl, heteroaryl, alkyl, cycloalkyl, heterocycloalkyl, or a crosslinkable or polymerizable group attached via a spacer, optionally substituted by an $OR^{28}$ group,
$R^{28}$ is independently $SiR^{23}R^{24}R^{25}$, aryl, heteroaryl, alkyl, cycloalkyl, heterocycloalkyl, or a crosslinkable or polymerizable group attached via a spacer,
$R^8$, $R^9$, $R^{10}$, $R^{11}$, $R^{12}$, $R^{13}$, $R^{14}$, $R^{23}$, $R^{24}$, and $R^{25}$ are each independently aryl, heteroaryl, alkyl, cycloalkyl, heterocycloalkyl, or a crosslinkable or polymerizable group attached via a spacer,
$R^{15}$ is aryl or heteroaryl unsubstituted or substituted by one or more substituents selected from the group consisting of alkyl, cycloalkyl, heterocycloalkyl, aryl, heteroaryl and a group with donor or acceptor action,
and
two units of formula (Ia), (Ib), (Ic), (Id), and (Ie) are optionally bridged to one another via a linear or branched, saturated or unsaturated bridge optionally interrupted by at least one heteroatom or via O, where the bridge in formula (Ia), (Ib), (Ic), (Id), and/or (Ie) is in each case attached to the silicon atoms instead of $R^2$.

44. An organic electronics application, comprising the material of claim 43.

45. An organic light-emitting diode, comprising the material of claim 43.

46. A device, comprising at least one organic light-emitting diode of claim 45, wherein the device is selected from the group consisting of a stationary visual display unit, an illumination unit, a keyboard, an item of clothing, furniture, and a carpet.

47. A light-emitting layer, comprising the material of claim 43.

48. A blocking layer for holes/excitons, comprising the material of claim 43.

* * * * *